United States Patent
Ikegaya et al.

(10) Patent No.: US 6,313,071 B1
(45) Date of Patent: Nov. 6, 2001

(54) PHENYLACETYLENE DERIVATIVES AND AGRICULTURAL/HORTICULTURAL FUNGICIDES

(75) Inventors: Kazuhiro Ikegaya, Fujieda; Shunichiro Fukumoto; Masami Ozaki, both of Iwata-gun; Takahiro Kawashima, Kashiwa; Haruchika Sekido, Kawasaki; Norimichi Muramatsu, Kakegawa, all of (JP)

(73) Assignees: Kumiai Chemical Industry Co., Ltd.; Ihara Chemical Industry Co., Ltd., both of Tokyo (JP)

( * ) Notice: Subject to any disclaimer, the term of this patent is extended or adjusted under 35 U.S.C. 154(b) by 0 days.

(21) Appl. No.: 09/701,390

(22) PCT Filed: Jun. 3, 1999

(86) PCT No.: PCT/JP99/02973

§ 371 Date: Dec. 4, 2000

§ 102(e) Date: Dec. 4, 2000

(87) PCT Pub. No.: WO99/62869

PCT Pub. Date: Sep. 12, 1999

(30) Foreign Application Priority Data

Jun. 4, 1998 (JP) .................................................. 10-170508

(51) Int. Cl.[7] ........................ A01N 33/00; C07C 271/02; C07C 271/06
(52) U.S. Cl. ........................... 504/143; 560/24; 556/420; 564/56
(58) Field of Search ................................. 564/32, 47, 56; 560/19, 24, 30, 87; 556/413, 420; 504/143

(56) References Cited

PUBLICATIONS

CA:126:3033553 abs of US5618843, Apr. 1997.*
CA:125:195447 abs of WO9622288, Jul. 1996.*

* cited by examiner

Primary Examiner—Jean F. Vollano
(74) Attorney, Agent, or Firm—Oblon, Spivak, McClelland, Maier & Neustadt, P.C.

(57) ABSTRACT

A phenylacetylene derivative represented by the formula [I]:

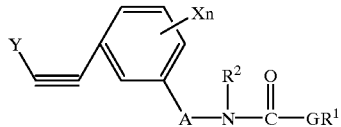

{wherein X is a halogen atom, a $C_1$–$C_6$ alkyl group, a $C_2$–$C_6$ alkoxy group, a $C_2$–$C_6$ haloalkyl group, etc., n is 0 or an integer of from 1 to 4, $R^1$ is a $C_1$–$C_6$ alkyl group, $R^2$ is a hydrogen atom, a $C_1$–$C_6$ alkyl group, a $C_2$–$C_6$ alkynyl group, a $C_2$–$C_6$ alkynyl group, a $C_1$–$C_6$ alkoxy group, etc., A is a $C_1$–$C_6$ alkylene group which may be branched, G is an oxygen atom, a sulfur atom or a —$NR^3$— group; $R^3$ is a hydrogen atom or a $C_1$–$C_6$ alkyl group, and Y is a hydrogen atom, a $C_1$–$C_{10}$ alkyl group, said group may be substituted by a halogen atom, a hydroxyl group or a $C_1$–$C_6$ alkoxy group], a $C_2$–$C_6$ alkenyl group, etc.; and an agricultural/horticultural fungicide containing the same as the active ingredient.

9 Claims, No Drawings

PHENYLACETYLENE DERIVATIVES AND AGRICULTURAL/HORTICULTURAL FUNGICIDES

This application is the national phase of PCT/JP99/02973, filed Jun. 3, 1999 now WO99/62869.

TECHNICAL FIELD

The present invention relates to a novel phenylacetylene derivative and an agricultural/horticultural fungicide containing the same as the active ingredient.

BACKGROUND ART

Heretofore, many carbamic acid derivatives have been reported, but it has not been known that a carbamic acid derivative having a phenylacetylene group as the compound of the present invention has excellent fungicidal activities.

The object of the present invention is to provide a novel phenylacetylene derivative and an agricultural/horticultural fungicide containing the same as the active ingredient.

The present inventors have conducted an extensive study to produce a novel agricultural/horticultural fungicide and, as a result, have found that the phenylacetylene derivative of the present invention (hereinafter referred to as the compound of the present invention) is a novel compound not disclosed in literatures and exhibits remarkable effects as an agricultural/horticultural fungicide, and have finally accomplished the present invention.

DISCLOSURE OF THE INVENTION

Namely, the present invention provides a phenylacetylene derivative represented by the general formula [I]:

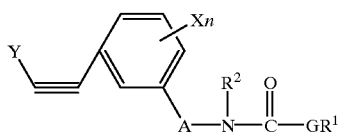

[I]

{wherein X is a halogen atom, a $C_1$–$C_6$ alkyl group, a $C_1$–$C_6$ alkoxy group, a $C_1$–$C_6$ haloalkyl group or a $C_1$–$C_6$ haloalkoxy group, n is 0 or an integer of from 1 to 4, $R^1$ is a $C_1$–$C_6$ alkyl group, $R^2$ is a hydrogen atom, a $C_1$–$C_6$ alkyl group, a $C_2$–$C_6$ alkenyl group, a $C_2$–$C_6$ alkynyl group, a $C_1$–$C_6$ alkoxy group, a $C_1$–$C_6$ alkoxy $C_1$–$C_6$ alkyl group, a $C_1$–$C_6$ alkylcarbonyl group or a $C_1$–$C_6$ alkoxycarbonyl group, A is a $C_1$–$C_6$ alkylene group which may be branched, G is an oxygen atom, a sulfur atom or a —$NR^3$— group [$R^3$ is a hydrogen atom or a $C_1$–$C_6$ alkyl group], and Y is a hydrogen atom, a $C_1$–$C_6$ alkyl group [said group may be substituted by a halogen atom, a hydroxyl group, a phenyl group or a $C_1$–$C_6$ alkoxy group], a $C_2$–$C_{10}$ alkenyl group, a $C_2$–$C_{10}$ alkynyl group, a $C_3$–$C_6$ cycloalkyl group [said group may be substituted by a halogen atom, a hydroxyl group or a $C_1$–$C_6$ alkoxy group], a $C_3$–$C_6$ cycloalkenyl group, a $C_3$–$C_6$ cycloalkyl-$C_1$–$C_6$ alkyl group, an aryl-$C_1$–$C_6$ alkyl group [said group may be substituted by a halogen atom, a $C_1$–$C_6$ alkyl group or a $C_1$–$C_6$ alkoxy group], $C(O)R^4$, $COOR^5$, or a $SiR^6R^7R^8$ group [$R^4$ to $R_8$ are the same or different and represent a hydrogen atom or a $C_1$–$C_6$ alkyl group]}; an agricultural/horticultural fungicide containing the same as the active ingredient; and a method for controlling an agricultural/horticultural plant disease, which employs a fungicidally effective amount thereof.

Symbols and terms used in this specification will be explained.

The halogen atom is a fluorine atom, a chlorine atom, a bromine atom or an iodine atom.

A notation such as $C_1$–$C_{10}$ indicates that the carbon number of a substituent following this notation is from 1 to 10 in this case.

The $C_1$–$C_6$ alkyl group represents a straight chain or branched chain alkyl group and may, for example, be a group such as methyl, ethyl, n-propyl, isopropyl, n-butyl, isobutyl, sec-butyl, tert-butyl, n-pentyl, isopentyl, neopentyl, n-hexyl, 1,1-dimethylpropyl or 1,1-dimethylbutyl.

The $C_1$–$C_{10}$ alkyl group may, for example, be the above-mentioned alkyl group, or a group such as heptyl, octyl, 1,1-diethylbutyl, nonyl or decyl.

The $C_3$–$C_6$ cycloalkyl group may, for example, be a group such as cyclopropyl, cyclobutyl, cyclopentyl or cyclohexyl.

The $C_3$–$C_6$ cycloalkenyl group may, for example, be a group such as 1-cyclopenten-1-yl, 2-cyclopenten-1-yl, 1-cyclohexen-1-yl or 2-cyclohexen-1-yl.

The $C_1$–$C_6$ haloalkyl group represents a straight chain or branched chain alkyl group substituted by a halogen atom and may, for example, be a group such as fluoromethyl, chloromethyl, difluoromethyl, dichloromethyl, trifluoromethyl or pentafluoroethyl.

The $C_2$–$C_{10}$ alkenyl group represents a straight chain or branched chain alkenyl group and may, for example, be a group such as vinyl, 1-propenyl, 2-propenyl, isopropenyl, 1-butenyl, 2-butenyl, 1-hexenyl or 1-octenyl.

The $C_2$–$C_{10}$ alkynyl group represents a straight chain or branched chain alkynyl group and may, for example, be a group such as ethynyl, 1-propynyl, 2-propynyl, 1-butynyl, 2-butynyl, 3-butynyl, 4-methyl-1-pentynyl or 3-methyl-1-pentynyl.

The $C_1$–$C_6$ alkoxy group represents an alkyloxy group wherein the alkyl moiety has the above-mentioned meaning.

The $C_1$–$C_6$ haloalkoxy group represents a haloalkyloxy group wherein the haloalkyl moiety has the above-mentioned meaning.

The $C_1$–$C_6$ alkylcarbonyl group represents an alkylcarbonyl group wherein the alkyl moiety has the above-mentioned meaning.

The $C_1$–$C_6$ alkoxycarbonyl group represents an alkoxycarbonyl group wherein the alkoxy moiety has the above-mentioned meaning.

The $C_1$–$C_6$ alkylene group which may be branched, may, for example, be a group such as —$CH_2$—, —$CH(CH_3)$—, —$C(CH_3)_2$—, —$CH_2CH_2$— or —$CH_2CH_2CH_2$—.

The aryl $C_1$–$C_6$ alkyl group may, for example, be a group such as a benzyl group.

Now, specific examples of the compound of the present invention represented by the general formula [I] will be disclosed in Tables 1 to 52. However, the compound of the present invention is not limited to such compounds. Further, the compound numbers will be referred to in the subsequent description.

Symbols in the Tables have the following meanings respectively. Me represents a methyl group, Et represents an ethyl group, Pr represents a n-propyl group, Pr-i represents an isopropyl group, Bu represents a n-butyl group, Bu-i represents an isobutyl group, Bu-s represents a sec-butyl group, Bu-t represents a tert-butyl group, $C_3H_5$-c represents a cyclopropyl group, $C_5H_9$-c represents a cyclopentyl group, $C_6H_{11}$-c represents a cyclohexyl group, and Ph represents a phenyl group.

TABLE 1

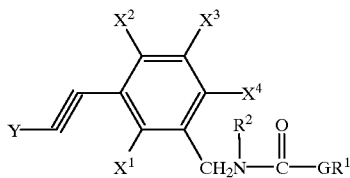

| Compound No. | X¹ | X² | X³ | X⁴ | Y | G | R¹ | R² | m.p. (° C.) |
|---|---|---|---|---|---|---|---|---|---|
| 1-1 | H | H | H | H | H | O | Me | H | |
| 1-2 | H | H | H | H | Me | O | Me | H | |
| 1-3 | H | H | H | H | Et | O | Me | H | |
| 1-4 | H | H | H | H | Pr-i | O | Me | H | |
| 1-5 | H | H | H | H | Bu | O | Me | H | |
| 1-6 | H | H | H | H | Bu-i | O | Me | H | |
| 1-7 | H | H | H | H | Bu-t | O | Me | H | Oily |
| 1-8 | H | H | H | H | $C_5H_{11}$ | O | Me | H | |
| 1-9 | H | H | H | H | CHMePr | O | Me | H | |
| 1-10 | H | H | H | H | $C_6H_{13}$ | O | Me | H | |
| 1-11 | H | H | H | H | $C_5H_9$-c | O | Me | H | |
| 1-12 | H | H | H | H | CH=CH$_2$ | O | Me | H | |
| 1-13 | H | H | H | H | C(Me)=CH$_2$ | O | Me | H | |
| 1-14 | H | H | H | H | C(Me)=CHMe | O | Me | H | |
| 1-15 | H | H | H | H | CH$_2$C≡CEt | O | Me | H | |
| 1-16 | H | H | H | H | CHClMe | O | Me | H | |
| 1-17 | H | H | H | H | CHClEt | O | Me | H | |
| 1-18 | H | H | H | H | CHClPr | O | Me | H | |
| 1-19 | H | H | H | H | CH$_2$CHClMe | O | Me | H | |
| 1-20 | H | H | H | H | CClMe$_2$ | O | Me | H | |
| 1-21 | H | H | H | H | CClMeEt | O | Me | H | |
| 1-22 | H | H | H | H | CClMePr | O | Me | H | |
| 1-23 | H | H | H | H | CClMePh | O | Me | H | |
| 1-24 | H | H | H | H | CH(OMe)Me | O | Me | H | |
| 1-25 | H | H | H | H | CH(OMe)Pr | O | Me | H | |
| 1-26 | H | H | H | H | CH$_2$CH(OMe)Me | O | Me | H | |
| 1-27 | H | H | H | H | C(OMe)Me$_2$ | O | Me | H | |
| 1-28 | H | H | H | H | C(OMe)MeEt | O | Me | H | |
| 1-29 | H | H | H | H | C(OMe)MePr | O | Me | H | |

TABLE 2

| Compound No. | X¹ | X² | X³ | X⁴ | Y | G | R¹ | R² | m.p. (° C.) |
|---|---|---|---|---|---|---|---|---|---|
| 1-30 | H | H | H | H | C(OMe)MeBu-t | O | Me | H | |
| 1-31 | H | H | H | H | SiMe$_3$ | O | Me | H | |
| 1-32 | H | H | H | H | SiEt$_3$ | O | Me | H | Oily |
| 1-33 | H | H | H | H | CH$_2$Ph | O | Me | H | |
| 1-34 | H | H | H | H | CF$_3$ | O | Me | H | |
| 1-35 | H | H | H | F | H | O | Me | H | 102–104 |
| 1-36 | H | H | H | F | Me | O | Me | H | 75–78 |
| 1-37 | H | H | H | F | Et | O | Me | H | |
| 1-38 | H | H | H | F | Pr | O | Me | H | |
| 1-39 | H | H | H | F | Pr-i | O | Me | H | |
| 1-40 | H | H | H | F | Bu | O | Me | H | |
| 1-41 | H | H | H | F | Bu-i | O | Me | H | |
| 1-42 | H | H | H | F | Bu-s | O | Me | H | |
| 1-43 | H | H | H | F | Bu-t | O | Me | H | 102–105 |
| 1-44 | H | H | H | F | $C_5H_{11}$ | O | Me | H | |
| 1-45 | H | H | H | F | CHMePr | O | Me | H | |
| 1-46 | H | H | H | F | CH$_2$CH$_2$CH$_2$Pr-i | O | Me | H | |
| 1-47 | H | H | H | F | CH$_2$CHMeEt | O | Me | H | |
| 1-48 | H | H | H | F | $C_6H_{13}$ | O | Me | H | |
| 1-49 | H | H | H | F | $C_7H_{15}$ | O | Me | H | |
| 1-50 | H | H | H | F | $C_8H_{17}$ | O | Me | H | |
| 1-51 | H | H | H | F | $C_9H_{19}$ | O | Me | H | |
| 1-52 | H | H | H | F | $C_{10}H_{21}$ | O | Me | H | |
| 1-53 | H | H | H | F | $C_3H_5$-c | O | Me | H | |
| 1-54 | H | H | H | F | $C_5H_9$-c | O | Me | H | 72–75 |
| 1-55 | H | H | H | F | $C_6H_{11}$-c | O | Me | H | |
| 1-56 | H | H | H | F | CH$_2$—$C_5H_9$-c | O | Me | H | |
| 1-57 | H | H | H | F | CH$_2$—$C_6H_{11}$-c | O | Me | H | |

TABLE 2-continued

| Compound No. | X¹ | X² | X³ | X⁴ | Y | G | R¹ | R² | m.p. (° C.) |
|---|---|---|---|---|---|---|---|---|---|
| 1-58 | H | H | H | F | CH=CH$_2$ | O | Me | H | 80–83 |
| 1-59 | H | H | H | F | C(Me)=CH$_2$ | O | Me | H | |
| 1-60 | H | H | H | F | C(Me)=CHMe | O | Me | H | Oily |

TABLE 3

| Compound No. | X¹ | X² | X³ | X⁴ | Y | G | R¹ | R² | m.p. (° C.) |
|---|---|---|---|---|---|---|---|---|---|
| 1-61 | H | H | H | F | CH$_2$CH=CH$_2$ | O | Me | H | |
| 1-62 | H | H | H | F | CH$_2$C≡CEt | O | Me | H | |
| 1-63 | H | H | H | F | 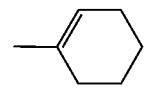 | O | Me | H | |
| 1-64 | H | H | H | F | CH(OH)Me | O | Me | H | Oily |
| 1-65 | H | H | H | F | CH(OH)Et | O | Me | H | |
| 1-66 | H | H | H | F | CH(OH)Pr | O | Me | H | |
| 1-67 | H | H | H | F | CH(OH)Pr-i | O | Me | H | |
| 1-68 | H | H | H | Cl | CH(OH)Bu-i | O | Me | H | Oily |
| 1-69 | H | H | H | F | CH$_2$CH(OH)Me | O | Me | H | |
| 1-70 | H | H | H | F | C(OH)Me$_2$ | O | Me | H | |
| 1-71 | H | H | H | F | C(OH)MeEt | O | Me | H | Oily |
| 1-72 | H | H | H | F | C(OH)MePr | O | Me | H | |
| 1-73 | H | H | H | F | C(OH)MeBu-t | O | Me | H | |
| 1-74 | H | H | H | F | C(OH)Et$_2$ | O | Me | H | |
| 1-75 | H | H | H | F | C(OH)MePh | O | Me | H | |
| 1-76 | H | H | H | F | CH(OH)Ph | O | Me | H | |
| 1-77 | H | H | H | F | CHClMe | O | Me | H | 86–89 |
| 1-78 | H | H | H | F | CHClEt | O | Me | H | |
| 1-79 | H | H | H | F | CHClPr | O | Me | H | |
| 1-80 | H | H | H | F | CHClPr-i | O | Me | H | |
| 1-81 | H | H | H | F | CH$_2$CHClMe | O | Me | H | |
| 1-82 | H | H | H | F | CClMe$_2$ | O | Me | H | |
| 1-83 | H | H | H | F | CClMeEt | O | Me | H | |
| 1-84 | H | H | H | F | CClMePr | O | Me | H | |
| 1-85 | H | H | H | F | CClMeBu-t | O | Me | H | |
| 1-86 | H | H | H | F | CClEt$_2$ | O | Me | H | |
| 1-87 | H | H | H | F | CClMePh | O | Me | H | |
| 1-88 | H | H | H | F | CHClPh | O | Me | H | |
| 1-89 | H | H | H | F | CH$_2$OMe | O | Me | H | |
| 1-90 | H | H | H | F | CH$_2$OEt | O | Me | H | |
| 1-91 | H | H | H | F | CH(OMe)Me | O | Me | H | |
| 1-92 | H | H | H | F | CH(OMe)Et | O | Me | H | |
| 1-93 | H | H | H | F | CH(OMe)Pr | O | Me | H | |
| 1-94 | H | H | H | F | CH(OMe)Pr-i | O | Me | H | |

TABLE 4

| Compound No. | X¹ | X² | X³ | X⁴ | Y | G | R¹ | R² | m.p. (° C.) |
|---|---|---|---|---|---|---|---|---|---|
| 1-95 | H | H | H | F | CH$_2$CH(OMe)Me | O | Me | H | |
| 1-96 | H | H | H | F | C(OMe)Me$_2$ | O | Me | H | |
| 1-97 | H | H | H | F | C(OMe)MeEt | O | Me | H | |
| 1-98 | H | H | H | F | C(OMe)MePr | O | Me | H | |
| 1-99 | H | H | H | F | C(OMe)MeBu-t | O | Me | H | |
| 1-100 | H | H | H | F | C(OMe)Et$_2$ | O | Me | H | |
| 1-101 | H | H | H | F | C(OMe)MePh | O | Me | H | |
| 1-102 | H | H | H | F | CH(OMe)Ph | O | Me | H | |
| 1-103 | H | H | H | F | 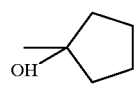 | O | Me | H | |

TABLE 4-continued

| Compound No. | X¹ | X² | X³ | X⁴ | Y | G | R¹ | R² | m.p. (° C.) |
|---|---|---|---|---|---|---|---|---|---|
| 1-104 | H | H | H | F | 1-methylcyclohexan-1-ol (2-substituted) | O | Me | H | |
| 1-105 | H | H | H | F | SiMe₃ | O | Me | H | Oily |
| 1-106 | H | H | H | F | SiEt₃ | O | Me | H | |
| 1-107 | H | H | H | F | CH₂Ph | O | Me | H | |
| 1-108 | H | H | H | F | CF₃ | O | Me | H | |
| 1-109 | H | H | H | F | COMe | O | Me | H | |
| 1-110 | H | H | H | F | COOMe | O | Me | H | |
| 1-111 | H | H | H | F | COOEt | O | Me | H | |
| 1-112 | H | H | H | F | COOH | O | Me | H | |
| 1-113 | H | H | H | Cl | H | O | Me | H | 99–101 |
| 1-114 | H | H | H | Cl | Me | O | Me | H | 89–91 |
| 1-115 | H | H | H | Cl | Et | O | Me | H | 54–57 |
| 1-116 | H | H | H | Cl | Pr | O | Me | H | Oily |
| 1-117 | H | H | H | Cl | Pr-i | O | Me | H | 93–96 |
| 1-118 | H | H | H | Cl | Bu | O | Me | H | Oily |
| 1-119 | H | H | H | Cl | Bu-i | O | Me | H | Oily |
| 1-120 | H | H | H | Cl | Bu-s | O | Me | H | 59–62 |
| 1-121 | H | H | H | Cl | Bu-t | O | Me | H | 86–87 |
| 1-122 | H | H | H | Cl | C₅H₁₁ | O | Me | H | Oily |
| 1-123 | H | H | H | Cl | CHMePr | O | Me | H | |
| 1-124 | H | H | H | Cl | CH₂CH₂CH₂Pr-i | O | Me | H | |
| 1-125 | H | H | H | Cl | CH₂CHMeEt | O | Me | H | |
| 1-126 | H | H | H | Cl | C₆H₁₃ | O | Me | H | |

TABLE 5

| Compound No. | X¹ | X² | X³ | X⁴ | Y | G | R¹ | R² | m.p. (° C.) |
|---|---|---|---|---|---|---|---|---|---|
| 1-127 | H | H | H | Cl | C₇H₁₅ | O | Me | H | |
| 1-128 | H | H | H | Cl | C₈H₁₇ | O | Me | H | |
| 1-129 | H | H | H | Cl | C₉H₁₉ | O | Me | H | |
| 1-130 | H | H | H | Cl | C₁₀H₂₁ | O | Me | H | |
| 1-131 | H | H | H | Cl | C₃H₅-c | O | Me | H | |
| 1-132 | H | H | H | Cl | C₅H₉-c | O | Me | H | 93–96 |
| 1-133 | H | H | H | Cl | C₆H₁₁-c | O | Me | H | |
| 1-134 | H | H | H | Cl | CH₂—C₅H₉-c | O | Me | H | Oily |
| 1-135 | H | H | H | Cl | CH₂—C₆H₁₁-c | O | Me | H | |
| 1-136 | H | H | H | Cl | CH=CH₂ | O | Me | H | |
| 1-137 | H | H | H | Cl | C(Me)=CH₂ | O | Me | H | 75–78 |
| 1-138 | H | H | H | Cl | C(Me)=CHMe | O | Me | H | |
| 1-139 | H | H | H | Cl | CH₂CH=CH₂ | O | Me | H | |
| 1-140 | H | H | H | Cl | CH₂C≡CEt | O | Me | H | |
| 1-141 | H | H | H | Cl | 1-methylcyclohex-1-enyl | O | Me | H | 100–103 |
| 1-142 | H | H | H | Cl | CH(OH)Me | O | Me | H | Oily |
| 1-143 | H | H | H | Cl | CH(OH)Et | O | Me | H | |
| 1-144 | H | H | H | Cl | CH(OH)Pr | O | Me | H | |
| 1-145 | H | H | H | Cl | CH(OH)Pr-i | O | Me | H | |
| 1-146 | H | H | H | Cl | C(OH)MePr-i | O | Me | H | Oily |
| 1-147 | H | H | H | Cl | C(OH)Me₂ | O | Me | H | Oily |
| 1-148 | H | H | H | Cl | C(OH)MeEt | O | Me | H | |
| 1-149 | H | H | H | Cl | C(OH)MePr | O | Me | H | |
| 1-150 | H | H | H | Cl | C(OH)Et₂ | O | Me | H | |
| 1-151 | H | H | H | Cl | C(OH)MeBu-t | O | Me | H | |
| 1-152 | H | H | H | Cl | C(OH)MePh | O | Me | H | |
| 1-153 | H | H | H | Cl | C(OH)Et₂ | O | Me | H | Oily |
| 1-154 | H | H | H | Cl | C(OH)Ph | O | Me | H | 165–167 |
| 1-155 | H | H | H | Cl | CHClMe | O | Me | H | |
| 1-156 | H | H | H | Cl | CHClEt | O | Me | H | |
| 1-157 | H | H | H | Cl | CHClPr | O | Me | H | |
| 1-158 | H | H | H | Cl | CHCl-Pr-i | O | Me | H | |

TABLE 6

| Compound No. | X¹ | X² | X³ | X⁴ | Y | G | R¹ | R² | m.p. (° C.) |
|---|---|---|---|---|---|---|---|---|---|
| 1-159 | H | H | H | Cl | CH₂CHClMe | O | Me | H | |
| 1-160 | H | H | H | Cl | CClMe₂ | O | Me | H | Oily |
| 1-161 | H | H | H | Cl | CClMeEt | O | Me | H | |
| 1-162 | H | H | H | Cl | CHClCH₂CHMe₂ | O | Me | H | Oily |
| 1-163 | H | H | H | Cl | CClMeBu-t | O | Me | H | |
| 1-164 | H | H | H | Cl | CClEt₂ | O | Me | H | |
| 1-165 | H | H | H | Cl | CClMePh | O | Me | H | |
| 1-166 | H | H | H | Cl | CHClPh | O | Me | H | |
| 1-167 | H | H | H | Cl | CHBrMe | O | Me | H | 85–87 |
| 1-168 | H | H | H | Cl | CH₂OMe | O | Me | H | Oily |
| 1-169 | H | H | H | Cl | CH(OMe)Me | O | Me | H | 59–62 |
| 1-170 | H | H | H | Cl | CH(OMe)Et | O | Me | H | |
| 1-171 | H | H | H | Cl | CH(OMe)Pr | O | Me | H | |
| 1-172 | H | H | H | Cl | CH(OMe)Pr-i | O | Me | H | |
| 1-173 | H | H | H | Cl | CH₂CH(OMe)Me | O | Me | H | |
| 1-174 | H | H | H | Cl | C(OMe)Me₂ | O | Me | H | Oily |
| 1-175 | H | H | H | Cl | C(OMe)MeEt | O | Me | H | |
| 1-176 | H | H | H | Cl | C(OMe)MePr | O | Me | H | |
| 1-177 | H | H | H | Cl | C(OMe)MeBu-t | O | Me | H | |
| 1-178 | H | H | H | Cl | C(OMe)Et₂ | O | Me | H | Oily |
| 1-179 | H | H | H | Cl | C(OMe)MePh | O | Me | H | |
| 1-180 | H | H | H | Cl | CH(OMe)Ph | O | Me | H | |
| 1-181 | H | H | H | Cl | 1-methylcyclopentan-1-ol | O | Me | H | Oily |
| 1-182 | H | H | H | Cl | 1-methylcyclohexan-1-ol | O | Me | H | |
| 1-183 | H | H | H | Cl | 1-methylcyclopent-1-enyl | O | Me | H | 75–78 |
| 1-184 | H | H | H | Cl | SiMe₃ | O | Me | H | Oily |
| 1-185 | H | H | H | Cl | SiEt₃ | O | Me | H | |
| 1-186 | H | H | H | Cl | CF₃ | O | Me | H | 93–96 |
| 1-187 | H | H | H | Cl | COMe | O | Me | H | 82–85 |
| 1-188 | H | H | H | Cl | COOMe | O | Me | H | 92–95 |
| 1-189 | H | H | H | Cl | COOEt | O | Me | H | |

TABLE 7

| Compound No. | X¹ | X² | X³ | X⁴ | Y | G | R¹ | R² | m.p. (° C.) |
|---|---|---|---|---|---|---|---|---|---|
| 1-190 | H | H | H | Cl | COOH | O | Me | H | 151–154 |
| 1-191 | H | H | H | Br | H | O | Me | H | |
| 1-192 | H | H | H | Br | Me | O | Me | H | |
| 1-193 | H | H | H | Br | Et | O | Me | H | |
| 1-194 | H | H | H | Br | Pr | O | Me | H | |
| 1-195 | H | H | H | Br | Pr-i | O | Me | H | |
| 1-196 | H | H | H | Br | Bu | O | Me | H | |
| 1-197 | H | H | H | Br | Bu-i | O | Me | H | |

TABLE 7-continued

| Compound No. | $X^1$ | $X^2$ | $X^3$ | $X^4$ | Y | G | $R^1$ | $R^2$ | m.p. (° C.) |
|---|---|---|---|---|---|---|---|---|---|
| 1-198 | H | H | H | Br | Bu-s | O | Me | H | |
| 1-199 | H | H | H | Br | Bu-t | O | Me | H | 103–104 |
| 1-200 | H | H | H | Br | $C_5H_{11}$ | O | Me | H | |
| 1-201 | H | H | H | Br | CHMePr | O | Me | H | |
| 1-202 | H | H | H | Br | $(CH_2)_3Pr$-i | O | Me | H | |
| 1-203 | H | H | H | Br | $CH_2CH(Me)CH_2Me$ | O | Me | H | |
| 1-204 | H | H | H | Br | $C_6H_{13}$ | O | Me | H | |
| 1-205 | H | H | H | Br | $C_7H_{15}$ | O | Me | H | |
| 1-206 | H | H | H | Br | $C_8H_{17}$ | O | Me | H | |
| 1-207 | H | H | H | Br | $C_9H_{19}$ | O | Me | H | |
| 1-208 | H | H | H | Br | $C_{10}H_{21}$ | O | Me | H | |
| 1-209 | H | H | H | Br | $C_3H_5$-c | O | Me | H | |
| 1-210 | H | H | H | Br | $C_5H_9$-c | O | Me | H | |
| 1-211 | H | H | H | Br | $C_6H_{11}$-c | O | Me | H | |
| 1-212 | H | H | H | Br | $CH_2$—$C_5H_9$-c | O | Me | H | |
| 1-213 | H | H | H | Br | $CH_2$—$C_6H_{11}$-c | O | Me | H | |
| 1-214 | H | H | H | Br | $CH=CH_2$ | O | Me | H | |
| 1-215 | H | H | H | Br | $C(Me)=CH_2$ | O | Me | H | |
| 1-216 | H | H | H | Br | $C(Me)=CHMe$ | O | Me | H | |
| 1-217 | H | H | H | Br | $CH_2CH=CH_2$ | O | Me | H | |
| 1-218 | H | H | H | Br | $CH_2C≡CEt$ | O | Me | H | |
| 1-219 | H | H | H | Br | 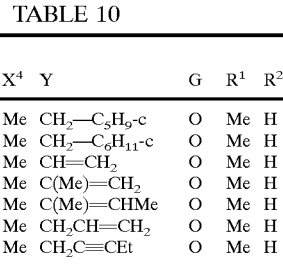 | O | Me | H | |
| 1-220 | H | H | H | Br | CH(OH)Me | O | Me | H | |
| 1-221 | H | H | H | Br | CH(OH)Et | O | Me | H | |

TABLE 8

| Compound No. | $X^1$ | $X^2$ | $X^3$ | $X^4$ | Y | G | $R^1$ | $R^2$ | m.p. (° C.) |
|---|---|---|---|---|---|---|---|---|---|
| 1-222 | H | H | H | Br | CH(OH)Pr | O | Me | H | |
| 1-223 | H | H | H | Br | CH(OH)Pr-i | O | Me | H | |
| 1-224 | H | H | H | Br | $CH_2CH(OH)Me$ | O | Me | H | |
| 1-225 | H | H | H | Br | $C(OH)Me_2$ | O | Me | H | |
| 1-226 | H | H | H | Br | C(OH)MeEt | O | Me | H | |
| 1-227 | H | H | H | Br | C(OH)MePr | O | Me | H | |
| 1-228 | H | H | H | Br | $C(OH)Et_2$ | O | Me | H | |
| 1-229 | H | H | H | Br | C(OH)MeBu-t | O | Me | H | |
| 1-230 | H | H | H | Br | C(OH)MePh | O | Me | H | |
| 1-231 | H | H | H | Br | CH(OH)Ph | O | Me | H | |
| 1-232 | H | H | H | Br | CHClMe | O | Me | H | |
| 1-233 | H | H | H | Br | CHClEt | O | Me | H | |
| 1-234 | H | H | H | Br | CHClPr | O | Me | H | |
| 1-235 | H | H | H | Br | CHClPr-i | O | Me | H | |
| 1-236 | H | H | H | Br | $CH_2CHClMe$ | O | Me | H | |
| 1-237 | H | H | H | Br | $CClMe_2$ | O | Me | H | |
| 1-238 | H | H | H | Br | CClMeEt | O | Me | H | |
| 1-239 | H | H | H | Br | CClMePr | O | Me | H | |
| 1-240 | H | H | H | Br | $CClEt_2$ | O | Me | H | |
| 1-241 | H | H | H | Br | CClMeBu-t | O | Me | H | |
| 1-242 | H | H | H | Br | CClMePh | O | Me | H | |
| 1-243 | H | .H | H | Br | CHClPh | O | Me | H | |
| 1-244 | H | H | H | Br | CH(OMe)Me | O | Me | H | |
| 1-245 | H | H | H | Br | CH(OMe)Et | O | Me | H | |
| 1-246 | H | H | H | Br | CH(OMe)Pr | O | Me | H | |
| 1-247 | H | H | H | Br | CH(OMe)Pr-i | O | Me | H | |
| 1-248 | H | H | H | Br | $CH_2CH(OMe)Me$ | O | Me | H | |
| 1-249 | H | H | H | Br | $C(OMe)Me_2$ | O | Me | H | |
| 1-250 | H | H | H | Br | C(QMe)MeEt | O | Me | H | |
| 1-251 | H | H | H | Br | C(OMe)MePr | O | Me | H | |
| 1-252 | H | H | H | Br | C(OMe)MeBu-t | O | Me | H | |
| 1-253 | H | H | H | Br | $C(OMe)Et_2$ | O | Me | H | |
| 1-254 | H | H | H | Br | C(OMe)MePh | O | Me | H | |
| 1-255 | H | H | H | Br | CH(OMe)Ph | O | Me | H | |

TABLE 9

| Compound No. | $X^1$ | $X^2$ | $X^3$ | $X^4$ | Y | G | $R^1$ | $R^2$ | m.p. (° C.) |
|---|---|---|---|---|---|---|---|---|---|
| 1-256 | H | H | H | Br | 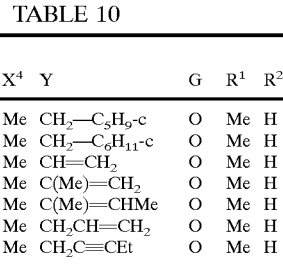 | O | Me | H | |
| 1-257 | H | H | H | Br | | O | Me | H | |
| 1-258 | H | H | H | Br | $SiMe_3$ | O | Me | H | |
| 1-259 | H | H | H | Br | $SiEt_3$ | O | Me | H | |
| 1-260 | H | H | H | Br | $CH_2Ph$ | O | Me | H | |
| 1-261 | H | H | H | Br | $CF_3$ | O | Me | H | |
| 1-262 | H | H | H | Br | COMe | O | Me | H | |
| 1-263 | H | H | H | Br | COOMe | O | Me | H | |
| 1-264 | H | H | H | Br | COOEt | O | Me | H | |
| 1-265 | H | H | H | Br | COOH | O | Me | H | |
| 1-266 | H | H | H | Me | H | O | Me | H | Oily |
| 1-267 | H | H | H | Me | Me | O | Me | H | |
| 1-268 | H | H | H | Me | Et | O | Me | H | |
| 1-269 | H | H | H | Me | Pr | O | Me | H | |
| 1-270 | H | H | H | Me | Pr-i | O | Me | H | |
| 1-271 | H | H | H | Me | Bu | O | Me | H | |
| 1-272 | H | H | H | Me | Bu-i | O | Me | H | |
| 1-273 | H | H | H | Me | Bu-s | O | Me | H | |
| 1-274 | H | H | H | Me | Bu-t | O | Me | H | Oily |
| 1-275 | H | H | H | Me | $C_5H_{11}$ | O | Me | H | |
| 1-276 | H | H | H | Me | CHMePr | O | Me | H | |
| 1-277 | H | H | H | Me | $CH_2CH_2CH_2Pr$-i | O | Me | H | |
| 1-278 | H | H | H | Me | $CH_2CH(Me)CH_2Me$ | O | Me | H | |
| 1-279 | H | H | H | Me | $C_6H_{13}$ | O | Me | H | |
| 1-280 | H | H | H | Me | $C_7H_{15}$ | O | Me | H | |
| 1-281 | H | H | H | Me | $C_8H_{17}$ | O | Me | H | |
| 1-282 | H | H | H | Me | $C_9H_{19}$ | O | Me | H | |
| 1-283 | H | H | H | Me | $C_{10}H_{21}$ | O | Me | H | |
| 1-284 | H | H | H | Me | $C_3H_5$-c | O | Me | H | |
| 1-285 | H | H | H | Me | $C_5H_9$-c | O | Me | H | |
| 1-286 | H | H | H | Me | $C_6H_{11}$-c | O | Me | H | |

TABLE 10

| Compound No. | $X^1$ | $X^2$ | $X^3$ | $X^4$ | Y | G | $R^1$ | $R^2$ | m.p. (° C.) |
|---|---|---|---|---|---|---|---|---|---|
| 1-287 | H | H | H | Me | $CH_2$—$C_5H_9$-c | O | Me | H | |
| 1-288 | H | H | H | Me | $CH_2$—$C_6H_{11}$-c | O | Me | H | |
| 1-289 | H | H | H | Me | $CH=CH_2$ | O | Me | H | |
| 1-290 | H | H | H | Me | $C(Me)=CH_2$ | O | Me | H | |
| 1-291 | H | H | H | Me | $C(Me)=CHMe$ | O | Me | H | |
| 1-292 | H | H | H | Me | $CH_2CH=CH_2$ | O | Me | H | |
| 1-293 | H | H | H | Me | $CH_2C≡CEt$ | O | Me | H | |
| 1-294 | H | H | H | Me | | O | Me | H | |
| 1-295 | H | H | H | Me | CH(OH)Me | O | Me | H | |
| 1-296 | H | H | H | Me | CH(OH)Et | O | Me | H | |
| 1-297 | H | H | H | Me | CH(OH)Pr | O | Me | H | |
| 1-298 | H | H | H | Me | CH(OH)Pr-i | O | Me | H | |
| 1-299 | H | H | H | Me | $CH_2CH(OH)Me$ | O | Me | H | |
| 1-300 | H | H | H | Me | $C(OH)Me_2$ | O | Me | H | |

TABLE 10-continued

| Compound No. | $X^1$ | $X^2$ | $X^3$ | $X^4$ | Y | G | $R^1$ | $R^2$ | m.p. (° C.) |
|---|---|---|---|---|---|---|---|---|---|
| 1-301 | H | H | H | Me | C(OH)MeEt | O | Me | H | |
| 1-302 | H | H | H | Me | C(OH)MePr | O | Me | H | |
| 1-303 | H | H | H | Me | C(OH)Et$_2$ | O | Me | H | |
| 1-304 | H | H | H | Me | C(OH)MeBu-t | O | Me | H | |
| 1-305 | H | H | H | Me | C(OH)MePh | O | Me | H | |
| 1-306 | H | H | H | Me | CH(OH)Ph | O | Me | H | |
| 1-307 | H | H | H | Me | CHClMe | O | Me | H | |
| 1-308 | H | H | H | Me | CHClEt | O | Me | H | |
| 1-309 | H | H | H | Me | CHClPr | O | Me | H | |
| 1-310 | H | H | H | Me | CHClPr-i | O | Me | H | |
| 1-311 | H | H | H | Me | CH$_2$CHClMe | O | Me | H | |
| 1-312 | H | H | H | Me | CClMe$_2$ | O | Me | H | |
| 1-313 | H | H | H | Me | CClMeEt | O | Me | H | |
| 1-314 | H | H | H | Me | CClMePr | O | Me | H | |
| 1-315 | H | H | H | Me | CClEt$_2$ | O | Me | H | |
| 1-316 | H | H | H | Me | CClMeBu-t | O | Me | H | |
| 1-317 | H | H | H | Me | CClMePh | O | Me | H | |
| 1-318 | H | H | H | Me | CHClPh | O | Me | H | |
| 1-319 | H | H | H | Me | CH(OMe)Me | O | Me | H | |

TABLE 11

| Compound No. | $X^1$ | $X^2$ | $X^3$ | $X^4$ | Y | G | $R^1$ | $R^2$ | m.p. (° C.) |
|---|---|---|---|---|---|---|---|---|---|
| 1-320 | H | H | H | Me | CH(OMe)Et | O | Me | H | |
| 1-321 | H | H | H | Me | CH(OMe)Pr | O | Me | H | |
| 1-322 | H | H | H | Me | CH(OMe)Pr-i | O | Me | H | |
| 1-323 | H | H | H | Me | CH$_2$CH(OMe)Me | O | Me | H | |
| 1-324 | H | H | H | Me | C(OMe)Me$_2$ | O | Me | H | |
| 1-325 | H | H | H | Me | C(OMe)MeEt | O | Me | H | |
| 1-326 | H | H | H | Me | C(OMe)MePr | O | Me | H | |
| 1-327 | H | H | H | Me | C(OMe)MeBu-t | O | Me | H | |
| 1-328 | H | H | H | Me | C(OMe)Et$_2$ | O | Me | H | |
| 1-329 | H | H | H | Me | C(OMe)MePh | O | Me | H | |
| 1-330 | H | H | H | Me | CH(OMe)Ph | O | Me | H | |
| 1-331 | H | H | H | Me | 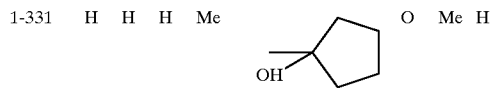 | O | Me | H | |
| 1-332 | H | H | H | Me | 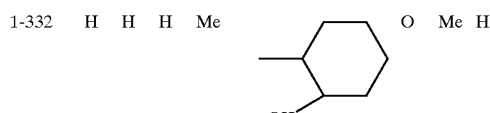 | O | Me | H | |
| 1-333 | H | H | H | Me | SiMe$_3$ | O | Me | H | Oily |
| 1-334 | H | H | H | Me | SiEt$_3$ | O | Me | H | |
| 1-335 | H | H | H | Me | CH$_2$Ph | O | Me | H | |
| 1-336 | H | H | H | Me | CF$_3$ | O | Me | H | |
| 1-337 | H | H | H | Me | COMe | O | Me | H | |
| 1-338 | H | H | H | Me | COOMe | O | Me | H | |
| 1-339 | H | H | H | Me | COOEt | O | Me | H | |
| 1-340 | H | H | H | Me | COOH | O | Me | H | |
| 1-341 | H | H | H | OMe | H | O | Me | H | 92–95 |
| 1-342 | H | H | H | OMe | Me | O | Me | H | |
| 1-343 | H | H | H | OMe | Et | O | Me | H | |
| 1-344 | H | H | H | OMe | Pr | O | Me | H | |
| 1-345 | H | H | H | OMe | Pr-i | O | Me | H | |
| 1-346 | H | H | H | OMe | Bu | O | Me | H | |
| 1-347 | H | H | H | OMe | Bu-i | O | Me | H | |
| 1-348 | H | H | H | OMe | Bu-s | O | Me | H | |
| 1-349 | H | H | H | OMe | Bu-t | O | Me | H | Oily |
| 1-350 | H | H | H | OMe | C$_5$H$_{11}$ | O | Me | H | |
| 1-351 | H | H | H | OMe | CH(Me)Pr | O | Me | H | |
| 1-352 | H | H | H | OMe | (CH$_2$)$_3$Pr-i | O | Me | H | |

TABLE 12

| Compound No. | $X^1$ | $X^2$ | $X^3$ | $X^4$ | Y | G | $R^1$ | $R^2$ | m.p. (° C.) |
|---|---|---|---|---|---|---|---|---|---|
| 1-353 | H | H | H | OMe | CH$_2$CH(Me)CH$_2$Me | O | Me | H | |
| 1-354 | H | H | H | OMe | C$_6$H$_{13}$ | O | Me | H | |
| 1-355 | H | H | H | OMe | C$_3$H$_5$-c | O | Me | H | |
| 1-356 | H | H | H | OMe | C$_5$H$_9$-c | O | Me | H | |
| 1-357 | H | H | H | OMe | C$_6$H$_{11}$-c | O | Me | H | |
| 1-358 | H | H | H | OMe | CH$_2$—C$_5$H$_9$-c | O | Me | H | |
| 1-359 | H | H | H | OMe | CH$_2$—C$_6$H$_{11}$-c | O | Me | H | |
| 1-360 | H | H | H | OMe | CH=CH$_2$ | O | Me | H | |
| 1-361 | H | H | H | OMe | C(Me)=CH$_2$ | O | Me | H | |
| 1-362 | H | H | H | OMe | C(Me)=CHMe | O | Me | H | |
| 1-363 | H | H | H | OMe | CH$_2$CH=CH$_2$ | O | Me | H | |
| 1-364 | H | H | H | OMe | CH$_2$C≡CEt | O | Me | H | |
| 1-365 | H | H | H | OMe |  | O | Me | H | |
| 1-366 | H | H | H | OMe | CH(OH)Me | O | Me | H | |
| 1-367 | H | H | H | OMe | CH(OH)Et | O | Me | H | |
| 1-368 | H | H | H | OMe | CH(OH)Pr | O | Me | H | |
| 1-369 | H | H | H | OMe | CH(OH)Pr-i | O | Me | H | |
| 1-370 | H | H | H | OMe | CH$_2$CH(OH)Me | O | Me | H | |
| 1-371 | H | H | H | OMe | C(OH)Me$_2$ | O | Me | H | |
| 1-372 | H | H | H | OMe | C(OH)MeEt | O | Me | H | |
| 1-373 | H | H | H | OMe | C(OH)MePr | O | Me | H | |
| 1-374 | H | H | H | OMe | C(OH)MeBu-t | O | Me | H | |
| 1-375 | H | H | H | OMe | C(OH)Et$_2$ | O | Me | H | |
| 1-376 | H | H | H | OMe | C(OH)MePh | O | Me | H | |
| 1-377 | H | H | H | OMe | CH(OH)Ph | O | Me | H | |
| 1-378 | H | H | H | OMe | CHClMe | O | Me | H | |
| 1-379 | H | H | H | OMe | CHClEt | O | Me | H | |
| 1-380 | H | H | H | OMe | CHClPr | O | Me | H | |
| 1-381 | H | H | H | OMe | CHClPr-i | O | Me | H | |
| 1-382 | H | H | H | OMe | CH$_2$CHClMe | O | Me | H | |
| 1-383 | H | H | H | OMe | CClMe$_2$ | O | Me | H | |
| 1-384 | H | H | H | OMe | CClMeEt | O | Me | H | |

TABLE 13

| Compound No. | $X^1$ | $X^2$ | $X^3$ | $X^4$ | Y | G | $R^1$ | $R^2$ | m.p. (° C.) |
|---|---|---|---|---|---|---|---|---|---|
| 1-385 | H | H | H | OMe | CClMePr | O | Me | H | |
| 1-386 | H | H | H | OMe | CClEt$_2$ | O | Me | H | |
| 1-387 | H | H | H | OMe | CClMeBu-t | O | Me | H | |
| 1-388 | H | H | H | OMe | CClMePh | O | Me | H | |
| 1-389 | H | H | H | OMe | CHClPh | O | Me | H | |
| 1-390 | H | H | H | OMe | CH(OMe)Me | O | Me | H | |
| 1-391 | H | H | H | OMe | CH(OMe)Et | O | Me | H | |
| 1-392 | H | H | H | OMe | CH(OMe)Pr | O | Me | H | |
| 1-393 | H | H | H | OMe | CH(OMe)Pr-i | O | Me | H | |
| 1-394 | H | H | H | OMe | CH$_2$CH(OMe)Me | O | Me | H | |
| 1-395 | H | H | H | OMe | C(OMe)Me$_2$ | O | Me | H | |
| 1-396 | H | H | H | OMe | C(OMe)MeEt | O | Me | H | |
| 1-397 | H | H | H | OMe | C(OMe)MePr | O | Me | H | |
| 1-398 | H | H | H | OMe | C(OMe)Et$_2$ | O | Me | H | |
| 1-399 | H | H | H | OMe | C(OMe)MeBu-t | O | Me | H | |
| 1-400 | H | H | H | OMe | C(OMe)MePh | O | Me | H | |
| 1-401 | H | H | H | OMe | CH(OMe)Ph | O | Me | H | |
| 1-402 | H | H | H | OMe | 1-hydroxy-1-methylcyclopentyl | O | Me | H | |
| 1-403 | H | H | H | OMe | 1-hydroxy-1-methylcyclohexyl | O | Me | H | |
| 1-404 | H | H | H | OMe | SiMe$_3$ | O | Me | H | Oily |
| 1-405 | H | H | H | OMe | SiEt$_3$ | O | Me | H | |
| 1-406 | H | H | H | OMe | CH$_2$—Ph | O | Me | H | |
| 1-407 | H | H | H | OMe | CF$_3$ | O | Me | H | |
| 1-408 | H | H | H | OMe | COMe | O | Me | H | |
| 1-409 | H | H | H | OMe | COOMe | O | Me | H | |
| 1-410 | H | H | H | OMe | COOEt | O | Me | H | |
| 1-411 | H | H | H | OMe | COOH | O | Me | H | |
| 1-412 | H | H | H | OCHF$_2$ | H | O | Me | H | |
| 1-413 | H | H | H | OCHF$_2$ | Me | O | Me | H | |
| 1-414 | H | H | H | OCHF$_2$ | Et | O | Me | H | |
| 1-415 | H | H | H | OCHF$_2$ | Pr | O | Me | H | |
| 1-416 | H | H | H | OCHF$_2$ | Pr-i | O | Me | H | |

TABLE 14

| Compound No. | $X^1$ | $X^2$ | $X^3$ | $X^4$ | Y | G | $R^1$ | $R^2$ | m.p. (° C.) |
|---|---|---|---|---|---|---|---|---|---|
| 1-417 | H | H | H | OCHF$_2$ | Bu | O | Me | H | |
| 1-418 | H | H | H | OCHF$_2$ | Bu-i | O | Me | H | |
| 1-419 | H | H | H | OCHF$_2$ | Bu-s | O | Me | H | |
| 1-420 | H | H | H | OCHF$_2$ | Bu-t | O | Me | H | |
| 1-421 | H | H | H | OCHF$_2$ | C$_5$H$_{11}$ | O | Me | H | |
| 1-422 | H | H | H | OCHF$_2$ | CHMePr | O | Me | H | |
| 1-423 | H | H | H | OCHF$_2$ | CH$_2$C$_2$CH$_2$Pr-i | O | Me | H | |
| 1-424 | H | H | H | OCHF$_2$ | CH$_2$CH(Me)CH$_2$Me | O | Me | H | |
| 1-425 | H | H | H | OCHF$_2$ | C$_6$H$_{13}$ | O | Me | H | |
| 1-426 | H | H | H | OCHF$_2$ | C$_3$H$_5$-c | O | Me | H | |
| 1-427 | H | H | H | OCHF$_2$ | C$_5$H$_9$-c | O | Me | H | |
| 1-428 | H | H | H | OCHF$_2$ | C$_6$H$_{11}$-c | O | Me | H | |
| 1-429 | H | H | H | OCHF$_2$ | CH$_2$—C$_5$H$_9$-c | O | Me | H | |
| 1-430 | H | H | H | OCHF$_2$ | CH$_2$—C$_6$H$_{11}$-c | O | Me | H | |
| 1-431 | H | H | H | OCHF$_2$ | CH=CH$_2$ | O | Me | H | |
| 1-432 | H | H | H | OCHF$_2$ | C(Me)=CH$_2$ | O | Me | H | |
| 1-433 | H | H | H | OCHF$_2$ | C(Me)=CHMe | O | Me | H | |
| 1-434 | H | H | H | OCHF$_2$ | CH$_2$CH=CH$_2$ | O | Me | H | |
| 1-435 | H | H | H | OCHF$_2$ | 1-methylcyclohexenyl | O | Me | H | |
| 1-436 | H | H | H | OCHF$_2$ | CH(OH)Me | O | Me | H | |
| 1-437 | H | H | H | OCHF$_2$ | CH(OH)Et | O | Me | H | |

TABLE 14-continued

| Compound No. | X¹ | X² | X³ | X⁴ | Y | G | R¹ | R² | m.p. (° C.) |
|---|---|---|---|---|---|---|---|---|---|
| 1-438 | H | H | H | OCHF$_2$ | CH(OH)Pr | O | Me | H | |
| 1-439 | H | H | H | OCHF$_2$ | CH(OH)Pr-i | O | Me | H | |
| 1-440 | H | H | H | OCHF$_2$ | CH$_2$CH(OH)Me | O | Me | H | |
| 1-441 | H | H | H | OCHF$_2$ | C(OH)Me$_2$ | O | Me | H | |
| 1-442 | H | H | H | OCHF$_2$ | C(OH)MeEt | O | Me | H | |
| 1-443 | H | H | H | OCHF$_2$ | C(OH)MePr | O | Me | H | |
| 1-444 | H | H | H | OCHF$_2$ | C(OH)MeBu-t | O | Me | H | |

TABLE 15

| Compound No. | X¹ | X² | X³ | X⁴ | Y | G | R¹ | R² | m.p. (° C.) |
|---|---|---|---|---|---|---|---|---|---|
| 1-445 | H | H | H | OCHF$_2$ | C(OH)Et$_2$ | O | Me | H | |
| 1-446 | H | H | H | OCHF$_2$ | C(OH)MePh | O | Me | H | |
| 1-447 | H | H | H | OCHF$_2$ | CH(OH)Ph | O | Me | H | |
| 1-448 | H | H | H | OCHF$_2$ | CHClMe | O | Me | H | |
| 1-449 | H | H | H | OCHF$_2$ | CHClEt | O | Me | H | |
| 1-450 | H | H | H | OCHF$_2$ | CHClPr | O | Me | H | |
| 1-451 | H | H | H | OCHF$_2$ | CHClPr-i | O | Me | H | |
| 1-452 | H | H | H | OCHF$_2$ | CH$_2$CHClMe | O | Me | H | |
| 1-453 | H | H | H | GCHF$_2$ | CClMe$_2$ | O | Me | H | |
| 1-454 | H | H | H | OCHF$_2$ | CClMeEt | O | Me | H | |
| 1-455 | H | H | H | OCHF$_2$ | CClMePr | O | Me | H | |
| 1-456 | H | H | H | OCHF$_2$ | CClEt$_2$ | O | Me | H | |
| 1-457 | H | H | H | OCHF$_2$ | CClMeBu-t | O | Me | H | |
| 1-458 | H | H | H | OCHF$_2$ | CClMePh | O | Me | H | |
| 1-459 | H | H | H | OCHF$_2$ | CHClPh | O | Me | H | |
| 1-460 | H | H | H | OCHF$_2$ | CH(OMe)Me | O | Me | H | |
| 1-461 | H | H | H | OCHF$_2$ | CH(OMe)Et | O | Me | H | |
| 1-462 | H | H | H | OCHF$_2$ | CH(OMe)Pr | O | Me | H | |
| 1-463 | H | H | H | OCHF$_2$ | CH(OMe)Pr-i | O | Me | H | |
| 1-464 | H | H | H | OCHF$_2$ | CH$_2$CH(OMe)Me | O | Me | H | |
| 1-465 | H | H | H | OCHF$_2$ | C(OMe)Me$_2$ | O | Me | H | |
| 1-466 | H | H | H | OCHF$_2$ | C(OMe)MeEt | O | Me | H | |
| 1-467 | H | H | H | OCHF$_2$ | C(OMe)MePr | O | Me | H | |
| 1-468 | H | H | H | OCHF$_2$ | C(OMe)Et$_2$ | O | Me | H | |
| 1-469 | H | H | H | OCHF$_2$ | C(OMe)MeBu-t | O | Me | H | |
| 1-470 | H | H | H | OCHF$_2$ | C(OMe)MePh | O | Me | H | |
| 1-471 | H | H | H | OCHF$_2$ | CH(OMe)Ph | O | Me | H | |
| 1-472 | H | H | H | OCHF$_2$ | 1-hydroxycyclopentyl | O | Me | H | |

TABLE 16

| Compound No. | X¹ | X² | X³ | X⁴ | Y | G | R¹ | R² | m.p. (° C.) |
|---|---|---|---|---|---|---|---|---|---|
| 1-473 | H | H | H | OCHF$_2$ | 1-hydroxycyclohexyl | O | Me | H | |
| 1-474 | H | H | H | OCHF$_2$ | SiMe$_3$ | O | Me | H | |
| 1-475 | H | H | H | OCHF$_2$ | SiEt$_3$ | O | Me | H | |
| 1-476 | H | H | H | OCHF$_2$ | CH$_2$—Ph | O | Me | H | |
| 1-477 | H | H | H | OCHF$_2$ | CF$_3$ | O | Me | H | |
| 1-478 | H | H | H | OCHF$_2$ | COMe | O | Me | H | |
| 1-479 | H | H | H | OCHF$_2$ | COOMe | O | Me | H | |
| 1-480 | H | H | H | OCHF$_2$ | COOEt | O | Me | H | |
| 1-481 | H | H | H | OCHF$_2$ | COOH | O | Me | H | |
| 1-482 | H | H | H | CF$_3$ | H | O | Me | H | |
| 1-483 | H | H | H | CF$_3$ | Me | O | Me | H | |
| 1-484 | H | H | H | CF$_3$ | Et | O | Me | H | |
| 1-485 | H | H | H | CF$_3$ | Pr | O | Me | H | |
| 1-486 | H | H | H | CF$_3$ | Pr-i | O | Me | H | |
| 1-487 | H | H | H | CF$_3$ | Bu | O | Me | H | |
| 1-488 | H | H | H | CF$_3$ | Bu-i | O | Me | H | |
| 1-489 | H | H | H | CF$_3$ | Bu-s | O | Me | H | |
| 1-490 | H | H | H | CF$_3$ | Bu-t | O | Me | H | |
| 1-491 | H | H | H | CF$_3$ | C$_5$H$_{11}$ | O | Me | H | |

TABLE 16-continued

| Compound No. | X¹ | X² | X³ | X⁴ | Y | G | R¹ | R² | m.p. (° C.) |
|---|---|---|---|---|---|---|---|---|---|
| 1-492 | H | H | H | CF₃ | CHMePr | O | Me | H | |
| 1-493 | H | H | H | CF₃ | CH₂C₂CH₂Pr-i | O | Me | H | |
| 1-494 | H | H | H | CF₃ | CH₂CH(Me)CH₂Me | O | Me | H | |
| 1-495 | H | H | H | CF₃ | C₆H₁₃ | O | Me | H | |
| 1-496 | H | H | H | CF₃ | C₃H₅-c | O | Me | H | |
| 1-497 | H | H | H | CF₃ | C₅H₉-c | O | Me | H | |
| 1-498 | H | H | H | CF₃ | CH=CH₂ | O | Me | H | |
| 1-499 | H | H | H | CF₃ | C(Me)=CH₂ | O | Me | H | |
| 1-500 | H | H | H | CF₃ | C(Me)=CHMe | O | Me | H | |

TABLE 17

| Compound No. | X¹ | X² | X³ | X⁴ | Y | G | R¹ | R² | m.p. (° C.) |
|---|---|---|---|---|---|---|---|---|---|
| 1-501 | H | H | H | CF₃ | CH₂CH=CH₂ | O | Me | H | |
| 1-502 | H | H | H | CF₃ | 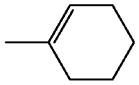 | O | Me | H | |
| 1-503 | H | H | H | CF₃ | CHClMe | O | Me | H | |
| 1-504 | H | H | H | CF₃ | CHClEt | O | Me | H | |
| 1-505 | H | H | H | CF₃ | CHClPi | O | Me | H | |
| 1-506 | H | H | H | CF₃ | CHClPr-i | O | Me | H | |
| 1-507 | H | H | H | CF₃ | CH₂CHClMe | O | Me | H | |
| 1-508 | H | H | H | CF₃ | CClMe₂ | O | Me | H | |
| 1-509 | H | H | H | CF₃ | CClMeEt | O | Me | H | |
| 1-510 | H | H | H | CF₃ | CClMePr | O | Me | H | |
| 1-511 | H | H | H | CF₃ | CClMeBu-t | O | Me | H | |
| 1-512 | H | H | H | CF₃ | CClMePh | O | Me | H | |
| 1-513 | H | H | H | CF₃ | CHClPh | O | Me | H | |
| 1-514 | H | H | H | CF₃ | CH(OMe)Me | O | Me | H | |
| 1-515 | H | H | H | CF₃ | CH(OMe)Et | O | Me | H | |
| 1-516 | H | H | H | CF₃ | CH(OMe)Pr | O | Me | H | |
| 1-517 | H | H | H | CF₃ | CH(OMe)Pr-i | O | Me | H | |
| 1-518 | H | H | H | CF₃ | CH₂CH(OMe)Me | O | Me | H | |
| 1-519 | H | H | H | CF₃ | C(OMe)Me₂ | O | Me | H | |
| 1-520 | H | H | H | CF₃ | C(OMe)MeEt | O | Me | H | |
| 1-521 | H | H | H | CF₃ | C(OMe)MePr | O | Me | H | |
| 1-522 | H | H | H | CF₃ | C(OMe)MeBu-t | O | Me | H | |
| 1-523 | H | H | H | CF₃ | C(OMe)MePh | O | Me | H | |
| 1-524 | H | H | H | CF₃ | CH(OMe)Ph | O | Me | H | |
| 1-525 | H | H | H | CF₃ | SiMe₃ | O | Me | H | |
| 1-526 | H | H | H | CF₃ | SiEt₃ | O | Me | H | |
| 1-527 | H | H | H | CF₃ | CH₂Ph | O | Me | H | |
| 1-528 | H | H | H | CF₃ | CF₃ | O | Me | H | |

TABLE 18

| Compound No. | X¹ | X² | X³ | X⁴ | Y | G | R¹ | R² | m.p. (° C.) |
|---|---|---|---|---|---|---|---|---|---|
| 1-529 | H | H | H | CF₃ | COMe | O | Me | H | |
| 1-530 | H | H | H | CF₃ | COOMe | O | Me | H | |
| 1-531 | H | H | Me | H | H | O | Me | H | |
| 1-532 | H | H | Me | H | Me | O | Me | H | |
| 1-533 | H | H | Me | H | Et | O | Me | H | |
| 1-534 | H | H | Me | H | Pr | O | Me | H | |
| 1-535 | H | H | Me | H | Pr-i | O | Me | H | |
| 1-536 | H | H | Me | H | Bu | O | Me | H | |
| 1-537 | H | H | Me | H | Bu-i | O | Me | H | |
| 1-538 | H | H | Me | H | Bu-s | O | Me | H | |
| 1-539 | H | H | Me | H | Bu-t | O | Me | H | Oily |
| 1-540 | H | H | Me | H | C₅H₁₁ | O | Me | H | |
| 1-541 | H | H | Me | H | CH(Me)Pr | O | Me | H | |
| 1-542 | H | H | Me | H | C₆H₁₃ | O | Me | H | |

TABLE 18-continued

| Compound No. | X¹ | X² | X³ | X⁴ | Y | G | R¹ | R² | m.p. (° C.) |
|---|---|---|---|---|---|---|---|---|---|
| 1-543 | H | H | Me | H | C₃H₅-c | O | Me | H | |
| 1-544 | H | H | Me | H | C₅H₉-c | O | Me | H | |
| 1-545 | H | H | Me | H | CH=CH₂ | O | Me | H | |
| 1-546 | H | H | Me | H | C(Me)=CH₂ | O | Me | H | |
| 1-547 | H | H | Me | H | C(Me)=CHMe | O | Me | H | |
| 1-548 | H | H | Me | H | CHClMe | O | Me | H | |
| 1-549 | H | H | Me | H | CHClEt | O | Me | H | |
| 1-550 | H | H | Me | H | CHClPr | O | Me | H | |
| 1-551 | H | H | Me | H | CH₂CHClMe | Q | Me | H | |
| 1-552 | H | H | Me | H | CClMe₂ | O | Me | H | |
| 1-553 | H | H | Me | H | CClMeEt | O | Me | H | |
| 1-554 | H | H | Me | H | CClMePr | O | Me | H | |
| 1-555 | H | H | Me | H | CClMeBu-t | O | Me | H | |
| 1-556 | H | H | Me | H | CClMePh | O | Me | H | |
| 1-557 | H | H | Me | H | CHClPh | O | Me | H | |
| 1-558 | H | H | Me | H | CH(OMe)Me | O | Me | H | |
| 1-559 | H | H | Me | H | CH(OMe)Pr | O | Me | H | |
| 1-560 | H | H | Me | H | CH₂CH(OMe)Me | O | Me | H | |
| 1-561 | H | H | Me | H | C(OMe)Me₂ | O | Me | H | |
| 1-562 | H | H | Me | H | C(OMe)MeEt | O | Me | H | |

TABLE 19

| Compound No. | X¹ | X² | X³ | X⁴ | Y | G | R¹ | R² | m.p. (° C.) |
|---|---|---|---|---|---|---|---|---|---|
| 1-563 | H | H | Me | H | C(OMe)MePr | O | Me | H | |
| 1-564 | H | H | Me | H | C(OMe)MeBu-t | O | Me | H | |
| 1-565 | H | H | Me | H | SiMe₃ | O | Me | H | |
| 1-566 | H | H | Me | H | SiEt₃ | O | Me | H | |
| 1-567 | H | H | Me | H | CH₂Ph | O | Me | H | |
| 1-568 | H | H | Me | H | CF₃ | O | Me | H | |
| 1-569 | H | F | H | H | H | O | Me | H | |
| 1-570 | H | F | H | H | Me | O | Me | H | |
| 1-571 | H | F | H | H | Et | O | Me | H | |
| 1-572 | H | F | H | H | Pr-i | O | Me | H | |
| 1-573 | H | F | H | H | Bu | O | Me | H | |
| 1-574 | H | F | H | H | Bu-i | O | Me | H | |
| 1-575 | H | F | H | H | Bu-t | O | Me | H | Oily |
| 1-576 | H | F | H | H | C₅H₁₁ | O | Me | H | |
| 1-577 | H | F | H | H | CHMePr | O | Me | H | |
| 1-578 | H | F | H | H | C₆H₁₃ | O | Me | H | |
| 1-579 | H | F | H | H | C₅H₉-c | O | Me | H | |
| 1-580 | H | F | H | H | CH=CH₂ | O | Me | H | |
| 1-581 | H | F | H | H | C(Me)=CH₂ | O | Me | H | |
| 1-582 | H | F | H | H | C(Me)=CHMe | O | Me | H | |
| 1-583 | H | F | H | H | CHClMe | O | Me | H | |
| 1-584 | H | F | H | H | CHClEt | O | Me | H | |
| 1-585 | H | F | H | H | CHClPr | O | Me | H | |
| 1-586 | H | F | H | H | CH₂CHClMe | O | Me | H | |
| 1-587 | H | F | H | H | CClMe₂ | O | Me | H | |
| 1-588 | H | F | H | H | CClMeEt | O | Me | H | |
| 1-589 | H | F | H | H | CClMePr | O | Me | H | |
| 1-590 | H | F | H | H | CClMePh | O | Me | H | |

TABLE 19-continued

| Compound No. | $X^1$ | $X^2$ | $X^3$ | $X^4$ | Y | G | $R^1$ | $R^2$ | m.p. (° C.) |
|---|---|---|---|---|---|---|---|---|---|
| 1-591 | H | F | H | H | CH(OMe)Me | O | Me | H | |
| 1-592 | H | F | H | H | CH(OMe)Pr | O | Me | H | |
| 1-593 | H | F | H | H | CH$_2$CH(OMe)Me | O | Me | H | |
| 1-594 | H | F | H | H | C(OMe)Me$_2$ | O | Me | H | |
| 1-595 | H | F | H | H | C(OMe)MeEt | O | Me | H | |

TABLE 20

| Compound No. | $X^1$ | $X^2$ | $X^3$ | $X^4$ | Y | G | $R^1$ | $R^2$ | m.p. (° C.) |
|---|---|---|---|---|---|---|---|---|---|
| 1-596 | H | F | H | H | C(OMe)MePr | O | Me | H | |
| 1-597 | H | F | H | H | C(OMe)MeBu-t | O | Me | H | |
| 1-598 | H | F | H | H | SiMe$_3$ | O | Me | H | |
| 1-599 | H | F | H | H | SiEt$_3$ | O | Me | H | |
| 1-600 | H | F | H | H | CH$_2$Ph | O | Me | H | |
| 1-601 | H | F | H | H | CF$_3$ | O | Me | H | |
| 1-602 | H | Me | H | H | H | O | Me | H | |
| 1-603 | H | Me | H | H | Me | O | Me | H | |
| 1-604 | H | Me | H | H | Et | O | Me | H | |
| 1-605 | H | Me | H | H | Pr-i | O | Me | H | |
| 1-606 | H | Me | H | H | Bu | O | Me | H | |
| 1-607 | H | Me | H | H | Bu-i | O | Me | H | |
| 1-608 | H | Me | H | H | Bu-t | O | Me | H | |
| 1-609 | H | Me | H | H | C$_5$H$_{11}$ | O | Me | H | |
| 1-610 | H | Me | H | H | CHMePr | Q | Me | H | |
| 1-611 | H | Me | H | H | C$_6$H$_{13}$ | O | Me | H | |
| 1-612 | H | Me | H | H | C$_5$H$_9$-c | O | Me | H | |
| 1-613 | H | Me | H | H | CH=CH$_2$ | O | Me | H | |
| 1-614 | H | Me | H | H | C(Me)=CH$_2$ | O | Me | H | |
| 1-615 | H | Me | H | H | C(Me)=CHMe | O | Me | H | |
| 1-616 | H | Me | H | H | CHClMe | O | Me | H | |
| 1-617 | H | Me | H | H | CHClEt | O | Me | H | |
| 1-618 | H | Me | H | H | CHClPr | O | Me | H | |
| 1-619 | H | Me | H | H | CH$_2$CHClMe | O | Me | H | |
| 1-620 | H | Me | H | H | CClMe$_2$ | O | Me | H | |
| 1-621 | H | Me | H | H | CClMeEt | O | Me | H | |
| 1-622 | H | Me | H | H | CClMePr | O | Me | H | |
| 1-623 | H | Me | H | H | CClMePh | O | Me | H | |
| 1-624 | H | Me | H | H | CH(OMe)Me | O | Me | H | |
| 1-625 | H | Me | H | H | CH(OMe)Pr | O | Me | H | |
| 1-626 | H | Me | H | H | CH$_2$CH(OMe)Me | O | Me | H | |
| 1-627 | H | Me | H | H | C(OMe)Me$_2$ | O | Me | H | |
| 1-628 | H | Me | H | H | C(OMe)MeEt | O | Me | H | |

TABLE 21

| Compound No. | $X^1$ | $X^2$ | $X^3$ | $X^4$ | Y | G | $R^1$ | $R^2$ | m.p. (° C.) |
|---|---|---|---|---|---|---|---|---|---|
| 1-629 | H | Me | H | H | C(OMe)MePr | O | Me | H | |
| 1-630 | H | Me | H | H | C(OMe)MeBu-t | O | Me | H | |
| 1-631 | H | Me | H | H | SiMe$_3$ | O | Me | H | |
| 1-632 | H | Me | H | H | SiEt$_3$ | O | Me | H | |
| 1-633 | H | Me | H | H | CH$_2$Ph | O | Me | H | |
| 1-634 | H | Me | H | H | CF$_3$ | O | Me | H | |
| 1-635 | Me | H | H | H | H | O | Me | H | |
| 1-636 | Me | H | H | H | Me | O | Me | H | |
| 1-637 | Me | H | H | H | Et | O | Me | H | |
| 1-638 | Me | H | H | H | Pr-i | O | Me | H | |
| 1-639 | Me | H | H | H | Bu | O | Me | H | |
| 1-640 | Me | H | H | H | Bu-i | O | Me | H | |
| 1-641 | Me | H | H | H | Bu-t | O | Me | H | |
| 1-642 | Me | H | H | H | C$_5$H$_{11}$ | O | Me | H | |
| 1-643 | Me | H | H | H | CH(Me)Pr | O | Me | H | |
| 1-644 | Me | H | H | H | C$_6$H$_{13}$ | O | Me | H | |
| 1-645 | Me | H | H | H | C$_5$H$_9$-c | O | Me | H | |
| 1-646 | Me | H | H | H | CH=CH$_2$ | O | Me | H | |
| 1-647 | Me | H | H | H | C(Me)=CH$_2$ | O | Me | H | |
| 1-648 | Me | H | H | H | C(Me)=CHMe | O | Me | H | |
| 1-649 | Me | H | H | H | CHClMe | O | Me | H | |
| 1-650 | Me | H | H | H | CHClEt | O | Me | H | |
| 1-651 | Me | H | H | H | CHClPr | O | Me | H | |
| 1-652 | Me | H | H | H | CH$_2$CHClMe | O | Me | H | |
| 1-653 | Me | H | H | H | CClMe$_2$ | O | Me | H | |
| 1-654 | Me | H | H | H | CClMeEt | O | Me | H | |
| 1-655 | Me | H | H | H | CClMePr | O | Me | H | |
| 1-656 | Me | H | H | H | CClMePh | O | Me | H | |
| 1-657 | Me | H | H | H | CH(OMe)Me | O | Me | H | |
| 1-658 | Me | H | H | H | CH(OMe)Pr | O | Me | H | |
| 1-659 | Me | H | H | H | CH$_2$CH(OMe)Me | O | Me | H | |
| 1-660 | Me | H | H | H | C(OMe)Me$_2$ | O | Me | H | |
| 1-661 | Me | H | H | H | C(OMe)MeEt | O | Me | H | |

TABLE 22

| Compound No. | $X^1$ | $X^2$ | $X^3$ | $X^4$ | Y | G | $R^1$ | $R^2$ | m.p. (° C.) |
|---|---|---|---|---|---|---|---|---|---|
| 1-662 | Me | H | H | H | C(OMe)MePr | O | Me | H | |
| 1-663 | Me | H | H | H | C(OMe)MeBu-t | O | Me | H | |
| 1-664 | Me | H | H | H | SiMe$_3$ | O | Me | H | |
| 1-665 | Me | H | H | H | SiEt$_3$ | O | Me | H | |
| 1-666 | Me | H | H | H | CH$_2$Ph | O | Me | H | |
| 1-667 | Me | H | H | H | CF$_3$ | O | Me | H | |
| 1-668 | H | H | H | F | Me | O | Me | Me | |
| 1-669 | H | H | H | F | Me | O | Me | CH$_2$OMe | |
| 1-670 | H | H | H | F | Me | O | Me | CH$_2$CH=CH$_2$ | |
| 1-671 | H | H | H | F | Me | O | Me | CH$_2$C≡CH | |

TABLE 22-continued

| Compound No. | X$^1$ | X$^2$ | X$^3$ | X$^4$ | Y | G | R$^1$ | R$^2$ | m.p. (° C.) |
|---|---|---|---|---|---|---|---|---|---|
| 1-672 | H | H | H | F | Me | O | Me | COMe | |
| 1-673 | H | H | H | F | Me | O | Me | COOMe | |
| 1-674 | H | H | H | F | Me | O | Me | OMe | |
| 1-675 | H | H | H | F | Et | O | Me | Me | |
| 1-676 | H | H | H | F | Et | O | Me | CH$_2$OMe | |
| 1-677 | H | H | H | F | Et | O | Me | CH$_2$CH=CH$_2$ | |
| 1-678 | H | H | H | F | Et | O | Me | CH$_2$C≡CH | |
| 1-679 | H | H | H | F | Et | O | Me | COMe | |
| 1-680 | H | H | H | F | Et | O | Me | COOMe | |
| 1-681 | H | H | H | F | Et | O | Me | OMe | |
| 1-682 | H | H | H | F | Pr-i | O | Me | Me | |
| 1-683 | H | H | H | F | Pr-i | O | Me | CH$_2$OMe | |
| 1-684 | H | H | H | F | Pr-i | O | Me | CH$_2$C≡CH | |
| 1-685 | H | H | H | F | Pr-i | O | Me | COMe | |
| 1-686 | H | H | H | F | Bu | O | Me | Me | |
| 1-687 | H | H | H | F | Bu | O | Me | CH$_2$OMe | |
| 1-688 | H | H | H | F | Bu | O | Me | CH$_2$CH=CH$_2$ | |
| 1-689 | H | H | H | F | Bu | O | Me | CH$_2$C≡CH | |
| 1-690 | H | H | H | F | Bu | O | Me | COMe | |
| 1-691 | H | H | H | F | Bu | O | Me | COOMe | |
| 1-692 | H | H | H | F | Bu | O | Me | OMe | |
| 1-693 | H | H | H | F | Bu-t | O | Me | Me | Oily |
| 1-694 | H | H | H | F | Bu-t | O | Me | CH$_2$OMe | Oily |

TABLE 23

| Compound No. | X$^1$ | X$^2$ | X$^3$ | X$^4$ | Y | G | R$^1$ | R$^2$ | m.p. (° C.) |
|---|---|---|---|---|---|---|---|---|---|
| 1-695 | H | H | H | F | Bu-t | O | Me | CH$_2$CH=CH$_2$ | |
| 1-696 | H | H | H | F | Bu-t | O | Me | CH$_2$C≡CH | Oily |
| 1-697 | H | H | H | F | Bu-t | O | Me | COMe | |
| 1-698 | H | H | H | F | Bu-t | O | Me | COOMe | Oily |
| 1-699 | H | H | H | F | Bu-t | O | Me | OMe | |
| 1-700 | H | H | H | F | C(Me)=CH$_2$ | O | Me | Me | |
| 1-701 | H | H | H | F | C(Me)=CH$_2$ | O | Me | CH$_2$OMe | |
| 1-702 | H | H | H | F | C(Me)=CH$_2$ | O | Me | CH$_2$CH=CH$_2$ | |
| 1-703 | H | H | H | F | C(Me)=CH$_2$ | O | Me | CH$_2$C≡CH | |
| 1-704 | H | H | H | F | C(Me)=CH$_2$ | O | Me | COMe | |
| 1-705 | H | H | H | F | C(Me)=CH$_2$ | O | Me | COOMe | |
| 1-706 | H | H | H | F | C(Me)=CH$_2$ | O | Me | OMe | |
| 1-707 | H | H | H | F | CH(OH)Me | O | Me | Me | |
| 1-708 | H | H | H | F | CH(OH)Me | O | Me | CH$_2$OMe | |
| 1-709 | H | H | H | F | CH(OH)Me | O | Me | CH$_2$CH=CH$_2$ | |
| 1-710 | H | H | H | F | CH(OH)Me | O | Me | CH$_2$C≡CH | |
| 1-711 | H | H | H | F | CH(OH)Me | O | Me | COMe | |
| 1-712 | H | H | H | F | CH(OH)Me | O | Me | COOMe | |
| 1-713 | H | H | H | F | CH(OH)Me | O | Me | OMe | |
| 1-714 | H | H | H | F | CH(OH)Et | O | Me | Me | |
| 1-715 | H | H | H | F | CH(OH)Et | O | Me | CH$_2$OMe | |
| 1-716 | H | H | H | F | CH(OH)Et | O | Me | CH$_2$CH=CH$_2$ | |
| 1-717 | H | H | H | F | CH(OH)Et | O | Me | CH$_2$C≡CH | |
| 1-718 | H | H | H | F | CH(OH)Et | O | Me | COMe | |
| 1-719 | H | H | H | F | CH(OH)Et | O | Me | COOMe | |
| 1-720 | H | H | H | F | CH(OH)Et | O | Me | OMe | |
| 1-721 | H | H | H | F | CHClMe | O | Me | Me | |
| 1-722 | H | H | H | F | CHClMe | O | Me | CH$_2$OMe | |
| 1-723 | H | H | H | F | CHClMe | O | Me | CH$_2$CH=CH$_2$ | |
| 1-724 | H | H | H | F | CHClMe | O | Me | CH$_2$C≡CH | |
| 1-725 | H | H | H | F | CHClMe | O | Me | COMe | |
| 1-726 | H | H | H | F | CHClMe | O | Me | COOMe | |

TABLE 24

| Compound No. | X$^1$ | X$^2$ | X$^3$ | X$^4$ | Y | G | R$^1$ | R$^2$ | m.p. (° C.) |
|---|---|---|---|---|---|---|---|---|---|
| 1-727 | H | H | H | F | CHClMe | O | Me | OMe | |

TABLE 24-continued

| Compound No. | X¹ | X² | X³ | X⁴ | Y | G | R¹ | R² | m.p. (° C.) |
|---|---|---|---|---|---|---|---|---|---|
| 1-728 | H | H | H | F | CHClEt | O | Me | Me | |
| 1-729 | H | H | H | F | CHClEt | O | Me | CH$_2$OMe | |
| 1-730 | H | H | H | F | CHClEt | O | Me | CH$_2$CH=CH$_2$ | |
| 1-731 | H | H | H | F | CHClEt | O | Me | CH$_2$C≡CH | |
| 1-732 | H | H | H | F | CHClEt | O | Me | COMe | |
| 1-733 | H | H | H | F | CHClEt | O | Me | COOMe | |
| 1-734 | H | H | H | F | CHClEt | O | Me | OMe | |
| 1-735 | H | H | H | F | CClMe$_2$ | O | Me | Me | |
| 1-736 | H | H | H | F | CClMe$_2$ | O | Me | CH$_2$OMe | |
| 1-737 | H | H | H | F | CClMe$_2$ | O | Me | CH$_2$CH=CH$_2$ | |
| 1-738 | H | H | H | F | CClMe$_2$ | O | Me | CH$_2$C≡CH | |
| 1-739 | H | H | H | F | CClMe$_2$ | O | Me | COMe | |
| 1-740 | H | H | H | F | CClMe$_2$ | O | Me | COOMe | |
| 1-741 | H | H | H | F | CClMe$_2$ | O | Me | OMe | |
| 1-742 | H | H | H | F | CClMeEt | O | Me | Me | |
| 1-743 | H | H | H | F | CClMeEt | O | Me | CH$_2$OMe | |
| 1-744 | H | H | H | F | CClMeEt | O | Me | CH$_2$CH=CH$_2$ | |
| 1-745 | H | H | H | F | CClMeEt | O | Me | CH$_2$C≡CH | |
| 1-746 | H | H | H | F | CClMeEt | O | Me | COMe | |
| 1-747 | H | H | H | F | CClMeEt | O | Me | COOMe | |
| 1-748 | H | H | H | F | CClMeEt | O | Me | OMe | |
| 1-749 | H | H | H | F | CClMePr | O | Me | Me | |
| 1-750 | H | H | H | F | CClMePr | O | Me | CH$_2$OMe | |
| 1-751 | H | H | H | F | CClMePr | O | Me | CH$_2$CH=CH$_2$ | |
| 1-752 | H | H | H | F | CClMePr | O | Me | CH$_2$C≡CH | |
| 1-753 | H | H | H | F | CClMePr | O | Me | COMe | |
| 1-754 | H | H | H | F | CClMePr | O | Me | COOMe | |
| 1-755 | H | H | H | F | CClMePr | O | Me | OMe | |
| 1-756 | H | H | H | F | CH(OMe)Me | O | Me | Me | |
| 1-757 | H | H | H | F | CH(OMe)Me | O | Me | CH$_2$OMe | |
| 1-758 | H | H | H | F | CH(OMe)Me | O | Me | CH$_2$CH=CH$_2$ | |

TABLE 25

| Compound No. | X¹ | X² | X³ | X⁴ | Y | G | R¹ | R² | m.p. (° C.) |
|---|---|---|---|---|---|---|---|---|---|
| 1-759 | H | H | H | F | CH(OMe)Me | O | Me | CH$_2$C≡CH | |
| 1-760 | H | H | H | F | CH(OMe)Me | O | Me | COMe | |
| 1-761 | H | H | H | F | CH(OMe)Me | O | Me | COOMe | |
| 1-762 | H | H | H | F | CH(OMe)Me | O | Me | OMe | |
| 1-763 | H | H | H | F | CH(OMe)Et | O | Me | Me | |
| 1-764 | H | H | H | F | CH(OMe)Et | O | Me | CH$_2$OMe | |
| 1-765 | H | H | H | F | CH(OMe)Et | O | Me | CH$_2$CH=CH$_2$ | |
| 1-766 | H | H | H | F | CH(OMe)Et | O | Me | CH$_2$C≡CH | |
| 1-767 | H | H | H | F | CH(OMe)Et | O | Me | COMe | |
| 1-768 | H | H | H | F | CH(OMe)Et | O | Me | COOMe | |
| 1-769 | H | H | H | F | CH(OMe)Et | O | Me | OMe | |
| 1-770 | H | H | H | F | C(OMe)Me$_2$ | O | Me | Me | |
| 1-771 | H | H | H | F | C(OMe)Me$_2$ | O | Me | CH$_2$OMe | |
| 1-772 | H | H | H | F | C(OMe)Me$_2$ | O | Me | CH$_2$CH=CH$_2$ | |
| 1-773 | H | H | H | F | C(OMe)Me$_2$ | O | Me | CH$_2$C≡CH | |
| 1-774 | H | H | H | F | C(OMe)Me$_2$ | O | Me | COMe | |
| 1-775 | H | H | H: | F | C(OMe)Me$_2$ | O | Me | COOMe | |
| 1-776 | H | H | H | F | C(OMe)Me$_2$ | O | Me | OMe | |
| 1-777 | H | H | H | F | C(OMe)MeEt | O | Me | Me | |
| 1-778 | H | H | H | F | C(OMe)MeEt | O | Me | CH$_2$OMe | |
| 1-779 | H | H | H | F | C(OMe)MeEt | O | Me | CH$_2$CH=CH$_2$ | |
| 1-780 | H | H | H | F | C(OMe)MeEt | O | Me | CH$_2$C≡CH | |
| 1-781 | H | H | H | F | C(OMe)MeEt | O | Me | COMe | |
| 1-782 | H | H | H | F | C(OMe)MeEt | O | Me | COOMe | |
| 1-783 | H | H | H | F | C(OMe)MeEt | O | Me | OMe | |
| 1-784 | H | H | H | F | C(OMe)MePr | O | Me | Me | |
| 1-785 | H | H | H | F | C(OMe)MePr | O | Me | CH$_2$OMe | |
| 1-786 | H | H | H | F | C(OMe)MePr | O | Me | CH$_2$CH=CH$_2$ | |
| 1-787 | H | H | H | F | C(OMe)MePr | O | Me | CH$_2$C≡CH | |
| 1-788 | H | H | H | F | C(OMe)MePr | O | Me | COMe | |
| 1-789 | H | H | H | F | C(OMe)MePr | O | Me | COOMe | |
| 1-790 | H | H | H | F | C(OMe)MePr | O | Me | OMe | |

TABLE 26

| Compound No. | X¹ | X² | X³ | X⁴ | Y | G | R¹ | R² | m.p. (° C.) |
|---|---|---|---|---|---|---|---|---|---|
| 1-791 | H | H | H | F | SiMe₃ | O | Me | Me | |
| 1-792 | H | H | H | F | SiMe₃ | O | Me | CH₂OMe | |
| 1-793 | H | H | H | F | SiMe₃ | O | Me | CH₂CH=CH₂ | |
| 1-794 | H | H | H | F | SiMe₃ | O | Me | CH₂C≡CH | |
| 1-795 | H | H | H | F | SiMe₃ | O | Me | COMe | |
| 1-796 | H | H | H | F | SiMe₃ | O | Me | COOMe | |
| 1-797 | H | H | H | F | SiMe₃ | O | Me | OMe | |
| 1-798 | H | H | H | F | SiEt₃ | O | Me | Me | |
| 1-799 | H | H | H | F | SiEt₃ | O | Me | CH₂OMe | |
| 1-800 | H | H | H | F | SiEt₃ | O | Me | CH₂CH=CH₂ | |
| 1-801 | H | H | H | F | SiEt₃ | O | Me | CH₂C≡CH | |
| 1-802 | H | H | H | F | SiEt₃ | O | Me | COMe | |
| 1-803 | H | H | H | F | SiEt₃ | O | Me | COOMe | |
| 1-804 | H | H | H | F | SiEt₃ | O | Me | OMe | |
| 1-805 | H | H | H | F | CF₃ | O | Me | Me | |
| 1-806 | H | H | H | F | CF₃ | O | Me | CH₂OMe | |
| 1-807 | H | H | H | F | CF₃ | O | Me | CH₂CH=CH₂ | |
| 1-808 | H | H | H | F | CF₃ | O | Me | CH₂C≡CH | |
| 1-809 | H | H | H | F | CF₃ | O | Me | COMe | |
| 1-810 | H | H | H | F | CF₃ | O | Me | COOMe | |
| 1-811 | H | H | H | F | CF₃ | O | Me | OMe | |
| 1-812 | H | H | H | Cl | Me | O | Me | Me | |
| 1-813 | H | H | H | Cl | Me | O | Me | CH₂OMe | |
| 1-814 | H | H | H | Cl | Me | O | Me | CH₂CH=CH₂ | |
| 1-815 | H | H | H | Cl | Me | O | Me | CH₂C≡CH | |
| 1-816 | H | H | H | Cl | Me | O | Me | COMe | |
| 1-817 | H | H | H | Cl | Me | O | Me | COOMe | |
| 1-818 | H | H | H | Cl | Me | O | Me | OMe | |
| 1-819 | H | H | H | Cl | Pr-i | O | Me | Me | |
| 1-820 | H | H | H | Cl | Pr-i | O | Me | CH₂OMe | |

TABLE 27

| Compound No. | X¹ | X² | X³ | X⁴ | Y | G | R¹ | R² | m.p. (° C.) |
|---|---|---|---|---|---|---|---|---|---|
| 1-821 | H | H | H | Cl | Pr-i | O | Me | CH₂CH=CH₂ | |
| 1-822 | H | H | H | Cl | Pr-i | O | Me | CH₂C≡CH | |
| 1-823 | H | H | H | Cl | Pr-i | O | Me | COMe | |
| 1-824 | H | H | H | Cl | Pr-i | O | Me | COOMe | |
| 1-825 | H | H | H | Cl | Pr-i | O | Me | OMe | |
| 1-826 | H | H | H | Cl | Bu | O | Me | Me | |
| 1-827 | H | H | H | Cl | Bu | O | Me | CH₂OMe | |
| 1-828 | H | H | H | Cl | Bu | O | Me | CH₂CH=CH₂ | |
| 1-829 | H | H | H | Cl | Bu | O | Me | CH₂C≡CH | |
| 1-830 | H | H | H | Cl | Bu | O | Me | COMe | |
| 1-831 | H | H | H | Cl | Bu | O | Me | COOMe | |
| 1-832 | H | H | H | Cl | Bu | O | Me | OMe | |
| 1-833 | H | H | H | Cl | Bu-t | O | Me | Me | |
| 1-834 | H | H | H | Cl | Bu-t | O | Me | CH₂OMe | |
| 1-835 | H | H | H | Cl | Bu-t | O | Me | CH₂CH=CH₂ | |
| 1-836 | H | H | H | Cl | Bu-t | O | Me | CH₂C≡CH | |
| 1-837 | H | H | H | Cl | Bu-t | O | Me | COMe | 86–89 |
| 1-838 | H | H | H | Cl | Bu-t | O | Me | COOMe | |
| 1-839 | H | H | H | Cl | Bu-t | O | Me | OMe | 63–66 |
| 1-840 | H | H | H | Cl | C₅H₁₁ | O | Me | Me | |
| 1-841 | H | H | H | Cl | C₅H₁₁ | O | Me | CH₂OMe | |
| 1-842 | H | H | H | Cl | C₅H₁₁ | O | Me | CH₂CH=CH₂ | |
| 1-843 | H | H | H | Cl | C₅H₁₁ | O | Me | CH₂C≡CH | |
| 1-844 | H | H | H | Cl | C₅H₁₁ | O | Me | COMe | |
| 1-845 | H | H | H | Cl | C₅H₁₁ | O | Me | COOMe | |
| 1-846 | H | H | H | Cl | C₅H₁₁ | O | Me | OMe | |
| 1-847 | H | H | H | Cl | Pr-i | O | Me | CH₂CH=CH₂ | |
| 1-848 | H | H | H | Cl | C₅H₉-c | O | Me | Me | |
| 1-849 | H | H | H | Cl | C₅H₉-c | O | Me | CH₂OMe | |
| 1-850 | H | H | H | Cl | C₅H₉-c | O | Me | CH₂CH=CH₂ | |
| 1-851 | H | H | H | Cl | C₅H₉-c | O | Me | CH₂C≡CH | |

TABLE 28

| Compound No. | X¹ | X² | X³ | X⁴ | Y | G | R¹ | R² | m.p. (° C.) |
|---|---|---|---|---|---|---|---|---|---|
| 1-852 | H | H | H | Cl | C₅H₉-c | O | Me | COMe | |
| 1-853 | H | H | H | Cl | C₅H₉-c | O | Me | COOMe | |
| 1-854 | H | H | H | Cl | C₅H₉-c | O | Me | OMe | |
| 1-855 | H | H | H | Cl | C(Me)=CH₂ | O | Me | Me | |
| 1-856 | H | H | H | Cl | C(Me)=CH₂ | O | Me | CH₂OMe | |
| 1-857 | H | H | H | Cl | C(Me)=CH₂ | O | Me | CH₂CH=CH₂ | |
| 1-858 | H | H | H | Cl | C(Me)=CH₂ | O | Me | CH₂C≡CH | |
| 1-859 | H | H | H | Cl | C(Me)=CH₂ | O | Me | COMe | |
| 1-860 | H | H | H | Cl | C(Me)=CH₂ | O | Me | COOMe | |
| 1-861 | H | H | H | Cl | C(Me)=CH₂ | O | Me | OMe | |
| 1-862 | H | H | H | Cl | CH₂CH=CH₂ | O | Me | Me | |
| 1-863 | H | H | H | Cl | CH₂CH=CH₂ | O | Me | CH₂OMe | |
| 1-864 | H | H | H | Cl | CH₂CH=CH₂ | O | Me | CH₂CH=CH₂ | |
| 1-865 | H | H | H | Cl | CH₂CH=CH₂ | O | Me | CH₂C≡CH | |
| 1-866 | H | H | H | Cl | CH₂CH=CH₂ | O | Me | COMe | |
| 1-867 | H | H | H | Cl | CH₂CH=CH₂ | O | Me | COOMe | |
| 1-868 | H | H | H | Cl | CH₂CH=CH₂ | O | Me | OMe | |
| 1-869 | H | H | H | Cl | Pr-i | O | Me | COOMe | |
| 1-870 | H | H | H | Cl | Pr-i | O | Me | OMe | |
| 1-871 | H | H | H | Cl | CHClMe | O | Me | Me | |
| 1-872 | H | H | H | Cl | CHClMe | O | Me | CH₂OMe | |
| 1-873 | H | H | H | Cl | CHClMe | O | Me | CH₂CH=CH₂ | |
| 1-874 | H | H | H | Cl | CHClMe | O | Me | CH₂C≡CH | |
| 1-875 | H | H | H | Cl | CHClMe | O | Me | COMe | |
| 1-876 | H | H | H | Cl | CHClMe | O | Me | COOMe | |
| 1-877 | H | H | H | Cl | CHClMe | O | Me | OMe | |
| 1-878 | H | H | H | Cl | CHClEt | O | Me | Me | |
| 1-879 | H | H | H | Cl | CHClEt | O | Me | CH₂OMe | |
| 1-880 | H | H | H | Cl | CHClEt | O | Me | CH₂CH=CH₂ | |
| 1-881 | H | H | H | Cl | CHClEt | O | Me | CH₂C≡CH | |

TABLE 29

| Compound No. | X¹ | X² | X³ | X⁴ | Y | G | R¹ | R² | m.p. (° C.) |
|---|---|---|---|---|---|---|---|---|---|
| 1-882 | H | H | H | Cl | CHClEt | O | Me | COMe | |
| 1-883 | H | H | H | Cl | CHClEt | O | Me | COOMe | |
| 1-884 | H | H | H | Cl | CHClEt | O | Me | OMe | |
| 1-885 | H | H | H | Cl | CClMe₂ | O | Me | Me | |
| 1-886 | H | H | H | Cl | CClMe₂ | O | Me | CH₂OMe | |
| 1-887 | H | H | H | Cl | CClMe₂ | O | Me | CH₂CH=CH₂ | |
| 1-888 | H | H | H | Cl | CClMe₂ | O | Me | CH₂C≡CH | |
| 1-889 | H | H | H | Cl | CClMe₂ | O | Me | COMe | |
| 1-890 | H | H | H | Cl | CClMe₂ | O | Me | COOMe | |
| 1-891 | H | H | H | Cl | CClMe₂ | O | Me | OMe | |
| 1-892 | H | H | H | Cl | CClMeEt | O | Me | Me | |
| 1-893 | H | H | H | Cl | CClMeEt | O | Me | CH₂OMe | |
| 1-894 | H | H | H | Cl | CClMeEt | O | Me | CH₂CH=CH₂ | |
| 1-895 | H | H | H | Cl | CClMeEt | O | Me | CH₂C≡CH | |
| 1-896 | H | H | H | Cl | CClMeEt | O | Me | COMe | |
| 1-897 | H | H | H | Cl | CClMeEt | O | Me | COOMe | |
| 1-898 | H | H | H | Cl | CClMeEt | O | Me | OMe | |
| 1-899 | H | H | H | Cl | CClMePr | O | Me | Me | |
| 1-900 | H | H | H | Cl | CClMePr | O | Me | CH₂OMe | |
| 1-901 | H | H | H | Cl | CClMePr | O | Me | CH₂CH=CH₂ | |
| 1-902 | H | H | H | Cl | CClMePr | O | Me | CH₂C≡CH | |
| 1-903 | H | H | H | Cl | CClMePr | O | Me | COMe | |
| 1-904 | H | H | H | Cl | CClMePr | O | Me | COOMe | |
| 1-905 | H | H | H | Cl | CClMePr | O | Me | OMe | |
| 1-906 | H | H | H | Cl | CH(OMe)Me | O | Me | Me | |
| 1-907 | H | H | H | Cl | CH(OMe)Me | O | Me | CH₂OMe | |
| 1-908 | H | H | H | Cl | CH(OMe)Me | O | Me | CH₂CH=CH₂ | |
| 1-909 | H | H | H | Cl | CH(OMe)Me | O | Me | CH₂C≡CH | |
| 1-910 | H | H | H | Cl | CH(OMe)Me | O | Me | COMe | |
| 1-911 | H | H | H | Cl | CH(OMe)Me | O | Me | COOMe | |
| 1-912 | H | H | H | Cl | CH(OMe)Me | O | Me | OMe | |
| 1-913 | H | H | H | Cl | CH(OMe)Et | O | Me | Me | |

TABLE 30

| Compound No. | $X^1$ | $X^2$ | $X^3$ | $X^4$ | Y | G | $R^1$ | $R^2$ | m.p. (° C.) |
|---|---|---|---|---|---|---|---|---|---|
| 1-914 | H | H | H | Cl | CH(OMe)Et | O | Me | $CH_2OMe$ | |
| 1-915 | H | H | H | Cl | CH(OMe)Et | O | Me | $CH_2CH=CH_2$ | |
| 1-916 | H | H | H | Cl | CH(OMe)Et | O | Me | $CH_2C\equiv CH$ | |
| 1-917 | H | H | H | Cl | CH(OMe)Et | O | Me | COMe | |
| 1-918 | H | H | H | Cl | CH(OMe)Et | O | Me | COOMe | |
| 1-919 | H | H | H | Cl | CH(OMe)Et | O | Me | OMe | |
| 1-920 | H | H | H | Cl | $C(OMe)Me_2$ | O | Me | Me | |
| 1-921 | H | H | H | Cl | $C(OMe)Me_2$ | O | Me | $CH_2OMe$ | |
| 1-922 | H | H | H | Cl | $C(OMe)Me_2$ | O | Me | $CH_2CH=CH_2$ | |
| 1-923 | H | H | H | Cl | $C(OMe)Me_2$ | O | Me | $CH_2C\equiv CH$ | |
| 1-924 | H | H | H | Cl | $C(OMe)Me_2$ | O | Me | COMe | |
| 1-925 | H | H | H | Cl | $C(OMe)Me_2$ | O | Me | COOMe | |
| 1-926 | H | H | H | Cl | $C(OMe)Me_2$ | O | Me | OMe | |
| 1-927 | H | H | H | Cl | C(OMe)MeEt | O | Me | Me | |
| 1-928 | H | H | H | Cl | C(OMe)MeEt | O | Me | $CH_2OMe$ | |
| 1-929 | H | H | H | Cl | C(OMe)MeEt | O | Me | $CH_2CH=CH_2$ | |
| 1-930 | H | H | H | Cl | C(OMe)MeEt | O | Me | $CH_2C\equiv CH$ | |
| 1-931 | H | H | H | Cl | C(OMe)MeEt | O | Me | COMe | |
| 1-932 | H | H | H | Cl | C(OMe)MeEt | O | Me | COOMe | |
| 1-933 | H | H | H | Cl | C(OMe)MeEt | O | Me | OMe | |
| 1-934 | H | H | H | Cl | C(OMe)MePr | O | Me | Me | |
| 1-935 | H | H | H | Cl | C(OMe)MePr | O | Me | $CH_2OMe$ | |
| 1-936 | H | H | H | Cl | C(OMe)MePr | O | Me | $CH_2CH=CH_2$ | |
| 1-937 | H | H | H | Cl | C(OMe)MePr | O | Me | $CH_2C\equiv CH$ | |
| 1-938 | H | H | H | Cl | C(OMe)MePr | O | Me | COMe | |
| 1-939 | H | H | H | Cl | C(OMe)MePr | O | Me | COOMe | |
| 1-940 | H | H | H | Cl | C(OMe)MePr | O | Me | OMe | |
| 1-941 | H | H | H | Cl | $SiMe_3$ | O | Me | Me | |
| 1-942 | H | H | H | Cl | $SiMe_3$ | O | Me | $CH_2OMe$ | |
| 1-943 | H | H | H | Cl | $SiMe_3$ | O | Me | $CH_2CH=CH_2$ | |
| 1-944 | H | H | H | Cl | $SiMe_3$ | O | Me | $CH_2C\equiv CH$ | |

TABLE 31

| Compound No. | $X^1$ | $X^2$ | $X^3$ | $X^4$ | Y | G | $R^1$ | $R^2$ | m.p. (° C.) |
|---|---|---|---|---|---|---|---|---|---|
| 1-945 | H | H | H | Cl | $SiMe_3$ | O | Me | COMe | |
| 1-946 | H | H | H | Cl | $SiMe_3$ | O | Me | COOMe | |
| 1-947 | H | H | H | Cl | $SiMe_3$ | O | Me | OMe | |
| 1-948 | H | H | H | Cl | $SiEt_3$ | O | Me | Me | |
| 1-949 | H | H | H | Cl | $SiEt_3$ | O | Me | $CH_2OMe$ | |
| 1-950 | H | H | H | Cl | $SiEt_3$ | O | Me | $CH_2CH=CH_2$ | |
| 1-951 | H | H | H | Cl | $SiEt_3$ | O | Me | $CH_2C\equiv CH$ | |
| 1-952 | H | H | H | Cl | $SiEt_3$ | O | Me | COMe | |
| 1-953 | H | H | H | Cl | $SiEt_3$ | O | Me | COOMe | |
| 1-954 | H | H | H | Cl | $SiEt_3$ | O | Me | OMe | |
| 1-955 | H | H | H | Cl | $CF_3$ | O | Me | Me | |
| 1-956 | H | H | H | Cl | $CF_3$ | O | Me | $CH_2OMe$ | |
| 1-957 | H | H | H | Cl | $CF_3$ | O | Me | $CH_2CH=CH_2$ | |
| 1-958 | H | H | H | Cl | $CF_3$ | O | Me | $CH_2C\equiv CH$ | |
| 1-959 | H | H | H | Cl | $CF_3$ | O | Me | COMe | |
| 1-960 | H | H | H | Cl | $CF_3$ | O | Me | COOMe | |
| 1-961 | H | H | H | Cl | $CF_3$ | O | Me | OMe | |
| 1-962 | H | H | H | Me | Me | O | Me | Me | |
| 1-963 | H | H | H | Me | Me | O | Me | $CH_2OMe$ | |
| 1-964 | H | H | H | Me | Me | O | Me | $CH_2CH=CH_2$ | |
| 1-965 | H | H | H | Me | Me | O | Me | $CH_2C\equiv CH$ | |
| 1-966 | H | H | H | Me | Me | O | Me | COMe | |
| 1-967 | H | H | H | Me | Me | O | Me | COOMe | |
| 1-968 | H | H | H | Me | Me | O | Me | OMe | |
| 1-969 | H | H | H | Me | Pr | O | Me | Me | |
| 1-970 | H | H | H | Me | Pr | O | Me | $CH_2OMe$ | |
| 1-971 | H | H | H | Me | Pr | O | Me | $CH_2CH=CH_2$ | |
| 1-972 | H | H | H | Me | Pr | O | Me | $CH_2C\equiv CH$ | |
| 1-973 | H | H | H | Me | Pr | O | Me | COMe | |
| 1-974 | H | H | H | Me | Pr | O | Me | COOMe | |

TABLE 32

| Compound No. | $X^1$ | $X^2$ | $X^3$ | $X^4$ | Y | G | $R^1$ | $R^2$ | m.p. (° C.) |
|---|---|---|---|---|---|---|---|---|---|
| 1-975 | H | H | H | Me | Pr | O | Me | OMe | |
| 1-976 | H | H | H | Me | Pr-i | O | Me | Me | |
| 1-977 | H | H | H | Me | Pr-i | O | Me | $CH_2OMe$ | |
| 1-978 | H | H | H | Me | Pr-i | O | Me | $CH_2CH=CH_2$ | |
| 1-979 | H | H | H | Me | Pr-i | O | Me | $CH_2C\equiv CH$ | |
| 1-980 | H | H | H | Me | Pr-i | O | Me | COMe | |
| 1-981 | H | H | H | Me | Pr-i | O | Me | COOMe | |
| 1-982 | H | H | H | Me | Pr-i | O | Me | OMe | |
| 1-983 | H | H | H | Me | Bu-t | O | Me | Me | |
| 1-984 | H | H | H | Me | Bu-t | O | Me | $CH_2OMe$ | |
| 1-985 | H | H | H | Me | Bu-t | O | Me | $CH_2CH=CH_2$ | |
| 1-986 | H | H | H | Me | Bu-t | O | Me | $CH_2C\equiv CH$ | |
| 1-987 | H | H | H | Me | Bu-t | O | Me | COMe | |
| 1-988 | H | H | H | Me | Bu-t | O | Me | COOMe | |
| 1-989 | H | H | H | Me | Bu-t | O | Me | OMe | |
| 1-990 | H | H | H | Me | CHMePr | O | Me | Me | |
| 1-991 | H | H | H | Me | CHMePr | O | Me | $CH_2OMe$ | |
| 1-992 | H | H | H | Me | CHMePr | O | Me | $CH_2CH=CH_2$ | |
| 1-993 | H | H | H | Me | CHMePr | O | Me | $CH_2C\equiv CH$ | |
| 1-994 | H | H | H | Me | CHMePr | O | Me | COMe | |
| 1-995 | H | H | H | Me | CHMePr | O | Me | COOMe | |
| 1-996 | H | H | H | Me | CHMePr | O | Me | OMe | |
| 1-997 | H | H | H | Me | $C(Me)=CH_2$ | O | Me | Me | |
| 1-998 | H | H | H | Me | $C(Me)=CH_2$ | O | Me | $CH_2OMe$ | |
| 1-999 | H | H | H | Me | $C(Me)=CH_2$ | O | Me | $CH_2CH=CH_2$ | |
| 1-1000 | H | H | H | Me | $C(Me)=CH_2$ | O | Me | $CH_2C\equiv CH$ | |
| 1-1001 | H | H | H | Me | $C(Me)=CH_2$ | O | Me | COMe | |
| 1-1002 | H | H | H | Me | $C(Me)=CH_2$ | O | Me | COOMe | |
| 1-1003 | H | H | H | Me | $C(Me)=CH_2$ | O | Me | OMe | |
| 1-1004 | H | H | H | Me | $CH_2CH=CH_2$ | O | Me | Me | |
| 1-1005 | H | H | H | Me | $CH_2CH=CH_2$ | O | Me | $CH_2OMe$ | |
| 1-1006 | H | H | H | Me | $CH_2CH=CH_2$ | O | Me | $CH_2CH=CH_2$ | |

TABLE 33

| Compound No. | $X^1$ | $X^2$ | $X^3$ | $X^4$ | Y | G | $R^1$ | $R^2$ | m.p. (° C.) |
|---|---|---|---|---|---|---|---|---|---|
| 1-1007 | H | H | H | Me | $CH_2CH=CH_2$ | O | Me | $CH_2C\equiv CH$ | |
| 1-1008 | H | H | H | Me | $CH_2CH=CH_2$ | O | Me | COMe | |
| 1-1009 | H | H | H | Me | $CH_2CH=CH_2$ | O | Me | COOMe | |
| 1-1010 | H | H | H | Me | $CH_2CH=CH_2$ | O | Me | OMe | |
| 1-1011 | H | H | H | Me | CH(OH)Me | O | Me | Me | |
| 1-1012 | H | H | H | Me | CH(OH)Me | O | Me | $CH_2OMe$ | |
| 1-1013 | H | H | H | Me | CH(OH)Me | O | Me | $CH_2CH=CH_2$ | |
| 1-1014 | H | H | H | Me | CH(OH)Me | O | Me | $CH_2C\equiv CH$ | |
| 1-1015 | H | H | H | Me | CH(OH)Me | O | Me | COMe | |
| 1-1016 | H | H | H | Me | CH(OH)Me | O | Me | COOMe | |
| 1-1017 | H | H | H | Me | CH(OH)Me | O | Me | OMe | |
| 1-1018 | H | H | H | Me | CH(OH)Et | O | Me | Me | |
| 1-1019 | H | H | H | Me | CH(OH)Et | O | Me | $CH_2OMe$ | |
| 1-1020 | H | H | H | Me | CH(OH)Et | O | Me | $CH_2CH=CH_2$ | |
| 1-1021 | H | H | H | Me | CH(OH)Et | O | Me | $CH_2C\equiv CH$ | |
| 1-1022 | H | H | H | Me | CH(OH)Et | O | Me | COMe | |
| 1-1023 | H | H | H | Me | CH(OH)Et | O | Me | COOMe | |
| 1-1024 | H | H | H | Me | CH(OH)Et | O | Me | OMe | |
| 1-1025 | H | H | H | Me | CHClMe | O | Me | Me | |
| 1-1026 | H | H | H | Me | CHClMe | O | Me | $CH_2OMe$ | |
| 1-1027 | H | H | H | Me | CHClMe | O | Me | $CH_2CH=CH_2$ | |
| 1-1028 | H | H | H | Me | CHClMe | O | Me | $CH_2C\equiv CH$ | |
| 1-1029 | H | H | H | Me | CHClMe | O | Me | COMe | |
| 1-1030 | H | H | H | Me | CHClMe | O | Me | COOMe | |
| 1-1031 | H | H | H | Me | CHClMe | O | Me | OMe | |
| 1-1032 | H | H | H | Me | CHClEt | O | Me | Me | |
| 1-1033 | H | H | H | Me | CHClEt | O | Me | $CH_2OMe$ | |
| 1-1034 | H | H | H | Me | CHClEt | O | Me | $CH_2CH=CH_2$ | |
| 1-1035 | H | H | H | Me | CHClEt | O | Me | $CH_2C\equiv CH$ | |
| 1-1036 | H | H | H | Me | CHClEt | O | Me | COMe | |
| 1-1037 | H | H | H | Me | CHClEt | O | Me | COOMe | |
| 1-1038 | H | H | H | Me | CHClEt | O | Me | OMe | |

TABLE 34

| Compound No. | X¹ | X² | X³ | X⁴ | Y | G | R¹ | R² | m.p. (° C.) |
|---|---|---|---|---|---|---|---|---|---|
| 1-1039 | H | H | H | Me | CClMe$_2$ | O | Me | Me | |
| 1-1040 | H | H | H | Me | CClMe$_2$ | O | Me | CH$_2$OMe | |
| 1-1041 | H | H | H | Me | CClMe$_2$ | O | Me | CH$_2$CH=CH$_2$ | |
| 1-1042 | H | H | H | Me | CClMe$_2$ | O | Me | CH$_2$C≡CH | |
| 1-1043 | H | H | H | Me | CClMe$_2$ | O | Me | COMe | |
| 1-1044 | H | H | H | Me | CClMe$_2$ | O | Me | COOMe | |
| 1-1045 | H | H | H | Me | CClMe$_2$ | O | Me | OMe | |
| 1-1046 | H | H | H | Me | CClMeEt | O | Me | Me | |
| 1-1047 | H | H | H | Me | CClMeEt | O | Me | CH$_2$OMe | |
| 1-1048 | H | H | H | Me | CClMeEt | O | Me | CH$_2$CH=CH$_2$ | |
| 1-1049 | H | H | H | Me | CClMeEt | O | Me | CH$_2$C≡CH | |
| 1-1050 | H | H | H | Me | CClMeEt | O | Me | COMe | |
| 1-1051 | H | H | H | Me | CClMeEt | O | Me | COOMe | |
| 1-1052 | H | H | H | Me | CClMeEt | O | Me | OMe | |
| 1-1053 | H | H | H | Me | CClMePr | O | Me | Me | |
| 1-1054 | H | H | H | Me | CClMePr | O | Me | CH$_2$OMe | |
| 1-1055 | H | H | H | Me | CClMePr | O | Me | CH$_2$CH=CH$_2$ | |
| 1-1056 | H | H | H | Me | CClMePr | O | Me | CH$_2$C≡CH | |
| 1-1057 | H | H | H | Me | CClMePr | O | Me | COMe | |
| 1-1058 | H | H | H | Me | CClMePr | O | Me | COOMe | |
| 1-1059 | H | H | H | Me | CClMePr | O | Me | OMe | |
| 1-1060 | H | H | H | Me | CH(OMe)Me | O | Me | Me | |
| 1-1061 | H | H | H | Me | CH(OMe)Me | O | Me | CH$_2$OMe | |
| 1-1062 | H | H | H | Me | CH(OMe)Me | O | Me | CH$_2$CH=CH$_2$ | |
| 1-1063 | H | H | H | Me | CH(OMe)Me | O | Me | CH$_2$C≡CH | |
| 1-1064 | H | H | H | Me | CH(OMe)Me | O | Me | COMe | |
| 1-1065 | H | H | H | Me | CH(OMe)Me | O | Me | COOMe | |
| 1-1066 | H | H | H | Me | CH(OMe)Me | O | Me | OMe | |
| 1-1067 | H | H | H | Me | CH(OMe)Et | O | Me | Me | |
| 1-1068 | H | H | H | Me | CH(OMe)Et | O | Me | CH$_2$OMe | |
| 1-1069 | H | H | H | Me | CH(OMe)Et | O | Me | CH$_2$CH=CH$_2$ | |
| 1-1070 | H | H | H | Me | CH(OMe)Et | O | Me | CH$_2$C≡CH | |

TABLE 35

| Compound No. | X¹ | X² | X³ | X⁴ | Y | G | R¹ | R² | m.p. (° C.) |
|---|---|---|---|---|---|---|---|---|---|
| 1-1071 | H | H | H | Me | CH(OMe)Et | O | Me | COMe | |
| 1-1072 | H | H | H | Me | CH(OMe)Et | O | Me | COOMe | |
| 1-1073 | H | H | H | Me | CH(OMe)Et | O | Me | OMe | |
| 1-1074 | H | H | H | Me | C(OMe)Me$_2$ | O | Me | Me | |
| 1-1075 | H | H | H | Me | C(OMe)Me$_2$ | O | Me | CH$_2$OMe | |
| 1-1076 | H | H | H | Me | C(OMe)Me$_2$ | O | Me | CH$_2$CH=CH$_2$ | |
| 1-1077 | H | H | H | Me | C(OMe)Me$_2$ | O | Me | CH$_2$C≡CH | |
| 1-1078 | H | H | H | Me | C(OMe)Me$_2$ | O | Me | COMe | |
| 1-1079 | H | H | H | Me | C(OMe)Me$_2$ | O | Me | COOMe | |
| 1-1080 | H | H | H | Me | C(OMe)Me$_2$ | O | Me | OMe | |
| 1-1081 | H | H | H | Me | C(OMe)MeEt | O | Me | Me | |
| 1-1082 | H | H | H | Me | C(OMe)MeEt | O | Me | CH$_2$OMe | |
| 1-1083 | H | H | H | Me | C(OMe)MeEt | O | Me | CH$_2$CH=CH$_2$ | |
| 1-1084 | H | H | H | Me | C(OMe)MeEt | O | Me | CH$_2$C≡CH | |
| 1-1085 | H | H | H | Me | C(OMe)MeEt | O | Me | COMe | |
| 1-1086 | H | H | H | Me | C(OMe)MeEt | O | Me | COOMe | |
| 1-1087 | H | H | H | Me | C(OMe)MeEt | O | Me | OMe | |
| 1-1088 | H | H | H | Me | SiMe$_3$ | O | Me | Me | |
| 1-1089 | H | H | H | Me | SiMe$_3$ | O | Me | CH$_2$OMe | |
| 1-1090 | H | H | H | Me | SiMe$_3$ | O | Me | CH$_2$CH=CH$_2$ | |
| 1-1091 | H | H | H | Me | SiMe$_3$ | O | Me | CH$_2$C≡CH | |
| 1-1092 | H | H | H | Me | SiMe$_3$ | O | Me | COMe | |
| 1-1093 | H | H | H | Me | SiMe$_3$ | O | Me | COOMe | |
| 1-1094 | H | H | H | Me | SiMe$_3$ | O | Me | OMe | |
| 1-1095 | H | H | H | Me | SiEt$_3$ | O | Me | Me | |
| 1-1096 | H | H | H | Me | SiEt$_3$ | O | Me | CH$_2$OMe | |
| 1-1097 | H | H | H | Me | SiEt$_3$ | O | Me | CH$_2$CH=CH$_2$ | |
| 1-1098 | H | H | H | Me | SiEt$_3$ | O | Me | CH$_2$C≡CH | |
| 1-1099 | H | H | H | Me | SiEt$_3$ | O | Me | COMe | |
| 1-1100 | H | H | H | Me | SiEt$_3$ | O | Me | COOMe | |

TABLE 36

| Compound No. | X¹ | X² | X³ | X⁴ | Y | G | R¹ | R² | m.p. (° C.) |
|---|---|---|---|---|---|---|---|---|---|
| 1-1101 | H | H | H | Me | SiEt$_3$ | O | Me | OMe | |
| 1-1102 | H | H | H | Me | CF$_3$ | O | Me | Me | |
| 1-1103 | H | H | H | Me | CF$_3$ | O | Me | CH$_2$OMe | |
| 1-1104 | H | H | H | Me | CF$_3$ | O | Me | CH$_2$CH=CH$_2$ | |
| 1-1105 | H | H | H | Me | CF$_3$ | O | Me | CH$_2$C≡CH | |
| 1-1106 | H | H | H | Me | CF$_3$ | O | Me | COMe | |
| 1-1107 | H | H | H | Me | CF$_3$ | O | Me | COOMe | |
| 1-1108 | H | H | H | Me | CF$_3$ | O | Me | OMe | |
| 1-1109 | H | H | H | F | Me | O | Et | H | |
| 1-1110 | H | H | H | F | Me | O | Pr-i | H | |
| 1-1111 | H | H | H | F | Me | S | Me | H | |
| 1-1112 | H | H | H | F | Me | NH | Me | H | |
| 1-1113 | H | H | H | F | Et | O | Et | H | |
| 1-1114 | H | H | H | F | Et | O | Pr-i | H | |
| 1-1115 | H | H | H | F | Et | S | Me | H | |
| 1-1116 | H | H | H | F | Et | NH | Me | H | |
| 1-1117 | H | H | H | F | Pr-i | O | Et | H | |
| 1-1118 | H | H | H | F | Pr-i | O | Pr-i | H | |
| 1-1119 | H | H | H | F | Pr-i | S | Me | H | |
| 1-1120 | H | H | H | F | Pr-i | NH | Me | H | |
| 1-1121 | H | H | H | F | Bu-t | O | Et | H | |
| 1-1122 | H | H | H | F | Bu-t | O | Pr-i | H | |
| 1-1123 | H | H | H | F | Bu-t | S | Me | H | |
| 1-1124 | H | H | H | F | Bu-t | NH | Me | H | 175–178 |
| 1-1125 | H | H | H | F | C(Me)=CH$_2$ | O | Et | H | |
| 1-1126 | H | H | H | F | C(Me)=CH$_2$ | O | Pr-i | H | |
| 1-1127 | H | H | H | F | C(Me)=CH$_2$ | S | Me | H | |
| 1-1128 | H | H | H | F | C(Me)=CH$_2$ | NH | Me | H | |
| 1-1129 | H | H | H | F | CH(OH)Et | O | Et | H | |
| 1-1130 | H | H | H | F | CH(OH)Et | O | Pr-i | H | |
| 1-1131 | H | H | H | F | CH(OH)Et | S | Me | H | |
| 1-1132 | H | H | H | F | CH(OH)Et | NH | Me | H | |
| 1-1133 | H | H | H | F | CHClMe | O | Et | H | |
| 1-1134 | H | H | H | F | CHClMe | O | Pr-i | H | |

TABLE 37

| Compound No. | X¹ | X² | X³ | X⁴ | Y | G | R¹ | R² | m.p. (° C.) |
|---|---|---|---|---|---|---|---|---|---|
| 1-1135 | H | H | H | F | CHClMe | S | Me | H | |
| 1-1136 | H | H | H | F | CHClMe | NH | Me | H | |
| 1-1137 | H | H | H | F | CHClEt | O | Et | H | |
| 1-1138 | H | H | H | F | CHClEt | O | Pr-i | H | |
| 1-1139 | H | H | H | F | CHClEt | S | Me | H | |
| 1-1140 | H | H | H | F | CHClEt | NH | Me | H | |
| 1-1141 | H | H | H | F | CClMe$_2$ | O | Et | H | |
| 1-1142 | H | H | H | F | CClMe$_2$ | O | Pr-i | H | |
| 1-1143 | H | H | H | F | CClMe$_2$ | S | Me | H | |
| 1-1144 | H | H | H | F | CClMe$_2$ | NH | Me | H | |
| 1-1145 | H | H | H | F | CClMeEt | O | Et | H | |
| 1-1146 | H | H | H | F | CClMeEt | O | Pr-i | H | |
| 1-1147 | H | H | H | F | CClMeEt | S | Me | H | |
| 1-1148 | H | H | H | F | CClMeEt | NH | Me | H | |
| 1-1149 | H | H | H | F | CH(OMe)Me | O | Et | H | |
| 1-1150 | H | H | H | F | CH(OMe)Me | O | Pr-i | H | |
| 1-1151 | H | H | H | F | CH(OMe)Me | S | Me | H | |
| 1-1152 | H | H | H | F | CH(OMe)Me | NH | Me | H | |
| 1-1153 | H | H | H | F | C(OMe)Me$_2$ | O | Et | H | |
| 1-1154 | H | H | H | F | C(OMe)Me$_2$ | O | Pr-i | H | |
| 1-1155 | H | H | H | F | C(OMe)Me$_2$ | S | Me | H | |
| 1-1156 | H | H | H | F | C(OMe)Me$_2$ | NH | Me | H | |
| 1-1157 | H | H | H | F | C(OMe)MeEt | O | Et | H | |
| 1-1158 | H | H | H | F | C(OMe)MeEt | O | Pr-i | H | |
| 1-1159 | H | H | H | F | C(OMe)MeEt | S | Me | H | |
| 1-1160 | H | H | H | F | C(OMe)MeEt | NH | Me | H | |
| 1-1161 | H | H | H | F | SiMe$_3$ | O | Et | H | |
| 1-1162 | H | H | H | F | SiMe$_3$ | O | Pr-i | H | |
| 1-1163 | H | H | H | F | SiMe$_3$ | S | Me | H | |
| 1-1164 | H | H | H | F | SiMe$_3$ | NH | Me | H | |
| 1-1165 | H | H | H | F | SiEt$_3$ | O | Et | H | |

TABLE 37-continued

| Compound No. | X¹ | X² | X³ | X⁴ | Y | G | R¹ | R² | m.p. (° C.) |
|---|---|---|---|---|---|---|---|---|---|
| 1-1166 | H | H | H | F | SiEt₃ | O | Pr-i | H | |
| 1-1167 | H | H | H | F | SiEt₃ | S | Me | H | |

TABLE 38

| Compound No. | X¹ | X² | X³ | X⁴ | Y | G | R¹ | R² | m.p. (° C.) |
|---|---|---|---|---|---|---|---|---|---|
| 1-1168 | H | H | H | F | SiEt₃ | NH | Me | H | |
| 1-1169 | H | H | H | Cl | Et | O | Et | H | |
| 1-1170 | H | H | H | Cl | Et | O | Pr-i | H | |
| 1-1171 | H | H | H | Cl | Et | S | Me | H | |
| 1-1172 | H | H | H | Cl | Et | NH | Me | H | |
| 1-1173 | H | H | H | Cl | Pr-i | O | Et | H | |
| 1-1174 | H | H | H | Cl | Pr-i | O | Pr-i | H | |
| 1-1175 | H | H | H | Cl | Pr-i | S | Me | H | |
| 1-1176 | H | H | H | Cl | Pr-i | NH | Me | H | |
| 1-1177 | H | H | H | Cl | C(Me)=CH₂ | O | Et | H | Oily |
| 1-1178 | H | H | H | Cl | C(Me)=CH₂ | O | Pr-i | H | |
| 1-1179 | H | H | H | Cl | C(Me)=CH₂ | S | Me | H | |
| 1-1180 | H | H | H | Cl | C(Me)=CH₂ | NH | Me | H | |
| 1-1181 | H | H | H | Cl | CHClEt | O | Et | H | |
| 1-1182 | H | H | H | Cl | CHClEt | O | Pr-i | H | |
| 1-1183 | H | H | H | Cl | CHClEt | S | Me | H | |
| 1-1184 | H | H | H | Cl | CHClEt | NH | Me | H | |
| 1-1185 | H | H | H | Cl | CClMe₂ | O | Et | H | |
| 1-1186 | H | H | H | Cl | CClMe₂ | O | Pr-i | H | |
| 1-1187 | H | H | H | Cl | CClMe₂ | S | Me | H | |
| 1-1188 | H | H | H | Cl | CClMe₂ | NH | Me | H | |
| 1-1189 | H | H | H | Cl | CClMePr | O | Et | H | |
| 1-1190 | H | H | H | Cl | CClMePr | O | Pr-i | H | |
| 1-1191 | H | H | H | Cl | CClMePr | S | Me | H | |
| 1-1192 | H | H | H | Cl | CClMePr | NH | Me | H | |
| 1-1193 | H | H | H | Cl | CH(OMe)Me | O | Et | H | |
| 1-1194 | H | H | H | Cl | CH(OMe)Me | O | Pr-i | H | |
| 1-1195 | H | H | H | Cl | CH(OMe)Me | S | Me | H | |
| 1-1196 | H | H | H | Cl | CH(OMe)Me | NH | Me | H | |
| 1-1197 | H | H | H | Cl | C(OMe)Me₂ | O | Et | H | |
| 1-1198 | H | H | H | Cl | C(OMe)Me₂ | O | Pr-i | H | |
| 1-1199 | H | H | H | Cl | C(OMe)Me₂ | S | Me | H | |
| 1-1200 | H | H | H | Cl | C(OMe)Me₂ | NH | Me | H | |

TABLE 39

| Compound No. | X¹ | X² | X³ | X⁴ | Y | G | R¹ | R² | m.p. (° C.) |
|---|---|---|---|---|---|---|---|---|---|
| 1-1201 | H | H | H | Cl | C(OMe)MeEt | O | Et | H | |
| 1-1202 | H | H | H | Cl | C(OMe)MeEt | O | Pr-i | H | |
| 1-1203 | H | H | H | Cl | C(OMe)MeEt | S | Me | H | |
| 1-1204 | H | H | H | Cl | C(OMe)MeEt | NH | Me | H | |
| 1-1205 | H | H | H | Cl | C(OMe)MePr | O | Et | H | |
| 1-1206 | H | H | H | Cl | C(OMe)MePr | O | Pr-i | H | |
| 1-1207 | H | H | H | Cl | C(OMe)MePr | S | Me | H | |
| 1-1208 | H | H | H | Cl | C(OMe)MePr | NH | Me | H | |
| 1-1209 | H | H | H | Cl | SiMe₃ | O | Et | H | |
| 1-1210 | H | H | H | Cl | SiMe₃ | O | Pr-i | H | |
| 1-1211 | H | H | H | Cl | SiMe₃ | S | Me | H | |
| 1-1212 | H | H | H | Cl | SiMe₃ | NH | Me | H | 140–143 |
| 1-1213 | H | H | H | Cl | SiEt₃ | O | Et | H | |
| 1-1214 | H | H | H | Cl | SiEt₃ | O | Pr-i | H | |
| 1-1215 | H | H | H | Cl | SiEt₃ | S | Me | H | |
| 1-1216 | H | H | H | Cl | SiEt₃ | NH | Me | H | |
| 1-1217 | H | H | H | Cl | CF₃ | O | Et | H | |
| 1-1218 | H | H | H | Cl | CF₃ | O | Pr-i | H | |
| 1-1219 | H | H | H | Cl | CF₃ | S | Me | H | |
| 1-1220 | H | H | H | Cl | CF₃ | NH | Me | H | |
| 1-1221 | H | H | H | Me | Et | O | Et | H | |

TABLE 39-continued

| Compound No. | X¹ | X² | X³ | X⁴ | Y | G | R¹ | R² | m.p. (° C.) |
|---|---|---|---|---|---|---|---|---|---|
| 1-1222 | H | H | H | Me | Et | O | Pr-i | H | |
| 1-1223 | H | H | H | Me | Et | S | Me | H | |
| 1-1224 | H | H | H | Me | Et | NH | Me | H | |
| 1-1225 | H | H | H | Me | Pr-i | O | Et | H | |
| 1-1226 | H | H | H | Me | Pr-i | O | Pr-i | H | |
| 1-1227 | H | H | H | Me | Pr-i | S | Me | H | |
| 1-1228 | H | H | H | Me | Pr-i | NH | Me | H | |
| 1-1229 | H | H | H | Me | CH(Me)Pr | O | Et | H | |
| 1-1230 | H | H | H | Me | CH(Me)Pr | O | Pr-i | H | |
| 1-1231 | H | H | H | Me | CH(Me)Pr | S | Me | H | |
| 1-1232 | H | H | H | Me | CH(Me)Pr | NH | Me | H | |
| 1-1233 | H | H | H | Me | C(Me)=CH₂ | O | Et | H | |

TABLE 40

| Compound No. | X¹ | X² | X³ | X⁴ | Y | G | R¹ | R² | m.p. (° C.) |
|---|---|---|---|---|---|---|---|---|---|
| 1-1234 | H | H | H | Me | C(Me)=CH₂ | O | Pr-i | H | |
| 1-1235 | H | H | H | Me | C(Me)=CH₂ | S | Me | H | |
| 1-1236 | H | H | H | Me | C(Me)=CH₂ | NH | Me | H | |
| 1-1237 | H | H | H | Me | CHClMe | O | Et | H | |
| 1-1238 | H | H | H | Me | CHClMe | O | Pr-i | H | |
| 1-1239 | H | H | H | Me | CHClMe | S | Me | H | |
| 1-1240 | H | H | H | Me | CHClMe | NH | Me | H | |
| 1-1241 | H | H | H | Me | CClMe₂ | O | Et | H | |
| 1-1242 | H | H | H | Me | CClMe₂ | O | Pr-i | H | |
| 1-1243 | H | H | H | Me | CClMe₂ | S | Me | H | |
| 1-1244 | H | H | H | Me | CClMe₂ | NH | Me | H | |
| 1-1245 | H | H | H | Me | CClMePr | O | Et | H | |
| 1-1246 | H | H | H | Me | CClMePr | O | Pr-i | H | |
| 1-1247 | H | H | H | Me | CClMePr | S | Me | H | |
| 1-1248 | H | H | H | Me | CClMePr | NH | Me | H | |
| 1-1249 | H | H | H | Me | C(OMe)Me₂ | O | Et | H | |
| 1-1250 | H | H | H | Me | C(OMe)Me₂ | O | Pr-i | H | |
| 1-1251 | H | H | H | Me | C(OMe)Me₂ | S | Me | H | |
| 1-1252 | H | H | H | Me | C(OMe)Me₂ | NH | Me | H | |
| 1-1253 | H | H | H | Me | SiMe₃ | O | Et | H | |
| 1-1254 | H | H | H | Me | SiMe₃ | O | Pr-i | H | |
| 1-1255 | H | H | H | Me | SiMe₃ | S | Me | H | |
| 1-1256 | H | H | H | Me | SiMe₃ | NH | Me | H | |
| 1-1257 | H | H | H | Me | SiEt₃ | O | Et | H | |
| 1-1258 | H | H | H | Me | SiEt₃ | O | Pr-i | H | |
| 1-1259 | H | H | H | Me | SiEt₃ | S | Me | H | |
| 1-1260 | H | H | H | Me | SiEt₃ | NH | Me | H | |
| 1-1261 | H | H | H | Me | CF₃ | O | Et | H | |
| 1-1262 | H | H | H | Me | CF₃ | O | Pr-i | H | |
| 1-1263 | H | H | H | Me | CF₃ | S | Me | H | |

TABLE 41

| Compound No. | X¹ | X² | X³ | X⁴ | Y | G | R¹ | R² | m.p. (° C.) |
|---|---|---|---|---|---|---|---|---|---|
| 1-1264 | H | H | H | Me | CF₃ | NH | Me | H | |
| 1-4265 | Cl | H | H | F | H | O | Me | H | |
| 1-1266 | Cl | H | H | F | Me | O | Me | H | |
| 1-1267 | Cl | H | H | F | Et | O | Me | H | |
| 1-1268 | Cl | H | H | F | Pr | O | Me | H | |
| 1-1269 | Cl | H | H | F | Pr-i | O | Me | H | |
| 1-1270 | Cl | H | H | F | Bu | O | Me | H | |
| 1-1271 | Cl | H | H | F | Bu-i | O | Me | H | |
| 1-1272 | Cl | H | H | F | Bu-s | O | Me | H | |
| 1-1273 | Cl | H | H | F | Bu-t | O | Me | H | Oily |
| 1-1274 | Cl | H | H | F | C₅H₁₁ | O | Me | H | |
| 1-1275 | Cl | H | H | F | CHMePr | O | Me | H | |
| 1-1276 | Cl | H | H | F | CH₂C₂CH₂Pr-i | O | Me | H | |
| 1-1277 | Cl | H | H | F | CH₂CH(Me)CH₂Me | O | Me | H | |
| 1-1278 | Cl | H | H | F | C₆H₁₃ | O | Me | H | |
| 1-1279 | Cl | H | H | F | C₃H₅-c | O | Me | H | |
| 1-1280 | Cl | H | H | F | C₅H₉-c | O | Me | H | |
| 1-1281 | Cl | H | H | F | CH=CH₂ | O | Me | H | |
| 1-1282 | Cl | H | H | F | C(Me)=CH₂ | O | Me | H | |
| 1-1283 | Cl | H | H | F | C(Me)=CHMe | O | Me | H | |
| 1-1284 | Cl | H | H | F | CH₂CH=CH₂ | O | Me | H | |

TABLE 41-continued

| Compound No. | $X^1$ | $X^2$ | $X^3$ | $X^4$ | Y | G | $R^1$ | $R^2$ | m.p. (° C.) |
|---|---|---|---|---|---|---|---|---|---|
| 1-1285 | Cl | H | H | F | 1-methylcyclohex-1-enyl | O | Me | H | |
| 1-1286 | Cl | H | H | F | CHClMe | O | Me | H | |
| 1-1287 | Cl | H | H | F | CHClEt | O | Me | H | |
| 1-1288 | Cl | H | H | F | CHClPr | O | Me | H | |
| 1-1289 | Cl | H | H | F | CHClPr-i | O | Me | H | |
| 1-1290 | Cl | H | H | F | CH$_2$CHClMe | O | Me | H | |
| 1-1291 | Cl | H | H | F | CClMe$_2$ | O | Me | H | |
| 1-1292 | Cl | H | H | F | CClMeEt | O | Me | H | |
| 1-1293 | Cl | H | H | F | CClMePr | O | Me | H | |
| 1-1294 | Cl | H | H | F | CClMeBu-t | O | Me | H | |
| 1-1295 | Cl | H | H | F | CClMePh | O | Me | H | |
| 1-1296 | Cl | H | H | F | CHClPh | O | Me | H | |

TABLE 42

| Compound No. | $X^1$ | $X^2$ | $X^3$ | $X^4$ | Y | G | $R^1$ | $R^2$ | m.p. (° C.) |
|---|---|---|---|---|---|---|---|---|---|
| 1-1297 | Cl | H | H | F | CH(OMe)Me | O | Me | H | |
| 1-1298 | Cl | H | H | F | CH(OMe)Et | O | Me | H | |
| 1-1299 | Cl | H | H | F | CH(OMe)Pr | O | Me | H | |
| 1-1300 | Cl | H | H | F | CH(OMe)Pr-i | O | Me | H | |
| 1-1301 | Cl | H | H | F | CH$_2$CH(OMe)Me | O | Me | H | |
| 1-1302 | Cl | H | H | F | C(OMe)Me$_2$ | O | Me | H | |
| 1-1303 | Cl | H | H | F | C(OMe)MeEt | O | Me | H | |
| 1-1304 | Cl | H | H | F | C(OMe)MePr | O | Me | H | |
| 1-1305 | Cl | H | H | F | C(OMe)MeBu-t | O | Me | H | |
| 1-1306 | Cl | H | H | F | C(OMe)MePh | O | Me | H | |
| 1-1307 | Cl | H | H | F | CH(OMe)Ph | O | Me | H | |
| 1-1308 | Cl | H | H | F | SiMe$_3$ | O | Me | H | |
| 1-1309 | Cl | H | H | F | SiEt$_3$ | O | Me | H | |
| 1-1310 | Cl | H | H | F | CH$_2$Ph | O | Me | H | |
| 1-1311 | Cl | H | H | F | CF$_3$ | O | Me | H | |
| 1-1312 | Cl | H | H | F | COMe | O | Me | H | |
| 1-1313 | Cl | H | H | F | COOMe | O | Me | H | |
| 1-1314 | H | H | Cl | Cl | H | O | Me | H | |
| 1-1315 | H | H | Cl | Cl | Pr-i | O | Me | H | |
| 1-1316 | H | H | Cl | Cl | Bu | O | Me | H | |
| 1-1317 | H | H | Cl | Cl | CHMeEt | O | Me | H | |
| 1-1318 | H | H | Cl | Cl | Bu-t | O | Me | H | Oily |
| 1-1319 | H | H | Cl | Cl | C$_5$H$_{11}$ | O | Me | H | |
| 1-1320 | H | H | Cl | Cl | C$_5$H$_9$-c | O | Me | H | |
| 1-1321 | H | H | Cl | Cl | CH$_2$-C$_5$H$_9$-c | O | Me | H | |
| 1-1322 | H | H | Cl | Cl | C(OMe)Me$_2$ | O | Me | H | |
| 1-1323 | H | H | Cl | Cl | SiMe$_3$ | O | Me | H | |
| 1-1324 | H | H | Me | Cl | Pr-i | O | Me | H | |
| 1-1325 | H | H | Me | Cl | Bu | O | Me | H | Oily |
| 1-1326 | H | H | Me | Cl | CHMeEt | O | Me | H | |
| 1-1327 | H | H | Me | Cl | Bu-t | O | Me | H | Oily |
| 1-1328 | H | H | Me | Cl | C$_5$H$_{11}$ | O | Me | H | |
| 1-1329 | H | H | Me | Cl | C$_5$H$_9$-c | O | Me | H | |

TABLE 43

| Compound No. | $X^1$ | $X^2$ | $X^3$ | $X^4$ | Y | G | $R^1$ | $R^2$ | m.p. (° C.) |
|---|---|---|---|---|---|---|---|---|---|
| 1-1330 | H | H | Me | Cl | CH$_2$—C$_5$H$_9$-c | O | Me | H | Oily |
| 1-1331 | H | H | Me | Cl | C(()Me)Me$_2$ | O | Me | H | Oily |
| 1-1332 | H | H | Me | Cl | SiMe$_3$ | O | Me | H | Oily |
| 1-1333 | H | H | Cl | Me | Pr-i | O | Me | H | |
| 1-1334 | H | H | Cl | Me | Bu | O | Me | H | |
| 1-1335 | H | H | Cl | Me | CHMeEt | O | Me | H | |
| 1-1336 | H | H | Cl | Me | Bu-t | O | Me | H | 57–60 |

TABLE 43-continued

| Compound No. | X¹ | X² | X³ | X⁴ | Y | G | R¹ | R² | m.p. (° C.) |
|---|---|---|---|---|---|---|---|---|---|
| 1-1337 | H | H | Cl | Me | $C_5H_{11}$ | O | Me | H | |
| 1-1338 | H | H | Cl | Me | $C_5H_9$-c | O | Me | H | |
| 1-1339 | H | H | Cl | Me | $CH_2-C_5H_9$-c | O | Me | H | |
| 1-1340 | H | H | Cl | Me | $C(OMe)Me_2$ | O | Me | H | |
| 1-1341 | H | H | Cl | Me | $SiMe_3$ | O | Me | H | |
| 1-1342 | H | H | Me | Me | Pr-i | O | Me | H | |
| 1-1343 | H | H | Me | Me | Bu | O | Me | H | |
| 1-1344 | H | H | Me | Me | CHMeEt | O | Me | H | |
| 1-1345 | H | H | Me | Me | Bu-t | O | Me | H | Oily |
| 1-1346 | H | H | Me | Me | $C_5H_{11}$ | O | Me | H | |
| 1-1347 | H | H | Me | Me | $C_5H_9$-c | O | Me | H | |
| 1-1348 | H | H | Me | Me | $CH_2-C_5H_9$-c | O | Me | H | |
| 1-1349 | H | H | Me | Me | $C(OMe)Me_2$ | O | Me | H | |
| 1-1350 | H | H | Me | Me | $SiMe_3$ | O | Me | H | |
| 1-1351 | H | H | OMe | Cl | Pr-i | O | Me | H | |
| 1-1352 | H | H | OMe | Cl | Bu | O | Me | H | |
| 1-1353 | H | H | OMe | Cl | CHMeEt | O | Me | H | |
| 1-1354 | H | H | OMe | Cl | Bu-t | O | Me | H | |
| 1-1355 | H | H | OMe | Cl | $C_5H_{11}$ | O | Me | H | |
| 1-1356 | H | H | OMe | Cl | $C_5H_9$-c | O | Me | H | |
| 1-1357 | H | H | OMe | Cl | $CH_2-C_5H_9$-c | O | Me | H | |
| 1-1358 | H | H | OMe | Cl | $C(OMe)Me_2$ | O | Me | H | |
| 1-1359 | H | H | OMe | Cl | $SiMe_3$ | O | Me | H | |
| 1-1360 | H | H | Cl | OMe | Pr-i | O | Me | H | |
| 1-1361 | H | H | Cl | OMe | Bu | O | Me | H | |

TABLE 44

| Compound No. | X¹ | X² | X³ | X⁴ | Y | G | R¹ | R² | m.p. (° C.) |
|---|---|---|---|---|---|---|---|---|---|
| 1-1362 | H | H | Cl | OMe | CHMeEt | O | Me | H | |
| 1-1363 | H | H | Cl | OMe | Bu-t | O | Me | H | Oily |
| 1-1364 | H | H | Cl | OMe | $C_5H_{11}$ | O | Me | H | |
| 1-1365 | H | H | Cl | OMe | $C_5H_9$-c | O | Me | H | |
| 1-1366 | H | H | Cl | OMe | $CH_2-C_5H_9$-c | O | Me | H | |
| 1-1367 | H | H | Cl | OMe | $C(OMe)Me_2$ | O | Me | H | |
| 1-1368 | H | H | Cl | OMe | $SiMe_3$ | O | Me | H | |
| 1-1369 | H | H | Me | OMe | Pr-i | O | Me | H | |
| 1-1370 | H | H | Me | OMe | Bu | O | Me | H | |
| 1-1371 | H | H | Me | OMe | CHMeEt | O | Me | H | |
| 1-1372 | H | H | Me | OMe | Bu-t | O | Me | H | Oily |
| 1-1373 | H | H | Me | OMe | $C_5H_{11}$ | O | Me | H | |
| 1-1374 | H | H | Me | OMe | $C_5H_9$-c | O | Me | H | |
| 1-1375 | H | H | Me | OMe | $CH_2-C_5H_9$-c | O | Me | H | |
| 1-1376 | H | H | Me | OMe | $C(OMe)Me_2$ | O | Me | H | |
| 1-1377 | H | H | Me | OMe | $SiMe_3$ | O | Me | H | |
| 1-1378 | H | H | OMe | Me | Pr-i | O | Me | H | |
| 1-1379 | H | H | OMe | Me | Bu | O | Me | H | |
| 1-1380 | H | H | OMe | Me | CHMeEt | O | Me | H | |
| 1-1381 | H | H | OMe | Me | Bu-t | O | Me | H | |
| 1-1382 | H | H | OMe | Me | $C_5H_{11}$ | O | Me | H | |
| 1-1383 | H | H | OMe | Me | $C_5H_9$-c | O | Me | H | |
| 1-1384 | H | H | OMe | Me | $CH_2-C_5H_9$-c | O | Me | H | |
| 1-1385 | H | H | OMe | Me | $C(OMe)Me_2$ | O | Me | H | |
| 1-1386 | H | H | OMe | Me | $SiMe_3$ | O | Me | H | |
| 1-1387 | H | Cl | H | Cl | H | O | Me | H | 92–95 |
| 1-1388 | H | Cl | H | Cl | Pr-i | O | Me | H | |
| 1-1389 | H | Cl | H | Cl | Bu | O | Me | H | |
| 1-1390 | H | Cl | H | Cl | CHMeEt | O | Me | H | |
| 1-1391 | H | Cl | H | Cl | Bu-t | O | Me | H | Oily |
| 1-1392 | H | Cl | H | Cl | $C_5H_{11}$ | O | Me | H | |
| 1-1393 | H | Cl | H | Cl | $C_5H_9$-c | O | Me | H | |

TABLE 45

| Compound No. | $X^1$ | $X^2$ | $X^3$ | $X^4$ | Y | G | $R^1$ | $R^2$ | m.p. (° C.) |
|---|---|---|---|---|---|---|---|---|---|
| 1-1394 | H | Cl | H | Cl | $CH_2$—$C_5H_9$-c | O | Me | H | |
| 1-1395 | H | Cl | H | Cl | $C(OMe)Me_2$ | O | Me | H | |
| 1-1396 | H | Cl | H | Cl | $SiMe_3$ | O | Me | H | Oily |
| 1-1397 | H | OMe | H | Cl | Pr-i | O | Me | H | |
| 1-1398 | H | OMe | H | Cl | Bu | O | Me | H | |
| 1-1399 | H | OMe | H | Cl | CHMeEt | O | Me | H | |
| 1-1400 | H | OMe | H | Cl | Bu-t | O | Me | H | Oily |
| 1-1401 | H | OMe | H | Cl | $C_5H_{11}$ | O | Me | H | |
| 1-1402 | H | OMe | H | Cl | $C_5H_9$-c | O | Me | H | |
| 1-1403 | H | OMe | H | Cl | $CH_2$—$C_5H_9$-c | O | Me | H | |
| 1-1404 | H | OMe | H | Cl | $C(OMe)Me_2$ | O | Me | H | |
| 1-1405 | H | OMe | H | Cl | $SiMe_3$ | O | Me | H | |
| 1-1406 | H | Me | H | Me | Pr-i | O | Me | H | |
| 1-1407 | H | Me | H | Me | Bu | O | Me | H | |
| 1-1408 | H | Me | H | Me | CHMeEt | O | Me | H | |
| 1-1409 | H | Me | H | Me | Bu-t | O | Me | H | Oily |
| 1-1410 | H | Me | H | Me | $C_5H_{11}$ | O | Me | H | |
| 1-1411 | H | Me | H | Me | $C_5H_9$-c | O | Me | H | |
| 1-1412 | H | Me | H | Me | $CH_2$—$C_5H_9$-c | O | Me | H | |
| 1-1413 | H | Me | H | Me | $C(OMe)Me_2$ | O | Me | H | |
| 1-1414 | H | Me | H | Me | $SiMe_3$ | O | Me | H | |
| 1-1415 | H | H | H | Cl | $CH_2F$ | O | Me | H | Oily |
| 1-1416 | H | H | H | Cl | $CHF_2$ | O | Me | H | Oily |
| 1-1417 | H | H | H | Cl | $CF(Et)_2$ | O | Me | H | Oily |
| 1-1418 | H | H | H | Cl | $CFMeCHMe_2$ | O | Me | H | 64–67 |
| 1-1419 | H | H | H | Cl | $CHFCH_2CHMe_2$ | O | Me | H | Oily |
| 1-1420 | H | H | H | Cl | $CH_2CH_2CHMe_2$ | O | Me | H | Oily |
| 1-1421 | H | H | H | Cl | $CH(Me)CHMe_2$ | O | Me | H | Oily |
| 1-1422 | H | H | H | Cl | $CHEt_2$ | O | Me | H | Oily |
| 1-1423 | H | H | H | Cl | $CH(Me)OEt$ | O | Me | H | Oily |
| 1-1424 | H | H | H | Cl | $CH(Me)OCHMe_2$ | O | Me | H | Oily |

TABLE 46

| Compound No. | $X^1$ | $X^2$ | $X^3$ | $X^4$ | Y | G | $R^1$ | $R^2$ | m.p. (° C.) |
|---|---|---|---|---|---|---|---|---|---|
| 1-1425 | H | H | H | Cl | $CMe(OMe)CHMe_2$ | O | Me | H | Oily |
| 1-1426 | H | H | H | Cl | $CH(OMe)CH_2CHMe_2$ | O | Me | H | Oily |
| 1-1427 | H | H | H | Cl | $CH(OEt)_2$ | O | Me | H | 54-57 |
| 1-1428 | H | H | H | Cl | $CH_2SiMe_3$ | O | Me | H | Oily |
| 1-1429 | H | H | H | Cl | COOBu-t | O | Me | H | Oily |
| 1-1430 | H | H | H | Cl | Bu-t | O | Et | H | Oily |
| 1-1431 | H | H | H | Cl | Bu-t | O | Pr-i | H | Oily |

TABLE 47

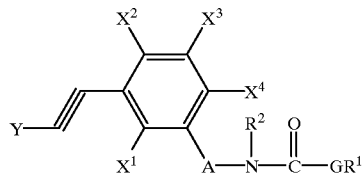

| Compound No. | $X^1$ | $X^2$ | $X^3$ | $X^4$ | Y | A | G | $R^1$ | $R^2$ | m.p. (° C.) |
|---|---|---|---|---|---|---|---|---|---|---|
| 2-1 | H | H | H | Me | Pr-i | CHMe | O | Me | H | |
| 2-2 | H | H | H | Me | Bu-t | CHMe | O | Me | H | |
| 2-3 | H | H | H | Me | CHMePr | CHMe | O | Me | H | |
| 2-4 | H | H | H | Me | $C(Me)$=$CH_2$ | CHMe | O | Me | H | |
| 2-5 | H | H | H | Me | CHClMe | CHMe | O | Me | H | |
| 2-6 | H | H | H | Me | $CClMe_2$ | CHMe | O | Me | H | |
| 2-7 | H | H | H | Me | CClMePr | CHMe | O | Me | H | |
| 2-8 | H | H | H | Me | $C(OMe)Me_2$ | CHMe | O | Me | H | |
| 2-9 | H | H | H | Me | $SiMe_3$ | CHMe | O | Me | H | |
| 2-10 | H | H | H | Me | $SiEt_3$ | CHMe | O | Me | H | |

TABLE 47-continued

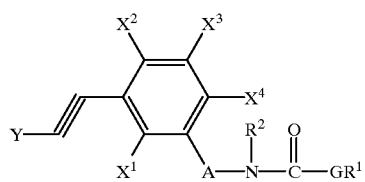

| Compound No. | $X^1$ | $X^2$ | $X^3$ | $X^4$ | Y | A | G | $R^1$ | $R^2$ | m.p. (° C.) |
|---|---|---|---|---|---|---|---|---|---|---|
| 2-11 | H | H | H | Me | $CF_3$ | CHMe | O | Me | H | |
| 2-12 | H | H | H | H | Me | CHMe | O | Me | H | |
| 2-13 | H | H | H | H | Et | CHMe | O | Me | H | |
| 2-14 | H | H | H | H | Pr-i | CHMe | O | Me | H | |
| 2-15 | H | H | H | H | Bu-t | CHMe | O | Me | H | |
| 2-16 | H | H | H | H | $C(Me)=CH_2$ | CHMe | O | Me | H | |
| 2-17 | H | H | H | H | CH(OH)Et | CHMe | O | Me | H | |
| 2-18 | H | H | H | H | CHClMe | CHMe | O | Me | H | |
| 2-19 | H | H | H | H | CHClEt | CHMe | O | Me | H | |
| 2-20 | H | H | H | H | $CClMe_2$ | CHMe | O | Me | H | |
| 2-21 | H | H | H | H | CClMeEt | CHMe | O | Me | H | |
| 2-22 | H | H | H | H | CH(OMe)Me | CHMe | O | Me | H | |
| 2-23 | H | H | H | H | $C(OMe)Me_2$ | CHMe | O | Me | H | |
| 2-24 | H | H | H | H | C(OMe)MeEt | CHMe | O | Me | H | |
| 2-25 | H | H | H | H | $SiMe_3$ | CHMe | O | Me | H | |
| 2-26 | H | H | H | H | $SiEt_3$ | CHMe | O | Me | H | |

TABLE 48

| Compound No. | $X^1$ | $X^2$ | $X^3$ | $X^4$ | Y | A | G | $R^1$ | $R^2$ | m.p. (° C.) |
|---|---|---|---|---|---|---|---|---|---|---|
| 2-27 | H | H | H | F | Me | CHMe | O | Me | H | |
| 2-28 | H | H | H | F | Et | CHMe | O | Me | H | |
| 2-29 | H | H | H | F | Pr-i | CHMe | O | Me | H | |
| 2-30 | H | H | H | F | Bu-t | CHMe | O | Me | H | Oily |
| 2-31 | H | H | H | F | $C(Me)=CH_2$ | CHMe | O | Me | H | |
| 2-32 | H | H | H | F | CH(OH)Et | CHMe | O | Me | H | |
| 2-33 | H | H | H | F | CHClMe | CHMe | O | Me | H | |
| 2-34 | H | H | H | F | CHClEt | CHMe | O | Me | H | |
| 2-35 | H | H | H | F | $CClMe_2$ | CHMe | O | Me | H | |
| 2-36 | H | H | H | F | CClMeEt | CHMe | O | Me | H | |
| 2-37 | H | H | H | F | CH(OMe)Me | CHMe | O | Me | H | |
| 2-38 | H | H | H | F | $C(OMe)Me_2$ | CHMe | O | Me | H | |
| 2-39 | H | H | H | F | C(OMe)MeEt | CHMe | O | Me | H | |
| 2-40 | H | H | H | F | $SiMe_3$ | CHMe | O | Me | H | |
| 2-41 | H | H | H | F | $SiEt_3$ | CHMe | O | Me | H | |
| 2-42 | H | H | H | Cl | Pr-i | CHMe | O | Me | H | |
| 2-43 | H | H | H | Cl | Bu-t | CHMe | O | Me | H | 98–101 |
| 2-44 | H | H | H | Cl | $C(Me)=CH_2$ | CHMe | O | Me | H | |
| 2-45 | H | H | H | Cl | CHClEt | CHMe | O | Me | H | |
| 2-46 | H | H | H | Cl | $CClMe_2$ | CHMe | O | Me | H | |
| 2-47 | H | H | H | Cl | CClMePr | CHMe | O | Me | H | |
| 2-48 | H | H | H | Cl | CH(OMe)Me | CHMe | O | Me | H | |
| 2-49 | H | H | H | Cl | $C(OMe)Me_2$ | CHMe | O | Me | H | |
| 2-50 | H | H | H | Cl | C(OMe)MeEt | CHMe | O | Me | H | |
| 2-51 | H | H | H | Cl | C(OMe)MePr | CHMe | O | Me | H | |
| 2-52 | H | H | H | Cl | $SiMe_3$ | CHMe | O | Me | H | |
| 2-53 | H | H | H | Cl | $SiEt_3$ | CHMe | O | Me | H | |
| 2-54 | H | H | H | Cl | $CF_3$ | CHMe | O | Me | H | |
| 2-55 | H | H | H | Me | Pr-i | CHEt | O | Me | H | |
| 2-56 | H | H | H | Me | Bu-t | CHEt | O | Me | H | |
| 2-57 | H | H | H | Me | CHMePr | CHEt | O | Me | H | |

TABLE 49

| Compound No. | $X^1$ | $X^2$ | $X^3$ | $X^4$ | Y | A | G | $R^1$ | $R^2$ | m.p. (° C.) |
|---|---|---|---|---|---|---|---|---|---|---|
| 2-58 | H | H | H | Me | $C(Me)=CH_2$ | CHEt | O | Me | H | |
| 2-59 | H | H | H | Me | CHClMe | CHEt | O | Me | H | |
| 2-60 | H | H | H | Me | $CClMe_2$ | CHEt | O | Me | H | |
| 2-61 | H | H | H | Me | CClMePr | CHEt | O | Me | H | |
| 2-62 | H | H | H | Me | $C(OMe)Me_2$ | CHEt | O | Me | H | |

TABLE 49-continued

| Compound No. | X¹ | X² | X³ | X⁴ | Y | A | G | R¹ | R² | m.p. (° C.) |
|---|---|---|---|---|---|---|---|---|---|---|
| 2-63 | H | H | H | Me | SiMe$_3$ | CHEt | O | Me | H | |
| 2-64 | H | H | H | Me | SiEt$_3$ | CHEt | O | Me | H | |
| 2-65 | H | H | H | Me | CF$_3$ | CHEt | O | Me | H | |
| 2-66 | H | H | H | H | Me | CHEt | O | Me | H | |
| 2-67 | H | H | H | H | Et | CHEt | O | Me | H | |
| 2-68 | H | H | H | H | Pr-i | CHEt | O | Me | H | |
| 2-69 | H | H | H | H | Bu-t | CHEt | O | Me | H | |
| 2-70 | H | H | H | H | C(Me)=CH$_2$ | CHEt | O | Me | H | |
| 2-71 | H | H | H | H | CH(OH)Et | CHEt | O | Me | H | |
| 2-72 | H | H | H | H | CHClMe | CHEt | O | Me | H | |
| 2-73 | H | H | H | H | CHClEt | CHEt | O | Me | H | |
| 2-74 | H | H | H | H | CClMe$_2$ | CHEt | O | Me | H | |
| 2-75 | H | H | H | H | CClMeEt | CHEt | O | Me | H | |
| 2-76 | H | H | H | H | CH(OMe)Me | CHEt | O | Me | H | |
| 2-77 | H | H | H | H | C(OMe)Me$_2$ | CHEt | O | Me | H | |
| 2-78 | H | H | H | H | C(OMe)MeEt | CHEt | O | Me | H | |
| 2-79 | H | H | H | H | SiMe$_3$ | CHEt | O | Me | H | |
| 2-80 | H | H | H | H | SiEt$_3$ | CHEt | O | Me | H | |
| 2-81 | H | H | H | F | Me | CHEt | O | Me | H | |
| 2-82 | H | H | H | F | Et | CHEt | O | Me | H | |
| 2-83 | H | H | H | F | Pr-i | CHEt | O | Me | H | |
| 2-84 | H | H | H | F | Bu-t | CHEt | O | Me | H | |
| 2-85 | H | H | H | F | C(Me)=CH$_2$ | CHEt | O | Me | H | |
| 2-86 | H | H | H | F | CH(OH)Et | CHEt | O | Me | H | |
| 2-87 | H | H | H | F | CHClMe | CHEt | O | Me | H | |
| 2-88 | H | H | H | F | CHClEt | CHEt | O | Me | H | |

TABLE 50

| Compound No. | X¹ | X² | X³ | X⁴ | Y | A | G | R¹ | R² | m.p. (° C.) |
|---|---|---|---|---|---|---|---|---|---|---|
| 2-89 | H | H | H | F | CClMe$_2$ | CHEt | O | Me | H | |
| 2-90 | H | H | H | F | CClMeEt | CHEt | O | Me | H | |
| 2-91 | H | H | H | F | CH(OMe)Me | CHEt | O | Me | H | |
| 2-92 | H | H | H | F | C(OMe)Me$_2$ | CHEt | O | Me | H | |
| 2-93 | H | H | H | F | C(OMe)MeEt | CHEt | O | Me | H | |
| 2-94 | H | H | H | F | SiMe$_3$ | CHEt | O | Me | H | |
| 2-95 | H | H | H | F | SiEt$_3$ | CHEt | O | Me | H | |
| 2-96 | H | H | H | Cl | Pr-i | CHEt | O | Me | H | |
| 2-97 | H | H | H | Cl | Bu-t | CHEt | O | Me | H | 121–124 |
| 2-98 | H | H | H | Cl | C(Me)=CH$_2$ | CHEt | O | Me | H | |
| 2-99 | H | H | H | Cl | CHClEt | CHEt | O | Me | H | |
| 2-100 | H | H | H | Cl | CClMe$_2$ | CHEt | O | Me | H | |
| 2-101 | H | H | H | Cl | CClMePr | CHEt | O | Me | H | |
| 2-102 | H | H | H | Cl | CH(OMe)Me | CHEt | O | Me | H | |
| 2-103 | H | H | H | Cl | C(OMe)Me$_2$ | CHEt | O | Me | H | |
| 2-104 | H | H | H | Cl | C(OMe)MeEt | CHEt | O | Me | H | |
| 2-105 | H | H | H | Cl | C(OMe)MePr | CHEt | O | Me | H | |
| 2-106 | H | H | H | Cl | SiMe$_3$ | CHEt | O | Me | H | |
| 2-107 | H | H | H | Cl | SiEt$_3$ | CHEt | O | Me | H | |
| 2-108 | H | H | H | Cl | CF$_3$ | CHEt | O | Me | H | |
| 2-109 | H | H | H | Me | Pr-i | CMe$_2$ | O | Me | H | |
| 2-110 | H | H | H | Me | Bu-t | CMe$_2$ | O | Me | H | |
| 2-111 | H | H | H | Me | CHMePr | CMe$_2$ | O | Me | H | |
| 2-112 | H | H | H | Me | C(Me)=CH$_2$ | CMe$_2$ | O | Me | H | |
| 2-113 | H | H | H | Me | CHClMe | CMe$_2$ | O | Me | H | |
| 2-114 | H | H | H | Me | CClMe$_2$ | CMe$_2$ | O | Me | H | |
| 2-115 | H | H | H | Me | CClMePr | CMe$_2$ | O | Me | H | |
| 2-116 | H | H | H | Me | C(OMe)Me$_2$ | CMe$_2$ | O | Me | H | |
| 2-117 | H | H | H | Me | SiMe$_3$ | CMe$_2$ | O | Me | H | |
| 2-118 | H | H | H | Me | SiEt$_3$ | CMe$_2$ | O | Me | H | |

TABLE 51

| Compound No. | X¹ | X² | X³ | X⁴ | Y | A | G | R¹ | R² | m.p. (° C.) |
|---|---|---|---|---|---|---|---|---|---|---|
| 2-119 | H | H | H | Me | CF$_3$ | CMe$_2$ | O | Me | H | |
| 2-120 | H | H | H | H | Me | CMe$_2$ | O | Me | H | |
| 2-121 | H | H | H | H | Et | CMe$_2$ | O | Me | H | |
| 2-122 | H | H | H | H | Pr-i | CMe$_2$ | O | Me | H | |
| 2-123 | H | H | H | H | Bu-t | CMe$_2$ | O | Me | H | |
| 2-124 | H | H | H | H | C(Me)=CH$_2$ | CMe$_2$ | O | Me | H | |

TABLE 51-continued

| Compound No. | $X^1$ | $X^2$ | $X^3$ | $X^4$ | Y | A | G | $R^1$ | $R^2$ | m.p. (° C.) |
|---|---|---|---|---|---|---|---|---|---|---|
| 2-125 | H | H | H | H | CH(OH)Et | $CMe_2$ | O | Me | H | |
| 2-126 | H | H | H | H | CHClMe | $CMe_2$ | O | Me | H | |
| 2-127 | H | H | H | H | CHClEt | $CMe_2$ | O | Me | H | |
| 2-128 | H | H | H | H | $CClMe_2$ | $CMe_2$ | O | Me | H | |
| 2-129 | H | H | H | H | CClMeEt | $CMe_2$ | O | Me | H | |
| 2-130 | H | H | H | H | CH(OMe)Me | $CMe_2$ | O | Me | H | |
| 2-131 | H | H | H | H | $C(OMe)Me_2$ | $CMe_2$ | O | Me | H | |
| 2-132 | H | H | H | H | C(OMe)MeEt | $CMe_2$ | O | Me | H | |
| 2-133 | H | H | H | H | $SiMe_3$ | $CMe_2$ | O | Me | H | |
| 2-134 | H | H | H | H | $SiEt_3$ | $CMe_2$ | O | Me | H | |
| 2-135 | H | H | H | F | Me | $CMe_2$ | O | Me | H | |
| 2-136 | H | H | H | F | Et | $CMe_2$ | O | Me | H | |
| 2-137 | H | H | H | F | Pr-i | $CMe_2$ | O | Me | H | |
| 2-138 | H | H | H | F | Bu-t | $CMe_2$ | O | Me | H | |
| 2-139 | H | H | H | F | $C(Me)=CH_2$ | $CMe_2$ | O | Me | H | |
| 2-140 | H | H | H | F | CH(OH)Et | $CMe_2$ | O | Me | H | |
| 2-141 | H | H | H | F | CHClMe | $CMe_2$ | O | Me | H | |
| 2-142 | H | H | H | F | CHClEt | $CMe_2$ | O | Me | H | |
| 2-143 | H | H | H | F | $CClMe_2$ | $CMe_2$ | O | Me | H | |
| 2-144 | H | H | H | F | CClMeEt | $CMe_2$ | O | Me | H | |
| 2-145 | H | H | H | F | CH(OMe)Me | $CMe_2$ | O | Me | H | |
| 2-146 | H | H | H | F | $C(OMe)Me_2$ | $CMe_2$ | O | Me | H | |

TABLE 52

| Compound No. | $X^1$ | $X^2$ | $X^3$ | $X^4$ | Y | A | G | $R^1$ | $R^2$ | m.p. (° C.) |
|---|---|---|---|---|---|---|---|---|---|---|
| 2-147 | H | H | H | F | C(OMe)MeEt | $CMe_2$ | O | Me | H | |
| 2-148 | H | H | H | F | $SiMe_3$ | $CMe_2$ | O | Me | H | |
| 2-149 | H | H | H | F | $SiEt_3$ | $CMe_2$ | O | Me | H | |
| 2-150 | H | H | H | Cl | Pr-i | $CMe_2$ | O | Me | H | |
| 2-151 | H | H | H | Cl | Bu-t | $CMe_2$ | O | Me | H | |
| 2-152 | H | H | H | Cl | $C(Me)=CH_2$ | $CMe_2$ | O | Me | H | |
| 2-153 | H | H | H | Cl | CHClEt | $CMe_2$ | O | Me | H | |
| 2-154 | H | H | H | Cl | $CClMe_2$ | $CMe_2$ | O | Me | H | |
| 2-155 | H | H | H | Cl | CClMePr | $CMe_2$ | O | Me | H | |
| 2-156 | H | H | H | Cl | CH(OMe)Me | $CMe_2$ | O | Me | H | |
| 2-157 | H | H | H | Cl | $C(OMe)Me_2$ | $CMe_2$ | O | Me | H | |
| 2-158 | H | H | H | Cl | C(OMe)MeEt | $CMe_2$ | O | Me | H | |
| 2-159 | H | H | H | Cl | C(OMe)MePr | $CMe_2$ | O | Me | H | |
| 2-160 | H | H | H | Cl | $SiMe_3$ | $CMe_2$ | O | Me | H | |
| 2-161 | H | H | H | Cl | $SiEt_3$ | $CMe_2$ | O | Me | H | |
| 2-162 | H | H | H | Cl | $CF_3$ | $CMe_2$ | O | Me | H | |
| 2-163 | H | H | H | Cl | Bu-t | CHPr-i | O | Me | H | Oily |

Typical processes for producing phenylacetylene derivatives represented by the general formula [I] as the compounds of the present invention, will be exemplified below, but not limited thereto.

Process 1

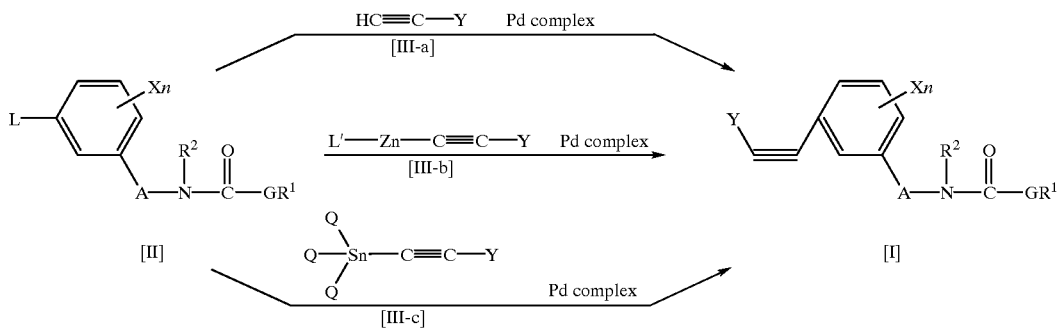

(wherein A, G, $R^1$, $R^2$, X, Y and n have the same meanings as mentioned above respectively, L is a bromine atom, an iodine atom or a $OSO_2CF_3$ group, L' is a halogen atom, and Q is a $C_1$–$C_6$ alkyl group.)

The compound [I] of the present invention can be produced by a known method wherein a compound [II] and a compound [III-a] are reacted in the presence of a Pd complex and a base (e.g. Tetrahedron Letters, vol 50, p4467 (1975), Tetrahedron Letters, vol 34, p6403 (1993), Tetrahedron Letters, vol 37, p5527 (1996), etc.), a known method wherein a compound [II] and a compound [III-b] are reacted in the presence of a Pd complex (The Journal of Organic Chemistry, vol 43, p258 (1978), etc.), or a known method wherein a compound [II] and a compound [III-c] is reacted in the presence of a Pd complex (The Journal of Organic Chemistry, vol 54, p5856 (1989)).

With respect to the amounts of starting compounds to be used in the reactions, based on the compound [II], the compound [III-a] or the compound [III-b] or the compound [III-c] is optionally selected within a range of from 1.0 to 10.0 equivalents, preferably from 1.0 to 3.0 equivalents.

In this process, a solvent may be used in some cases. The solvent may be one which does not hinder the progress of the reaction, and for example, it is possible to use a ketone such as acetone, methyl ethyl ketone or cyclohexanone, an ether such as diethyl ether, diisopropyl ether, tetrahydrofuran, dioxane, dimethoxyethane or diethylene glycol dimethyl ether, an ester such as ethyl acetate or methyl acetate, a halogenated hydrocarbon such as dichloromethane, chloroform or carbon tetrachloride, an aromatic hydrocarbon such as benzene, chlorobenzene, nitrobenzene or toluene, a nitrile such as acetonitrile, N,N-dimethylformamide, N,N-dimethylacetamide, 1,3-dimethyl-2-imidazolinone, dimethyl sulfoxide, or water. These inert solvents may be used alone or as mixed.

As the base to be used in the reaction employing the compound [III-a] in this process, it is possible to employ, for example, an inorganic salt such as sodium carbonate or potassium carbonate, or an organic amine such as propylamine, butylamine, diethylamine, diisopropylamine, triethylamine, tributylamine, pyrrolidine or piperidine. The amount of the base is optionally selected within a range of from 1.0 to 20.0 equivalents, preferably from 1.0 to 3.0 equivalents, based on the compound [II].

As the palladium complex to be used in this process, it is possible to employ, for example, tetrakistriphenylphosphinepalladium, dichlorobis(triphenylphosphine)palladium, or palladium acetate-triphenylphosphine, and its amount is optionally selected within a range of from 0.001 to 0.1 equivalent based on the compound [II]. When a palladium complex is used, a tertiary phosphine such as triphenylphosphine or tri-(o-tolyl)phosphine may be co-present, and its amount may be optionally selected within a range of from 0.001 to 0.2 equivalent based on the compound [II].

In this process, a catalyst may be used. As the catalyst to be used, it is possible to employ, for example, a halogenated copper such as copper(I) iodide or an ammonium salt such as tetrabutylammonium bromide or tetrabutylammonium hydrogensulfate. Its amount may optionally be selected within a range of from 0.001 to 0.1 equivalent based on the compound [II].

The reaction temperature is from −70° C. to the boiling point of the inert solvent to be used, preferably from 0° C. to the boiling point of the inert solvent to be used. The reaction time is not constant depending upon the reaction temperature, the reaction quantity, etc., but it is usually selected within a range of from 1 to 72 hours. After completion of the reaction, the desired product is isolated from the reaction system by a conventional method and may be purified by e.g. column chromatography or recrystallization, as the case requires.

Process 2

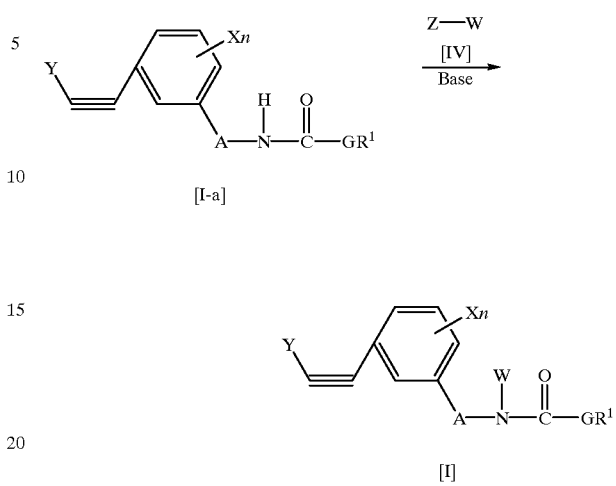

(wherein A, G, $R^1$, X, Y and n have the same meanings as mentioned above, respectively, W is a $C_1$–$C_6$ alkyl group, a $C_2$–$C_6$ alkenyl group, a $C_2$–$C_6$ alkynyl group, a $C_1$–$C_6$ alkoxy group, a $C_1$–$C_6$ alkoxy $C_1$–$C_6$ alkyl group, a $C_2$–$C_7$ alkylcarbonyl group or a $C_2$–$C_7$ alkoxycarbonyl group, and Z is a halogen atom, a tosyloxy group or a mesyloxy group.)

The compound [I] of the present invention can be produced by reacting the compound [I-a] of the present invention and the compound [IV] in an inert solvent in the presence of a base.

With respect to the amounts of starting compounds to be used in this process, relative to the compound [I-a] of the present invention, the compound [IV] is optionally selected within a range of from 1 equivalent to excess equivalents, preferably from 1.0 to 3.0 equivalents.

As the inert solvent to be used in this process, it is possible to employ the solvents exemplified in Process 1.

As the base to be used in this process, an inorganic base or an organic base may be used. As the inorganic base, it is possible to employ, for example, a carbonate of an alkali metal atom such as sodium carbonate or potassium carbonate, a carbonate of an alkali metal atom such as sodium hydrogencarbonate, a carbonate of an alkaline earth metal atom such as calcium carbonate, a hydroxide of an alkali metal atom such as sodium hydroxide or potassium hydroxide, a hydroxide of an alkaline earth metal atom such as calcium hydroxide, a hydride of an alkali metal atom such as lithium hydride or sodium hydride. As the organic base, it is possible to use, for example, an amine such as triethylamine or diisopropylethylamine, or a pyridine such as pyridine or dimethylaminopyridine. These bases may be used alone or as mixed, and the amount of the base is optionally selected within a range of from 0.5 to 3.0 equivalents, preferably from 0.8 to 2.0 equivalents, based on the compound [I-a].

The reaction temperature is from −70° C. to the boiling point of the inert solvent to be used, preferably from −20° C. to the boiling point of the inert solvent to be used. The reaction time is not constant depending upon the reaction temperature, the reaction quantity, etc., but may usually be selected within a range of from a few minutes to 48 hours. After completion of the reaction, the desired product is isolated from the reaction system by a conventional method, and may be purified by column chromatography or recrystallization as the case requires.

Process 3

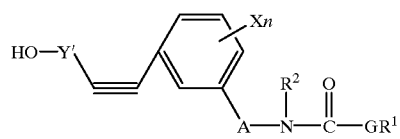

[I-b]

Halogenation

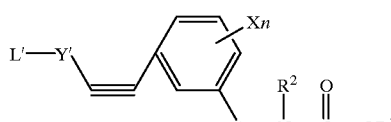

[I-c]

(wherein A, G, L', R¹, R², X and n have the same meanings as described above, respectively, and Y' is a $C_1$–$C_{10}$ alkyl group, or a $C_3$–$C_6$ cycloalkyl group.)

This process is a process for producing a compound [I-c] of the present invention wherein Y in the general formula [I] is a haloalkyl group or a halocycloalkyl group, from a compound [I-b] of the present invention wherein Y in the general formula [I] is an alkyl group substituted by a hydroxyl group or a cycloalkyl group substituted by a hydroxyl group.

The compound [I-c] of the present invention can be produced by halogenating the compound [I-b] of the present invention by a known method (e.g. The Journal of Organic Chemistry, vol 54, p5856 (1989), etc.). As the halogenating reagent, hydrogen chloride, thionyl chloride or phosphorus tribromide may, for example, be used.

As the solvent which can be used in this process, any solvent may be employed so long as it does not hinder the progress of this process. For example, an ether such as diethyl ether, diisopropyl ether, tetrahydrofuran, dioxane, 1,2-dimethoxyethane or diethylene glycol dimethyl ether, a halogenated hydrocarbon such as dichloromethane, chloroform, carbon tetrachloride or tetrachloroethane, or an aromatic hydrocarbon such as benzene, chlorobenzene or toluene, may be employed. These inert solvents may be used alone or as mixed.

The reaction temperature is from −70° C. to the boiling point of the inert solvent to be used, preferably from −20° C. to the boiling point of the inert solvent to be used.

After completion of the reaction, the desired product is isolated from the reaction system by a conventional method and may be purified by e.g. column chromatography or recrystallization, as the case requires.

Process 4

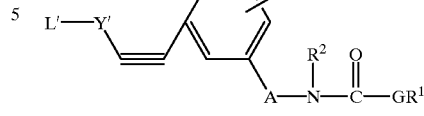

[I-c]

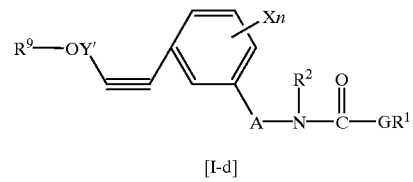

[I-d]

(wherein A, G, R¹, R², X, Y', L' and n have the same meanings as mentioned above, respectively, $R^9$ is a $C_1$–$C_6$ alkyl group, and M is an alkali metal such as potassium or sodium.)

This process is a process for producing a compound [I-d] wherein Y in the general formula [I] is an alkoxy-alkyl group or an alkoxycycloalkyl group, from a compound [I-c] of the present invention wherein Y in the general formula [I] is a haloalkyl group or a halocycloalkyl group.

The compound [I-d] of the present invention can be produced by reacting the compound [I-c] of the present invention with an alkali metal alcoholate [XIV].

As the solvent which can be used in this process, any solvent may be employed so long as it does not hinder the progress of this process. For example, a ketone such as acetone, methyl ethyl ketone or cyclohexanone, an ether such as diethyl ether, diisopropyl ether, tetrahydrofuran, dioxane, monoglime or diglime, an ester such as ethyl acetate or methyl acetate, a halogenated hydrocarbon such as dichloromethane, chloroform or carbon tetrachloride, an aromatic hydrocarbon such as benzene, chlorobenzene, nitrobenzene or toluene, a nitrile such as acetonitrile, an alcohol such as methanol, ethanol or butanol, N,N-dimethylformamide, N,N-dimethylacetamide, 1,3-dimethyl-2-imidazolinone, or dimethylsulfoxide, may be used. These inert solvents may be used alone or as mixed.

The reaction temperature is from −70° C. to the boiling point of the inert solvent to be used, preferably from −10° C. to the boiling point of the inert solvent to be used. The reaction time is not constant depending upon the reaction temperature, the reaction quantity, etc., but it is usually selected within a range of from a few minutes to 48 hours. After completion of the reaction, the desired product is isolated from the reaction system by a conventional method and may be purified by e.g. column chromatography or recrystallization, as the case requires.

The compound [II] as an intermediate for the compound [I] of the present invention, may be produced, for example, by the following known method, but not limited thereto.

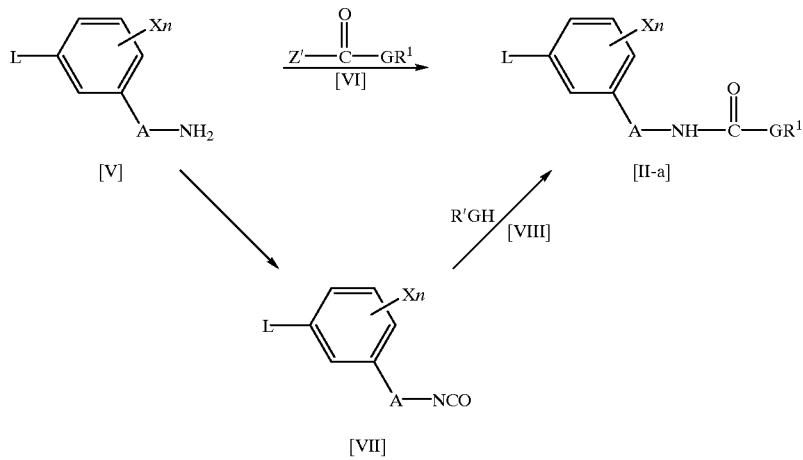

(wherein A, L, X, $R^1$, G and n have the same meanings as mentioned above, respectively, and Z' is a halogen atom.)

The compound [II-a] can be produced by reacting the compound [V] and the compound [VI] in an inert solvent in the presence of a base.

Further, the compound [II-a] can be produced by reacting in an inert solvent the compound [VIII] with the compound [VII] which can be produced from the compound [V] by a known method (e.g. SHINJIKKENKAGAKUKOZA, vol 14, p1490, Maruzen).

(wherein L, X, $R^1$, $R^2$, G, Z' and n have the same meanings as mentioned above, respectively, R' is a hydrogen atom or a $C_1$–$C_5$ alkyl group, and R" is a hydrogen atom or a $C_1$–$C_6$ alkyl group.)

The compound [II-b] can be produced by reacting in an inert solvent a compound [X] obtained by halogenating the compound [IX] or by halogenating the compound [XII] obtained by reducing the compound [XI], with potassium cyanate or sodium cyanate and a compound [VIII].

Further, the compound [II-c] can be produced by reacting the compound [X] with a compound [XIII] in an inert solvent in the presence of a base.

BEST MODE FOR CARRYING OUT THE INVENTION

Now, the processes for producing the compound of the present invention, formulation methods and applications will be specifically described with reference to Examples.

PREPARATION EXAMPLE 1

Preparation of methyl N-[2-fluoro-5-(3-hydroxy-1-butynyl)benzyl]carbamate (Compound No. 1-64)

A mixture comprising 1.60 g of methyl N-(5-bromo-2-fluorobenzyl)carbamate, 1.40 g of 1-butyn-3-ol, 0.20 g of palladium dichlorobis(triphenylphosphine), 0.10 g of copper (I) iodide and 10 ml of triethylamine, was stirred at 100° C. for 48 hours in an autoclave. The reaction solution was poured into a saturated sodium chloride aqueous solution and extracted with ethyl acetate, followed by washing with water and drying over anhydrous magnesium sulfate. The solvent was distilled off under reduced pressure, and the residue was purified by silica gel column chromatography to obtain 0.63 g of methyl N-[2-fluoro-5-(3-hydroxy-1-butynyl)benzyl]carbamate as a brown viscous liquid.

$^1$H-NMR: ($CDCl_3$/TMS, δ(ppm))1.54(d,3H), 3.70(s,3h), 4.38(d,2H), 4.72–4.75(m,1H), 5.11(br,1H), 6.98(dd,1H), 7.30–7.44(m,2H)

PREPARATION EXAMPLE 2

Preparation of methyl N-[2-fluoro-5-(trimethylsilylethynyl)benzyl]carbamate (Compound No. 1-105)

A mixture comprising 8.00 g of methyl N-(5-bromo-2-fluorobenzyl)carbamate, 4.50 g of trimethylsilylacetylene, 0.96 g of dichlorobis(triphenylphosphine)palladium, 0.47 g of copper(I) iodide and 30 ml of triethylamine, was stirred at 90° C. for 48 hours in an autoclave. This reaction solution was poured into a saturated sodium chloride aqueous solution and extracted with ethyl acetate, followed by drying over anhydrous magnesium sulfate. The solvent was distilled off under reduced pressure, and the residue was purified by silica gel column chromatography to obtain 7.09 g of methyl N-[2-fluoro-5-(trimethylsilylethynyl)benzyl]carbamate as a brown viscous liquid.

$^1$H-NMR: (CDCl$_3$/TMS, δ(ppm))0.24(s,9H), 3.70(s,3H), 4.38(d,2H), 5.08(br,1H), 6.97(dd,1H), 7.34–7.48(m,2H)

PREPARATION EXAMPLE 3

Preparation of methyl N-[5-(3,3-dimethyl-1-butynyl)-2-fluorobenzyl]carbamate (Compound No. 1-43)

A mixture comprising 1.00 g of methyl N-(5-bromo-2-fluorobenzyl)carbamate, 0.75 g of 3,3-dimethyl-1-butyne, 0.06 g of dichlorobis(triphenylphosphine)palladium, 0.02 g of copper(I) iodide, 1.29 g of triethylamine and 2.7 ml of N,N-dimethylformamide, was stirred at room temperature for 48 hours in a nitrogen atmosphere. This reaction solution was poured into a saturated sodium chloride aqueous solution and extracted with ethyl acetate, followed by drying over anhydrous magnesium sulfate. The solvent was distilled off under reduced pressure, and the residue was purified by silica gel column chromatography to obtain 0.40 g of methyl N-[5-(3,3-dimethyl-1-butynyl)-2-fluorobenzyl]carbamate as brown crystals.

$^1$H-NMR: (CDCl$_3$/TMS, δ(ppm))1.30(s,9H), 3.70(s,3H), 4.37(d,2H), 5.08(br,1H), 6.94(dd,1H), 7.24–7.39(m,2H)

PREPARATION EXAMPLE 4

Preparation of methyl N-[5-(3-chloro-1-butynyl)-2-fluorobenzyl]carbamate (Compound No. 1-77)

0.53 g of methyl N-[2-fluoro-5-(3-hydroxy-1-butynyl)benzyl]carbamate was dissolved in 10 ml of toluene. This solution was added at 0° C. to a mixture comprising 0.11 g of calcium chloride, 0.08 g of copper(I) iodide, 0.01 g of copper and 10 ml of concentrated hydrochloric acid, followed by stirring at 0° C. for 5 hours. The reaction solution was poured into a saturated sodium chloride aqueous solution and extracted with ethyl acetate, followed by drying over anhydrous magnesium sulfate. The solvent was distilled off under reduced pressure, and the residue was purified by silica gel column chromatography to obtain 0.25 g of methyl N-[5-(3-chloro-1-butynyl)-2-fluorobenzyl]carbamate as white crystals.

$^1$H-NMR: (CDCl$_3$/TMS, δ(ppm))1.83(d,3H), 3.70(s,3H), 4.38(d,2H), 4.86(q,1H), 5.13(br,1H), 6.88(dd,1H), 7.35–7.47(m,2H)

PREPARATION EXAMPLE 5

Preparation of methyl N-[2-chloro-5-(3,3-dimethyl-1-butynyl)benzyl]carbamate (Compound No. 1-121)

In a nitrogen atmosphere, 1.00 g of methyl N-(5-bromo-2-chlorobenzyl)carbamate, 0.20 g of tetrakis(triphenylphosphine)palladium, 0.07 g of copper(I) iodide and 10 ml of piperidine were added to 40 ml of toluene. To this mixed solution, 0.60 g of 3,3-dimethyl-1-butyne was added at 90° C., followed by stirring at 90° C. for 1 hour. The reaction solution was poured into a saturated sodium chloride aqueous solution and extracted with ethyl acetate, followed by drying over anhydrous magnesium sulfate. The solvent was distilled off under reduced pressure, and the residue was purified by silica gel column chromatography to obtain 0.80 g of methyl N-[2-chloro-5-(3,3-dimethyl-1-butynyl)benzyl]carbamate as colorless crystals.

$^1$H-NMR: (CDCl$_3$/TMS, δ(ppm))1.30(s,9H), 3.70(s,3H), 4.41(d,2H), 5.10(br,1H), 7.23–7.41(m,3H)

PREPARATION EXAMPLE 6

Preparation of methyl N-[5-(3,3-dimethyl-1-butynyl)-2-fluorobenzyl]-N-methoxymethylcarbamate (Compound No. 1-694)

0.20 g of methyl N-[5-(3,3-dimethyl-1-butynyl)-2-fluorobenzyl]carbamate was dissolved in N,N-dimethylformamide (5 ml). To this solution, 0.10 g of sodium hydride (60 wt %) was added at room temperature, followed by stirring for 30 minutes. Then, 0.14 g of bromomethyl methyl ether was added at room temperature, followed by stirring for 3 hours. The reaction solution was poured into water and extracted with ethyl acetate, followed by drying over anhydrous magnesium sulfate. The solvent was distilled off under reduced pressure, and the residue was purified by silica gel column chromatography to obtain 0.13 g of methyl N-[5-(3,3-dimethyl-1-butynyl)-2-fluorobenzyl]-N-methoxymethylcarbamate as a colorless viscous liquid.

$^1$H-NMR: (CDCl$_3$/TMS, δ(ppm))1.31(s,9H), 3.32(d,3H), 3.77(s,3H), 4.56(d,2H), 4.73(d,2H), 6.94(dd,1H), 7.24–7.36(m,2H)

PREPARATION EXAMPLE 7

Preparation of methyl N-[2-chloro-5-(3-hydroxy-3-methyl-1-butynyl)benzyl]carbamate (Compound No. 1-147)

A mixture comprising 3.50 g of methyl N-(5-bromo-2-chlorobenzyl)carbamate, 2.11 g of 2-methyl-3-butyn-2-ol, 0.79 g of dichlorobis(triphenylphosphine)palladium, 0.38 g of copper(I) iodide and 40 ml of triethylamine, was stirred at 90° C. for 30 hours in an autoclave. This reaction solution was poured into a saturated sodium chloride aqueous solution and extracted with ethyl acetate, followed by drying over anhydrous magnesium sulfate. The solvent was distilled off under reduced pressure, and the residue was purified by silica gel column chromatography to obtain 3.03 g of methyl N-[2-chloro-5-(3-hydroxy-3-methyl-1-butynyl)benzyl]carbamate as a brown viscous liquid.

$^1$H-NMR: (CDCl$_3$/TMS, δ(ppm))1.61(s,6H), 2.08(s,1H), 3.70(s,3H), 4.42(d,2H), 5.18(br,1H), 7.26–7.49(m,3H)

PREPARATION EXAMPLE 8

Preparation of methyl N-[2-chloro-5-(3-chloro-3-methyl-1-butynyl)benzyl]carbamate (Compound No. 1-160)

0.50 g of methyl N-[2-chloro-5-(3-hydroxy-3-methyl-1-butynyl)benzyl]carbamate was dissolved in 10 ml of toluene. This solution was added at 0° C. to a mixture comprising 0.15 g of calcium chloride, 0.11 g of copper(I) iodide, 0.01 g of copper and 10 ml of concentrated hydrochloric acid, followed by stirring at 0° C. for 5 hours. This reaction solution was poured into water and extracted with ethyl acetate, followed by drying over anhydrous magnesium sulfate. The solvent was distilled off under reduced pressure, and the residue was purified by silica gel column chromatography to obtain 0.54 g of methyl N-[2-chloro-5-(3-chloro-3-methyl-1-butynyl)benzyl]carbamate as a brown viscous liquid.

$^1$H-NMR: (CDCl$_3$/TMS, δ(ppm))1.94(s,6H), 3.71(s,3H), 4.42(d,2H), 5.18(br,1H), 7.26–7.48(m,3H)

PREPARATION EXAMPLE 9

Preparation of methyl N-[2-chloro-5-(3-methoxy-3-methyl-1-butynyl)benzyl]carbamate (Compound No. 1-174)

0.60 g of methyl N-[2-chloro-5-(3-hydroxy-3-methyl-1-butynyl)benzyl]carbamate was dissolved in 10 ml of toluene. This solution was added at 0° C. to a mixture comprising 0.12 g of calcium chloride, 0.08 g of copper(I) iodide, 0.01 g of copper and 10 ml of concentrated hydrochloric acid, followed by stirring at 0° C. for 5 hours. This solution was poured into water and extracted with ethyl acetate, followed by drying over anhydrous magnesium sulfate. The solvent was distilled off under reduced pressure, and the obtained crude product was dissolved in 10 ml, of methanol. To this solution, 0.50 g of sodium methylate (28 wt % methanol solution) was added at room temperature, followed by stirring at room temperature for 24 hours. The reaction mixture was poured into water and extracted with ethyl acetate, followed by drying over anhydrous magnesium sulfate. The solvent was distilled off under reduced pressure, and the residue was purified with silica gel column chromatography to obtain 0.52 g of methyl N-[2-chloro-5-(3-methoxy-3-methyl-1-butynyl)benzyl]carbamate as a brown viscous liquid.

$^1$H-NMR: (CDCl$_3$/TMS, δ(ppm))1.54(s, 6H), 3.42(s,3H), 3.71(s,3H), 4.43(d,2H), 5.17(br,1H), 7.26–7.46(m,3H)

Now, 1H-NMR(CDCl$_3$/TMS, δ(ppm)) data of some among examples of the compound of the present invention, will be shown in Tables 53 to 56.

TABLE 53

| Compound No. | $^1$H-NMR δ (ppm), solvent: CDCl$_3$/TMS |
|---|---|
| 1-7 | 1.31 (s, 9H); 3.70 (s, 3H); 4.33 (d, 2H); 4.98 (br, 1H); 7.16–7.31 (m, 4H) |
| 1-31 | 0.25 (s, 9H); 3.71 (s, 3H); 4.34 (d, 2H); 4.99 (br, 1H); 7.24–7.39 (m, 4H) |
| 1-60 | 1.86–1.99 (m, 6H); 3.70 (s, 3H); 4.39 (d, 2H); 5.07 (br, 1H); 5.79 (q, 1H); 6.99 (dd, 1H); 7.28–7.45 (m, 2H) |
| 1-68 | 0.96 (d, 3H); 0.98 (d, 3H); 1.56–1.95 (m, 4H); 3.70 (s, 3H); 4.41 (d, 2H); 4.59–4.66 (m, 1H); 5.18 (br, 1H); 7.17–7.45 (m, 3H) |
| 1-71 | 1.10 (t, 3H); 1.56 (s, 3H); 1.79 (q, 2H); 3.70 (s, 3H); 4.38 (d, 2H); 5.08 (br, 2H); 6.89 (d, 1H); 7.27–7.43 (m, 2H) |
| 1-116 | 1.04 (t, 3H); 1.56–1.68 (m, 2H); 2.37 (t, 2H); 3.70 (s, 3H); 4.41 (d, 2H); 5.14 (br, 1H); 7.22–7.42 (m, 3H) |
| 1-118 | 0.95 (t, 3H); 1.42–1.63 (m, 4H); 2.39 (t, 2H); 3.69 (s, 3H); 4.41 (d, 2H); 5.18 (br, 1H); 7.21–7.52 (m, 3H) |
| 1-119 | 1.12 (d, 6H); 1.86–1.94 (m, 1H); 2.28 (d, 2H); 3.70 (s, 3H); 4.41 (d, 2H); 5.14 (br, 1H); 7.22–7.42 (m, 3H) |
| 1-122 | 0.92 (t, 3H); 1.26–1.45 (m, 6H); 2.38 (t, 2H); 3.70 (s, 3H); 4.41 (d, 2H); 5.12 (br, 1H); 7.24–7.52 (m, 3H) |
| 1-134 | 1.26–1.38 (m, 2H); 1.53–1.69 (m, 4H); 1.78–1.88 (m, 2H); 2.12–2.40 (m, 1H); 2.39 (d, 2H); 3.70 (s, 3H); 4.41 (d, 2H); 5.15 (br, 1H); 7.24–7.41 (m, 3H) |
| 1-142 | 1.55 (d, 3H); 1.65 (br, 1H); 3.70 (s, 3H); 4.41 (d, 2H); 4.71–4.77 (m, 1H); 5.18 (br, 1H); 7.17–7.44 (m, 3H) |
| 1-146 | 1.00–1.58 (m, 6H); 1.53 (s, 3H); 1.60 (s, 1H); 1.85–1.94 (m, 1H); 3.70 (s, 3H); 4.41 (d, 2H); 5.32 (br, 1H); 7.25–7.44 (m, 3H) |
| 1-153 | 1.04–1.15 (m, 6H); 1.73–1.80 (m, 5H); 3.70 (s, 3H); 4.41 (d, 2H); 5.20 (br, 1H); 7.21–7.44 (m, 3H) |

TABLE 53-continued

| Compound No. | $^1$H-NMR δ (ppm), solvent: CDCl$_3$/TMS |
|---|---|
| 1-162 | 0.98 (d, H6); 1.89–2.17 (m, 3H); 3.70 (s, 3H); 4.41 (d, 2H); 4.76 (t, 1H); 5.21 (br, 1H); 7.27–7.47 (m, 3H) |
| 1-168 | 3.45 (s, 3H); 3.70 (s, 3H); 4.30 (s, 2H); 4.43 (d, 2H); 5.21 (br, 1H); 7.27–7.48 (m, 3H) |
| 1-178 | 0.99 (t, 6H); 1.71–1.83 (m, 4H); 3.37 (s, 3H); 3.70 (s, 3H); 4.42 (d, 2H); 5.28 (br, 1H); 7.28–7.45 (m, 3H) |
| 1-181 | 1.74–2.03 (m, 8H); 2.30 (br, 1H); 3.69 (s, 3H); 4.40 (d, 2H); 5.32 (br, 1H); 7.22–7.44 (m, 3H) |

TABLE 54

| Compound No. | $^1$H-NMR δ (ppm), solvent: CDCl$_3$/TMS |
|---|---|
| 1-184 | 0.25 (s, 9H); 3.70 (s, 3H); 4.41 (d, 2H); 5.15 (br, 1H); 7.26–7.49 (m, 3H) |
| 1-266 | 2.32 (s, 3H); 3.04 (s, 1H); 3.70 (s, 3H); 4.33 (d, 2H); 4.96 (br, 1H); 7.10–7.51 (m, 3H) |
| 1-274 | 1.31 (s, 9H); 2.30 (s, 3H); 3.71 (s, 3H); 4.32 (d, 2H); 4.82 (br, 1H); 7.06–7.26 (m, 3H) |
| 1-333 | 0.24 (s, 9H); 2.31 (s, 3H); 3.71 (s, 3H); 4.33 (d, 2H); 4.85 (br, 1H); 7.08–7.36 (m, 3H) |
| 1-349 | 1.30 (s, 9H); 3.67 (s, 3H); 3.83 (s, 3H); 4.30 (d, 2H); 5.15 (br, 1H); 7.26–7.30 (m, 3H) |
| 1-404 | 0.23 (s, 9H); 3.67 (s, 3H); 3.84 (s, 3H); 4.30 (d, 2H); 5.14 (br, 1H); 6.77 (d, 1H); 7.36–7.39 (m, 2H) |
| 1-539 | 1.31 (s, 9H); 2.29 (s, 3H); 3.70 (s, 3H); 4.28 (d, 2H); 4.95 (br, 1H); 6.98–7.12 (m, 3H) |
| 1-575 | 1.33 (s, 9H); 3.70 (s, 3H); 4.29 (d, 2H); 5.01 (br, 1H); 6.99 (t, 1H); 7.08–7.20 (m, 1H); 7.25–7.34 (m, 1H) |
| 1-693 | 1.31 (s, 9H); 2.86–2.92 (m, 3H); 3.75 (s, 3H); 4.49 (d, 2H); 6.94 (dd, 1H); 7.25–7.35 (m, 2H) |
| 1-696 | 1.31 (s, 9H); 2.23 (s, 1H); 3.78 (s, 3H); 4.01 (br, 2H); 4.11 (br, 1H); 6.95 (dd, 1H); 7.26–7.35 (m, 2H) |
| 1-698 | 1.30 (s, 9H); 3.83 (s, 6H); 4.93 (s, 2H); 6.93 (dd, 1H); 7.21–7.35 (m, 2H) |
| 1-1117 | 1.25 (t, 3H); 1.98 (s, 3H); 4.15 (q, 2H); 4.42 (d, 2H); 5.17 (br, 1H); 5.32 (s, 1H); 5.40 (s, 1H); 7.20–7.47 (m, 3H) |
| 1-1273 | 1.33 (s, 9H); 3.66 (s, 3H); 4.54 (d, 2H); 5.16 (br, 1H); 6.94 (t, 1H); 7.36 (dd, 1H) |
| 1-1318 | 1.30 (s, 9H); 3.70 (s, 3H); 4.42 (d, 2H); 5.19 (br, 1H); 7.31–7.42 (m, 2H) |
| 1-1325 | 0.95 (t, 3H); 1.40–1.62 (m, 4H); 2.34 (s, 3H); 2.39 (t, 2H); 3.69 (s, 3H); 4.41 (d, 2H); 5.13 (br, 1H); 7.21 (s, 1H); 7.26 (s, 1H) |
| 1-1327 | 1.30 (s, 9H); 2.33 (s, 3H); 3.69 (s, 3H); 4.41 (d, 2H); 5.17 (br, 1H); 7.21–7.26 (m, 2H) |
| 1-1330 | 1.24–1.88 (m, 8H); 2.05–2.12 (m, 1H); 2.16 (s, 3H); 2.34 (d, 2H); 3.69 (s, 3H); 4.41 (d, 2H); 5.13 (br, 1H); 7.21 (s, 1H); 7.26 (s, 1H) |

TABLE 55

| Compound No. | $^1$H-NMR δ (ppm), solvent: CDCl$_3$/TMS |
|---|---|
| 1-1331 | 1.53 (s, 6H); 2.35 (s, 3H); 3.41 (s, 3H); 3.70 (s, 3H); 4.42 (d, 2H); 5.20 (br, 1H); 7.26–7.31 (m, 2H) |
| 1-1332 | 0.24 (s, 9H); 2.35 (s, 3H); 3.70 (s, 3H); 4.42 (d, 2H); 5.14 (br, 1H); 7.26–7.34 (m, 2H) |
| 1-1345 | 1.30 (s, 9H); 2.13 (s, 3H); 2.19 (s, 3H); 3.70 (s, 3H); 4.34 (d, 2H); 4.75 (br, 1H); 7.01–7.26 (m, 2H) |
| 1-1363 | 1.30 (s, 9H); 3.69 (s, 3H); 3.87 (s, 3H); 4.35 (d, 2H); 5.10 (br, 1H); 7.24–7.34 (m, 2H) |
| 1-1372 | 1.30 (s, 9H); 2.24 (s, 3H); 3.68 (s, 3H); 3.73 (s, 3H); 4.34 (d, 2H); 5.11 (br, 1H); 7.16–7.27 (m, 2H) |
| 1-1391 | 1.33 (s, 9H); 3.70 (s, 3H); 4.37 (d, 2H); 5.14 (br, 1H); 7.40 (s, 1H); 7.44 (s, 1H) |
| 1-1396 | 0.27 (s, 9H); 3.70 (s, 3H); 4.37 (d, 2H); 5.20 (br, 1H); 7.41 (s, 1H); 7.51 (s, 1H) |
| 1-1400 | 1.33 (s, 9H); 3.69 (s, 3H); 3.84 (s, 3H); 4.35 (d, 2H); 5.07 (br, 1H); 6.84 (s, 1H); 7.37 (s, 1H) |
| 1-1409 | 1.32 (s, 9H); 2.27 (s, 3H); 2.34 (s, 3H); 3.69 (s, 3H); |

TABLE 55-continued

| Compound No. | $^1$H-NMR δ (ppm), solvent: CDCl$_3$/TMS |
|---|---|
| | 4.29 (d, 2H); 4.75 (br, 1H); 6.98 (s, 1H); 7.26 (s, 1H) |
| 1-1415 | 3.70 (s, 3H); 4.42 (d, 2H); 5.16 (d, 2H); 5.28 (br; 1H); 7.27–7.49 (m, 3H) |
| 1-1416 | 4.44 (d, 2H); 5.19 (br, 1H); 6.40 (t, 1H); 7.31–7.56 (m, 3H) |
| 1-1417 | 1.11 (t, 6H); 1.79–1.97 (m, 4H); 3.71 (s, 3H); 4.43 (d, 2H); 5.71 (br, 1H); 7.26–7.47 (m, 3H) |
| 1-1419 | 1.00 (d, 3H); 1.01 (d, 3H); 1.63–1.81 (m, 1H); 1.86–2.05 (m, 2H); 3.70 (s, 3H); 4.42 (d, 2H); 5.19 (br, 1H); 5.25–5.45 (m, 1H); 7.28–7.48 (m, 3H) |
| 1-1420 | 0.93 (d, 6H); 1.50 (q, 2H); 1.67–1.78 (m, 1H); 2.39 (t, 2H); 3.70 (s, 3H); 4.41 (d, 2H); 5.14 (br, 1H); 7.21–7.41 (m, 3H) |
| 1-1421 | 1.01 (d, 6H); 1.21 (d, 3H); 1.66–1.75 (m, 1H); 2.48–2.57 (m, 1H); 3.70 (s, 3H); 4.41 (d, 2H); 5.17 (br, 1H); 7.22–7.41 (m, 3H) |
| 1-1422 | 1.04 (t, 6H); 1.47–1.63 (m, 4H); 2.35–2.42 (m, 1H); 3.70 (s, 3H); 4.41 (d, 2H); 5.15 (br, 1H); 7.23–7.46 (m, 3H) |
| 1-1423 | 1.26 (t, 3H); 1.52 (d, 3H); 3.45–3.55 (m, 1H); 3.71 (s, 3H); 3.78–3.88 (m, 1H); 4.36 (q, 1H); 4.42 (d, 2H); 5.18 (br, 1H); 7.27–7.46 (m, 3H) |

TABLE 56

| Compound No. | $^1$H-NMR δ (ppm), solvent: CDCl$_3$/TMS |
|---|---|
| 1-1424 | 1.18 (d, 3H); 1.25 (d, 3H); 1.49 (d, 3H); 3.70 (s, 3H); 3.92–4.00 (m, 1H); 4.45 (q, 1H); 4.42 (d, 2H); 5.21 (br, 1H); 7.20–7.45 (m, 3H) |
| 1-1425 | 1.00 (d, 3H); 1.07 (d, 3H); 1.40 (s, 3H); 1.95–2.34 (m, 1H); 3.40 (s, 3H); 3.70 (s, 3H); 4.42 (d, 2H); 5.19 (br, 1H); 7.27–7.45 (m, 3H) |
| 1-1426 | 0.96 (d, 3H); 0.97 (d, 3H); 1.58–1.80 (m, 2H); 1.84–1.95 (m, 1H); 2.93 (d, 2H); 3.46 (s, 3H); 3.75 (d, 3H); 4.19 (t, 1H); 4.56 (d, 2H); 7.22–7.33 (m, 3H) |
| 1-1428 | 0.16 (s, 9H); 1.57 (s, 2H); 3.70 (s, 3H); 4.41 (d, 2H); 5.11 (br, 1H); 7.19–7.37 (m, 3H) |
| 1-1429 | 1.54 (s, 9H); 3.72 (s, 3H); 4.44 (d, 2H); 5.16 (br, 1H); 7.26–7.60 (m, 3H) |
| 1-1430 | 1.26 (t; 3H); 1.30 (s; 9H); 4.15 (q; 2H); 4.40 (d; 2H); 5.11 (br; 1H); 7.20–7.41 (m, 3H) |
| 1-1431 | 1.24 (d, 6H); 1.30 (s, 9H); 4.40 (d, 2H); 4.91–4.98 (m, 1H); 5.06 (br, 1H); 7.20–7.40 (m, 3H) |
| 2-30 | 1.30 (s, 9H); 1.46 (d, 3H); 3.66 (s, 3H); 4.98 (q, 1H); 5.08 (br, 1H); 6.93 (dd, 1H); 7.23–7.32 (m, 2H) |
| 2-163 | 0.88 (d, 3H); 0.99 (d, 3H); 1.31 (s, 9H); 2.05–2.14 (m, 1H); 3.65 (s, 3H); 4.79 (t, 1H); 5.22 (br, 1H); 7.17–7.26 (m, 3H) |

Now, preparation examples of intermediates for the preparation of the compounds of the present invention will be shown as Reference Examples.

Reference Example 1

Preparation of methyl N-(3-bromobenzyl)carbamate (Compound II-a)

To a suspension of 10.0 g of 3-bromobenzylamine hydrochloride in chloroform (100 ml), 9.55 g of triethylamine was added at room temperature. To this solution, 4.67 g of methyl chloroformate was dropwise added under cooling with ice, followed by stirring at room temperature for 2 hours. The reaction solution was poured into a sodium chloride aqueous solution, and the organic layer was dried over anhydrous magnesium sulfate. The solvent was distilled off under reduced pressure, and the residue was purified by silica gel column chromatography to obtain 9.54 g of methyl N-(3-bromobenzyl)carbamate as white crystals.

$^1$H-NMR: (CDCl$_3$/TMS, δ(ppm))3.69(s,3H), 4.33(d,2H), 5.17(br,1H), 7.16–7.42(m,4H)

Reference Example 2

Preparation of 5-bromo-2-chlorobenzyl alcohol (Compound XII)

25.0 g of methyl 5-bromo-2-chlorobenzoate was dissolved in 130 ml of dichloromethane. To this solution, 230 ml of a 0.96 M DIBAL (diisobutylalminium hydride) hexane solution was added at −40° C. in a nitrogen atmosphere, followed by stirring at room temperature for 4 hours. To this reaction solution, 10% hydrochloric acid was carefully added while cooling, followed by extraction with ethyl acetate and drying over anhydrous magnesium sulfate. The solvent was distilled off under reduced pressure, and the obtained crude crystals were washed with hexane to obtain 20.8 g of 5-bromo-2-chlorobenzyl alcohol as white crystals.

$^1$H-NMR: (CDCl$_3$/TMS, δ(ppm))2.18(t,1H), 4.74(d,2H), 7.19–7.65(m,3H)

Reference Example 3

Preparation of 5-bromo-2-chlorobenzyl bromide (Compound X)

20.0 g of 5-bromo-2-chlorobenzyl alcohol was dissolved in 100 ml of ethylene glycol dimethyl ether. To this solution, 9.4 g of phosphorus tribromide was added at −20° C., followed by stirring at room temperature for 1 hour. To the reaction solution, water was added, followed by extraction with toluene, and washing with an aqueous sodium hydrogencarbonate solution. The organic layer was dried over anhydrous magnesium sulfate. The solvent was distilled off under reduced pressure to obtain 24.9 g of a crude product of 5-bromo-2-chlorobenzyl bromide as white crystals.

Reference Example 4

Preparation of methyl N-(5-bromo-2-chlorobenzyl) carbamate (Compound II-b)

A mixture comprising 24.9 g of the crude product of 5-bromo-2-chlorobenzyl bromide obtained in Reference Example 3, 12.2 g of potassium cyanate, 18.0 g of methanol and 100 ml of N,N-dimethylformamide, was stirred at 100° C. for 2 hours. To this reaction mixture, water was added, followed by extraction with ethyl acetate. The organic layer was dried over anhydrous magnesium sulfate. The solvent was distilled off under reduced pressure, and the obtained crude crystals were washed with isopropanol to obtain 19.0 g of methyl N-(5-bromo-2-chlorobenzyl)carbamate as white crystals.

$^1$H-NMR: (CDCl$_3$/TMS, δ(ppm))3.71(s,3H), 4.41(d,2H), 5.23(br,1H), 7.23–7.52(m,3H)

Reference Example 5

Preparation of methyl N-(5-bromo-2-chlorobenzyl) carbamate (Compound II-b)

A mixture comprising 10.0 g of 5-bromo-2-chlorotoluene, 8.7 g of N-bromosuccinimide, 0.3 g of 2,2'-azobisisobutyronitrile and 60 ml of carbon tetrachloride, was refluxed under heating for 3 hours and, after cooling to room temperature, filtered and concentrated. A mixture comprising the obtained crude product, 5.9 g of potassium cyanate, 10 ml of methanol and 50 ml of N,N-dimethylformamide, was stirred at 100° C. for 2 hours. To this reaction mixture, water was added, followed by extraction with ethyl acetate. The organic layer was dried over anhydrous magnesium sulfate. The solvent was distilled off under reduced pressure, and the obtained crude crystals were washed with isopropanol to obtain 6.8 g of methyl N-(5-bromo-2-chlorobenzyl)carbamate as white crystals.

Reference Example 6

Preparation of methyl N-[1-(3-bromophenyl)ethyl] carbamate (Compound II-a)

To a solution of 23.8 g of 3-bromo-α-methylbenzylamine in toluene (120 ml), 14.1 g of pyridine was added at room temperature. To this solution, 18.6 g of methyl chloroformate was dropwise added under cooling with ice, followed by stirring at room temperature for 2 hours. The reaction solution was poured into a citric acid aqueous solution and extracted with ethyl acetate. The organic layer was washed with a citric acid aqueous solution and then dried over anhydrous magnesium sulfate. The solvent was distilled off under reduced pressure. The residue was purified by silica gel column chromatography to obtain 10.5 g of methyl N-[1-(3-bromophenyl)ethyl]carbamate as a colorless transparent viscous liquid.

$^1$H-NMR: (CDCl$_3$/TMS, δ(ppm))1.46(d,3H), 3.65(s,3H), 4.78(br,1H), 5.14(br,1H), 7.16–7.42(m,4H)

Reference Example 7

Preparation of methyl N-methoxy-N-(3-bromobenzyl)carbamate (Compound II-c)

To a solution of 2.52 g of methyl N-methoxy carbamate in N,N-dimethylformamide (30 ml), 1.15 g of 60% sodium hydride was added at room temperature, followed by stirring for 30 minutes. To this solution, 1.00 g of 3-bromobenzyl bromide was dropwise added at room temperature, followed by stirring for 3 hours. After completion of the reaction, the reaction solution was poured into water and extracted with ethyl acetate to obtain an organic layer, which was dried over anhydrous magnesium sulfate. Then, the solvent was distilled off under reduced pressure. The residue was purified by silica gel column chromatography to obtain 4.99 g of methyl N-methoxy-N-(3-bromobenzyl)carbamate as a transparent viscous liquid.

$^1$H-NMR: (CDCl$_3$/TMS, δ(ppm))3.62(s,3H), 3,81(s,3H), 4.61(s,2H), 7.0–7.6(m,4H)

The agricultural/horticultural fungicides of the present invention contain phenylacetylene derivatives represented by the general formula (I) as the active ingredients. When the compounds of the present invention are used for agricultural/horticultural fungicides, the active ingredient can be used in appropriate formulations depending on the purpose. The active ingredient is usually diluted with an inert liquid or solid carrier and is used in an appropriate dosage form such as a dust, a wettable powder, an emulsifiable concentrate or a granule by blending it with a surfactant and other ingredients, depending on its use.

Preferable examples of carriers include solid carriers such as talc, bentonite, clay, kaolin, diatomaceous earth, white carbon, vermiculite, slaked lime, silica sand, ammonium sulfate and urea and liquid carriers such as isopropyl alcohol, xylene, cyclohexanone and methylnaphthalene. Examples of surfactants and dispersants include dinaphthylmethanesulfonates, alcohol-sulfuric acid ester salts, alkylarylsulfonates, lignin sulfonate, polyoxyethylene glycol ether, polyoxyethylene alkyl aryl ethers and polyoxyethylene sorbitan monoalkylate. Examples of adjuvants include carboxymethyl cellulose and the like. These formulations are applied after diluted to appropriate concentrations or directly.

The agricultural/horticultural fungicides of the present invention can be used for foliage treatment, soil treatment or submerged treatment. The blending proportion of the active ingredient is suitably selected depending on the case. However, the preferable proportion is from 0.1 to 20% (by weight) in the cases of a dust or a granule, and from 5 to 80% (by weight) in the cases of an emulsifiable concentrate or a wettable powder.

The dose of the agricultural/horticultural fungicides of the present invention depends on the type of the compound, the disease to be controlled, the tendency of disease development, the degrees of the damage, the environmental conditions and the type of the formulation to be used. For example, for direct use as a dust or a granule, the dose of the active ingredient is selected suitably within the range of from 0.1 g to 5 kg, preferably from 1 g to 1 kg, per 10 are. For use in a liquid state as an emulsifiable concentrate or a wettable powder, the dose is selected suitably within the range of from 0.1 ppm to 10,000 ppm, preferably from 10 to 3,000 ppm.

The compounds of the present invention in the above-mentioned formulations can control plant diseases caused by Oomycetes, Ascomycetes, Deuteromycetes and Basidiomycetes. Specific but non-restrictive examples of microorganisms are given below. Pseudoperonospora genus such as *Pseudoperonospora cubensis*, Erysiphe genus such as *Erysiphe graminis*, Venturia genus such as *Venturia inaequalis*, Pyricularia genus such as *Pyricularia oryzae*, Botrytis genus such as *Botrytis cinerea* and Rhizoctonia genus such as *Rhizoctonia solani*.

The compounds of the present invention may be used in combination with an insecticide, another fungicide, a herbicide, a plant growth regulator or a fertilizer, as the case requires. Now, typical formulations of the agricultural/horticultural fungicides of the present invention will be described with reference to Formulation Examples. Hereinafter, "%" means "% by weight".

Formulation Example 1

Dust

2% of Compound (1-115), 5% of diatomaceous earth and 93% of clay were uniformly mixed and pulverized to give a dust.

Formulation Example 2

Wettable Powder

50% of Compound (1-105), 45% of diatomaceous earth, 2% of sodium dinaphthylmethanedisulfonate and 3% of sodium lignin sulfonate were uniformly mixed and pulverized to give a wettable powder.

Formulation Example 3

Emulsifiable Concentrate

30% of Compound (1-184), 20% of cyclohexanone, 11% of polyoxyethylene alkyl aryl ether, 4% of calcium alkylbenzenesulfonate and 35% of methylnaphthalene were uniformly dissolved to give an emulsifiable concentrate.

Formulation Example 4

Granule

5% of Compound (1-132), 2% of the sodium salt of the lauryl alcohol sulfuric ester, 5% of sodium lignin sulfonate, 2% of carboxymethyl cellulose and 86% of clay were uniformly mixed and pulverized. The resulting mixture was kneaded with 20% of water, granulated to 14 to 32 mesh by means of an extrusion granulator, dried to give a granule.

Now, the effects of the agricultural/horticultural fungicides of the present invention will be described with reference to specific Test Examples.

Test Example 1
Test for Preventive Effect on Cucumber Downy Mildew 9 cucumber seeds (variety: Sagami-hanjiro) were sown in each 9 cm×9 cm polyvinyl chloride pot and grown in a greenhouse for 7 days. The cotyledonary cucumber seedlings were treated with 10 ml per pot of aqueous solutions of wettable powders prepared in accordance with Formulation Example 2, at a concentration of 500 ppm in terms of the active ingredients, and dried in the air. Then, the seedlings were inoculated with *Pseudoperonospora cubensis* zoosporangia in suspension by spraying and immediately placed in a moist chamber at 22° C. for 24 hours. Thereafter, the seedlings were placed in a greenhouse. 7 days after the inoculation, the total diseased area in each pot was observed and evaluated on the basis of the standards shown in Table 57. The results are shown in Table 58.

TABLE 57

| Evaluation | |
|---|---|
| A | No diseased area |
| B | Diseased area of less than 25% |
| C | Diseased area of at least 25% but less than 50% |
| D | Diseased area of at least 50% |

TABLE 58

| Compound No. | Evaluation | Compound No. | Evaluation |
|---|---|---|---|
| 1-7 | A | 1-349 | A |
| 1-31 | A | 1-404 | A |
| 1-35 | B | 1-539 | A |
| 1-43 | A | 1-696 | A |
| 1-54 | A | 1-698 | A |
| 1-60 | B | 1-837 | A |
| 1-105 | A | 1-839 | A |
| 1-114 | A | 1-1212 | A |
| 1-115 | A | 1-1327 | A |
| 1-116 | A | 1-1363 | A |
| 1-117 | A | 1-1372 | A |
| 1-118 | A | 1-1387 | A |
| 1-119 | A | 1-1396 | A |
| 1-120 | A | 1-1400 | A |
| 1-121 | A | 1-1409 | A |
| 1-122 | A | 1-1415 | B |
| 1-132 | A | 1-1417 | B |
| 1-134 | A | 1-1418 | A |
| 1-141 | B | 1-1419 | A |
| 1-146 | A | 1-1420 | A |
| 1-153 | A | 1-1421 | B |
| 1-162 | A | 1-1423 | B |
| 1-169 | A | 1-1424 | B |
| 1-174 | A | 1-1425 | A |
| 1-178 | A | 1-1428 | A |
| 1-184 | A | 1-1430 | A |
| 1-187 | B | 1-1431 | B |
| 1-199 | A | 2-30 | A |
| 1-266 | A | 2-43 | A |
| 1-274 | A | 2-97 | A |
| 1-333 | A | | |

Test Example 2
Test for Preventive Effect on Apple Scab 5 apple seeds (variety: Kogyoku) were sown in each 9 cm×9 cm polyvinyl chloride pot and grown in a greenhouse for 20 days. The 4-foliage-leaf apple seedlings were treated with 20 ml per pot of aqueous solutions of wettable powders prepared in accordance with Formulation Example 2, at a concentration of 500 ppm in terms of the active ingredients, and dried in the air. Then, the seedlings were inoculated with *Venturia inaequalis* spores in suspension by spraying and immediately placed in a moist chamber at 22° C. for 48 hours. Thereafter, the seedlings were placed in a greenhouse for development of the disease. 14 days after the inoculation, the diseased areas of the upper two of the inoculated leaves were observed and evaluated on the basis of the standards shown in Table 57. The results are shown in Table 59.

TABLE 59

| Compound No. | Evaluation | Compound No. | Evaluation | Compound No. | Evaluation |
|---|---|---|---|---|---|
| 1-7 | A | 1-181 | B | 1-1422 | A |
| 1-31 | A | 1-183 | B | 1-1423 | A |
| 1-35 | A | 1-184 | B | 1-1424 | A |
| 1-36 | A | 1-186 | B | 1-1425 | A |
| 1-43 | A | 1-187 | A | 1-1426 | A |
| 1-54 | A | 1-188 | B | 1-1427 | A |
| 1-58 | A | 1-199 | A | 1-1430 | A |
| 1-64 | B | 1-266 | A | 1-1431 | A |
| 1-68 | A | 1-274 | A | 2-30 | A |
| 1-71 | A | 1-333 | A | 2-43 | A |
| 1-77 | B | 1-341 | A | 2-97 | A |
| 1-105 | A | 1-349 | A | | |
| 1-113 | B | 1-404 | A | | |
| 1-114 | A | 1-539 | A | | |
| 1-115 | A | 1-575 | B | | |
| 1-116 | A | 1-696 | A | | |
| 1-117 | A | 1-698 | B | | |
| 1-118 | B | 1-837 | A | | |
| 1-120 | A | 1-839 | A | | |
| 1-121 | A | 1-1124 | A | | |
| 1-122 | A | 1-1212 | A | | |
| 1-132 | A | 1-1273 | B | | |
| 1-134 | A | 1-1327 | A | | |
| 1-137 | B | 1-1363 | A | | |
| 1-141 | A | 1-1372 | A | | |
| 1-142 | B | 1-1387 | A | | |
| 1-146 | B | 1-1391 | A | | |
| 1-147 | B | 1-1396 | A | | |
| 1-153 | A | 1-1400 | A | | |
| 1-160 | B | 1-1409 | A | | |
| 1-162 | B | 1-1415 | A | | |
| 1-167 | B | 1-1416 | A | | |
| 1-168 | B | 1-1417 | A | | |
| 1-169 | A | 1-1418 | A | | |
| 1-174 | A | 1-1419 | A | | |
| 1-178 | A | 1-1421 | A | | |

Test Example 3
Test for Preventive Effect on Wheat Powdery Mildew 9 wheat seeds (variety: Norin-61-go) were sown in each 9 cm×9 cm polyvinyl chloride pot, grown in a greenhouse for 8 days, then treated with 10 ml per pot of aqueous solutions of wettable powders prepared in accordance with Formulation Example 2, at a concentration of 500 ppm in terms of the active ingredients and dried in the air. Then, the seedlings were inoculated with *Erysiphe graminis* spores by sprinkle over the plant and maintained in a greenhouse. 10 days after the inoculation, the total diseases area of the first leaves in each pot was observed and evaluated on the basis of the standards shown in Table 57. The results are shown in Table 60.

TABLE 60

| Compound No. | Evaluation | Compound No. | Evaluation | Compound No. | Evaluation |
|---|---|---|---|---|---|
| 1-7 | A | 1-186 | B | 1-1422 | B |
| 1-31 | A | 1-187 | B | 1-1423 | A |
| 1-35 | A | 1-199 | A | 1-1424 | A |
| 1-36 | B | 1-266 | B | 1-1425 | A |
| 1-43 | A | 1-274 | A | 1-1426 | A |
| 1-54 | A | 1-333 | A | 1-1427 | A |

TABLE 60-continued

| Compound No. | Evaluation | Compound No. | Evaluation | Compound No. | Evaluation |
|---|---|---|---|---|---|
| 1-58 | A | 1-341 | B | 1-1428 | A |
| 1-60 | B | 1-349 | A | 1-1429 | A |
| 1-68 | B | 1-404 | B | 1-1430 | A |
| 1-71 | A | 1-539 | A | 1-1431 | A |
| 1-77 | A | 1-575 | A | 2-30 | A |
| 1-105 | A | 1-693 | A | 2-43 | A |
| 1-113 | B | 1-694 | B | 2-97 | B |
| 1-114 | A | 1-696 | B | | |
| 1-115 | A | 1-698 | B | | |
| 1-116 | A | 1-837 | B | | |
| 1-117 | A | 1-839 | A | | |
| 1-118 | A | 1-1124 | B | | |
| 1-119 | A | 1-1177 | B | | |
| 1-120 | A | 1-1273 | B | | |
| 1-121 | A | 1-1327 | A | | |
| 1-122 | A | 1-1363 | A | | |
| 1-132 | A | 1-1372 | A | | |
| 1-134 | A | 1-1387 | B | | |
| 1-146 | B | 1-1391 | A | | |
| 1-147 | A | 1-1396 | A | | |
| 1-153 | B | 1-1400 | A | | |
| 1-160 | B | 1-1409 | A | | |
| 1-162 | B | 1-1415 | A | | |
| 1-167 | B | 1-1416 | B | | |
| 1-169 | A | 1-1417 | B | | |
| 1-174 | A | 1-1418 | A | | |
| 1-178 | A | 1-1419 | A | | |
| 1-181 | B | 1-1420 | A | | |
| 1-184 | A | 1-1421 | A | | |

Test Example 4
Test for Preventive Effect on Rice Blast 15 rice seeds (variety: Aichi-asahi) were sown in each unglazed pot of 7 cm in diameter and grown in a greenhouse for 2 to 3 weeks. The rice seedlings with completely developed 4th leaves were treated 10 ml per pot of aqueous solutions of wettable powders prepared in accordance with Formulation Example 2, at a concentration of 500 ppm in terms of the active ingredients and dried in the air. Then, the seedlings were inoculated with *Pyricularia oryzae* spores in suspension by spraying and immediately placed in a moist chamber at 25° C. for 24 hours. Thereafter, the seedlings were placed in a greenhouse. 5 days after the inoculation, the spotty lesions on the 4th leaves were counted, and the preventive values were calculated in accordance with numerical expression 1 and evaluated on the basis of the standards shown in Table 61. The results are shown in Table 62.

$$\text{Preventive value (\%)} = \left(1 - \frac{\text{Number of lesions in treated area}}{\text{Number of lesions in untreated area}}\right) \times 100 \quad \text{(Numerical expression 1)}$$

TABLE 61

| Evaluation | Preventive value |
|---|---|
| A | 100% |
| B | Less than 100% but at least 80.0% |
| C | Less than 80.0% but at least 50.0% |
| D | Less than 50.0% |

TABLE 62

| Compound No. | Evaluation | Compound No. | Evaluation |
|---|---|---|---|
| 1-7 | B | 1-539 | A |
| 1-31 | B | 1-696 | B |
| 1-35 | B | 1-837 | B |
| 1-43 | B | 1-839 | B |
| 1-54 | B | 1-1327 | A |
| 1-58 | B | 1-1363 | B |
| 1-68 | B | 1-1372 | B |
| 1-77 | B | 1-1391 | B |
| 1-105 | B | 1-1400 | B |
| 1-113 | B | 1-1409 | A |
| 1-114 | B | 1-1415 | A |
| 1-115 | A | 1-1416 | B |
| 1-116 | A | 1-1417 | B |
| 1-117 | B | 1-1418 | B |
| 1-118 | B | 1-1419 | A |
| 1-119 | B | 1-1420 | A |
| 1-120 | A | 1-1423 | A |
| 1-121 | A | 1-1424 | A |
| 1-122 | A | 1-1425 | B |
| 1-132 | A | 1-1426 | B |
| 1-134 | B | 1-1427 | B |
| 1-141 | A | 1-1428 | A |
| 1-146 | B | 1-1430 | A |
| 1-153 | B | | |
| 1-162 | B | | |
| 1-168 | B | | |
| 1-169 | B | | |
| 1-174 | B | | |
| 1-178 | B | | |
| 1-184 | A | | |
| 1-199 | A | | |
| 1-266 | A | | |
| 1-274 | A | | |
| 1-349 | A | | |
| 1-404 | B | | |

Test Example 5
Test for Preventive Effect on Cucumber Gray Mold 9 cucumber seeds (variety: Sagami-hanjiro) were sown in each 9 cm×9 cm polyvinyl chloride pot and grown in a greenhouse for 7 days. The cotyledonary cucumber seedlings were treated with 10 ml per pot of aqueous solutions of wettable powders prepared in accordance with Formulation Example 2, at a concentration of 500 ppm in terms of the active ingredients, and dried in the air. Then, the seedlings were inoculated with homogenized *Botrytis cinerea* hyphae in solution by spraying and immediately placed in a moist chamber at 22° C. 3 days after the inoculation, the total diseased area in each pot was observed and evaluated on the basis of the standards shown in Table 57. The results are shown in Table 63.

TABLE 63

| Compound No. | Evaluation | Compound No. | Evaluation |
|---|---|---|---|
| 1-7 | B | 1-1327 | A |
| 1-43 | A | 1-1391 | B |
| 1-58 | A | 1-1400 | B |
| 1-60 | B | 1-1409 | B |
| 1-64 | A | 1-1415 | B |
| 1-68 | A | 1-1416 | B |
| 1-77 | A | 1-1417 | B |
| 1-115 | A | 1-1418 | B |
| 1-116 | A | 1-1419 | A |
| 1-117 | B | 1-1420 | B |
| 1-118 | A | 1-1423 | B |
| 1-119 | B | 1-1425 | B |
| 1-120 | B | 1-1427 | B |
| 1-121 | A | 1-1430 | A |

TABLE 63-continued

| Compound No. | Evaluation | Compound No. | Evaluation |
|---|---|---|---|
| 1-122 | A | 1-1431 | A |
| 1-132 | A | 2-30 | B |
| 1-134 | A | 2-43 | B |
| 1-141 | A | 2-97 | A |
| 1-146 | A | | |
| 1-147 | B | | |
| 1-153 | A | | |
| 1-162 | A | | |
| 1-178 | B | | |
| 1-181 | A | | |
| 1-186 | A | | |
| 1-187 | B | | |
| 1-266 | B | | |
| 1-274 | B | | |
| 1-333 | A | | |
| 1-696 | A | | |
| 1-698 | A | | |
| 1-837 | B | | |
| 1-1212 | B | | |

Test Example 6
Test for Preventive Effect on Rice Sheath Blight 15 rice seeds (variety: Kinmaze) were sown in each unglazed pot of 7 cm in diameter and grown in a greenhouse for 4 to 5 weeks. The rice seedlings with completely developed 5th leaves were treated 10 ml per pot of aqueous solutions of wettable powders prepared in accordance with Formulation Example 2, at a concentration of 500 ppm in terms of the active ingredients and dried in the air. Then, the plant feet of the seedlings were inoculated with *Rhizoctonia solani* mycelia grown in a chaff bran medium, and the seedlings were immediately placed in a moist chamber at 28° C. 6 days after the inoculation, the heights of the lesions on the leaf sheaths were measured, and the preventive values were calculated in accordance with numerical expression 2 and evaluated on the basis of the standards shown in Table 61. The results are shown in Table 64.

$$\text{Preventive value (\%)} = \left(1 - \frac{\text{Height of lesions in treated area}}{\text{Height of lesions in untreated area}}\right) \times 100 \quad \text{(Numerical expression 2)}$$

TABLE 64

| Compound No. | Evaluation | Compound No. | Evaluation |
|---|---|---|---|
| 1-114 | B | 1-1428 | B |
| 1-115 | A | 1-1430 | B |
| 1-116 | A | | |
| 1-117 | B | | |
| 1-118 | B | | |
| 1-119 | A | | |
| 1-120 | A | | |
| 1-121 | A | | |
| 1-122 | A | | |
| 1-132 | A | | |
| 1-134 | A | | |
| 1-141 | B | | |
| 1-146 | B | | |
| 1-153 | A | | |
| 1-162 | B | | |
| 1-178 | A | | |
| 1-184 | B | | |

TABLE 64-continued

| Compound No. | Evaluation | Compound No. | Evaluation |
|---|---|---|---|
| 1-199 | B | | |
| 1-266 | B | | |
| 1-274 | A | | |
| 1-333 | A | | |
| 1-349 | B | | |
| 1-404 | B | | |
| 1-1327 | A | | |
| 1-1372 | B | | |
| 1-1409 | B | | |
| 1-1415 | B | | |
| 1-1417 | B | | |
| 1-1418 | A | | |
| 1-1419 | A | | |
| 1-1420 | A | | |
| 1-1423 | B | | |
| 1-1424 | B | | |
| 1-1425 | B | | |
| 1-1427 | B | | |

The agricultural/horticultural fungicides of the present invention are useful as agricultural/horticultural fungicides because they have high controlling effects on cucumber downy mildew, apple scab, wheat powdery mildew, rice blast, cucumber gray mold and rice sheath blight without damaging crops, and are excellent in residual effectiveness and rain-fastness.

What is claimed is:

1. A phenylacetylene derivative represented by the formula:

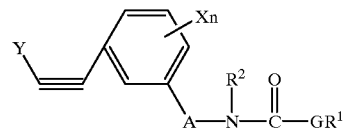

wherein
X is a halogen atom, a $C_1$–$C_6$ alkyl group, a $C_1$–$C_6$ alkoxy group, a $C_1$–$C_6$ haloalkyl group or a $C_1$–$C_6$ haloalkoxy group;
n is 0 or an integer from 1 to 4;
$R^1$ is a $C_1$–$C_6$ alkyl group;
$R^2$ is a hydrogen atom, a $C_1$–$C_6$ alkyl group, a $C_2$–$C_6$ alkenyl group, a $C_2$–$C_6$ alkynyl group, a $C_1$–$C_6$ alkoxy group, a $C_1$–$C_6$ alkoxy-$C_1$–$C_6$ alkyl group, a $C_1$–$C_6$ alkylcarbonyl group or a $C_1$–$C_6$ alkoxycarbonyl group;
A is a $C_1$–$C_6$ alkylene group which may be branched;
G is an oxygen atom, a sulfur atom or a —$NR^3$— group, wherein $R^3$ is a hydrogen atom or a $C_1$–$C_6$ alkyl group; and
Y is a hydrogen atom; a $C_1$–$C_{10}$ alkyl group that may be substituted by a halogen atom, a hydroxyl group or a $C_1$–$C_6$ alkoxy group; a $C_2$–$C_{10}$ alkenyl group, a $C_2$–$C_{10}$ alkynyl group; a $C_3$–$C_6$ cycloalkyl group that may be substituted by a halogen atom, a hydroxyl group or a $C_1$–$C_6$ alkoxy group; a $C_3$–$C_6$ cycloalkenyl group, a $C_3$–$C_6$ cycloalkyl-$C_1$–$C_6$ alkyl group; an aryl-$C_1$–$C_6$ alkyl group that may be substituted by a halogen atom, a $C_1$–$C_6$ alkyl group or a $C_1$–$C_6$ alkoxy group; $C(O)R^4$, $COOR^5$, a $SiR^6R^7R^8$—$C_1$–$C_6$ alkyl group, or a $SiR^6R^7R^8$ group, wherein $R^4$—$R^8$ are the same or different and represent a hydrogen atom or a $C_1$–$C_6$ alkyl group.

2. The phenylacetylene derivative according to claim 1, wherein G is an oxygen atom.

3. The phenylacetylene derivative according to claim 1, wherein $R^1$ is methyl.

4. An agricultural/horticultural fungicide containing the phenylacetylene derivative as defined in claim 1, as the active ingredient.

5. A method for controlling an agricultural/horticultural plant disease, which comprises treating plant seeds, foliage, soil, or any other plant environment in which to control or keep free of fungi, with a fungicidally effective amount of the phenylacetylene derivative as defined in claim 1.

6. An agricultural/horticultural fungicide containing the phenylacetylene derivative as defined in claim 2, as the active ingredient.

7. A method for controlling an agricultural/horticultural plant disease, which comprises treating plant seeds, foliage, soil, or any other plant environment in which to control or keep free of fungi, with a fungicidally effective amount of the phenylacetylene derivative as defined in claim 2.

8. An agricultural/horticultural fungicide containing the phenylacetylene derivative as defined in claim 3, as the active ingredient.

9. A method for controlling an agricultural/horticultural plant disease, which comprises treating plant seeds, foliage, soil, or any other plant environment in which to control or keep free of fungi, with a fungicidally effective amount of the phenylacetylene derivative as defined in claim 3.

* * * * *